US012790618B2

(12) United States Patent
Arosio et al.

(10) Patent No.: US 12,790,618 B2
(45) Date of Patent: Nov. 10, 2026

(54) EXPRESSION AND PURIFICATION OF RECOMBINANT HUMAN ISOFERRITINS USING A NOVEL EXPRESSION SYSTEM

(71) Applicant: THE RESEARCH FOUNDATION FOR SUNY, Albany, NY (US)

(72) Inventors: Paolo Arosio, Brescia (IT); Fadi Bou-Abdallah, Potsdam, NY (US); Maura Poli, Brescia (IT); Ayush Kumar Srivastava, Potsdam, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 721 days.

(21) Appl. No.: 17/793,274

(22) PCT Filed: Jan. 21, 2021

(86) PCT No.: PCT/US2021/014473

§ 371 (c)(1),
(2) Date: Jul. 15, 2022

(87) PCT Pub. No.: WO2021/150795

PCT Pub. Date: Jul. 29, 2021

(65) Prior Publication Data

US 2023/0348916 A1 Nov. 2, 2023

Related U.S. Application Data

(60) Provisional application No. 62/963,758, filed on Jan. 21, 2020.

(51) Int. Cl.

| | |
|---|---|
| ***C12N 15/70*** | (2006.01) |
| ***C07K 14/79*** | (2006.01) |
| ***C12R 1/19*** | (2006.01) |

(52) U.S. Cl.
CPC .............. *C12N 15/70* (2013.01); *C07K 14/79* (2013.01); *C12R 2001/19* (2021.05)

(58) Field of Classification Search
CPC ................................ C12N 15/70; A61K 38/00
See application file for complete search history.

(56) References Cited

U.S. PATENT DOCUMENTS

2012/0021450 A1* 1/2012 Ahrens .............. A61K 49/1896
536/23.4

FOREIGN PATENT DOCUMENTS

EP 2080812 A1 * 7/2009
GB 2555131 A * 4/2018

OTHER PUBLICATIONS

Shipman, Seth L., et al., Molecular recordings by directed CRISPR spacer acquisition, Synthetic Biology, Jul. 29, 2016, pp. 463-474, vol. 353 Issue 6298, American Association for the Advancement of Science, Washington DC, USA.

* cited by examiner

*Primary Examiner* — Brian Gangle
*Assistant Examiner* — Lakia J Jackson-Tongue
(74) *Attorney, Agent, or Firm* — Peter J. Fallon

(57) ABSTRACT

The present disclosure relates to methods of making of one or more bioengineered ferritin proteins having a preselected ratio of H-subunits (ferritin heavy chain (FTH or H)) to L-subunits (ferritin light chain (FTL or L)). The disclosure further relates to cDNAs, vectors, and host cells for forming the bioengineered ferritin proteins of the present disclosure.

8 Claims, 22 Drawing Sheets

Specification includes a Sequence Listing.

12% SDS PAGE 7.5% Native PAGE

| IPTG Concentration (μM) | Anhydrotetracycline Concentration (ng/ml) | Predicted H:L ratio (based on gels) | Measured H:L ratio by CE |
|---|---|---|---|
| Using pWUR Plasmid and Rosetta Gami B E. coli strain | | | |
| 100 | 100 | ~ 90H:10L (H-rich) | 88H:12L |
| 50-100 | 600 | ~ 85H:15L | 88H:12L |
| 10 | 600 | ~ 40H:60L | 36H:64L |
| 10 | 800 | ~ 80H:20L | 82H:18L |
| 20 | 800 | ~ 80H:20L | 80H:20L |
| 50 | 800 | ~ 85H:15L | 86H:14L |
| 100 | 800 | ~85H:15L | 88H:12L |
| 10 | 1000 | ~ 25H:75L | 27H:73L |
| 0 | 800-1200 | ~ 100 % L | 6H:94L |

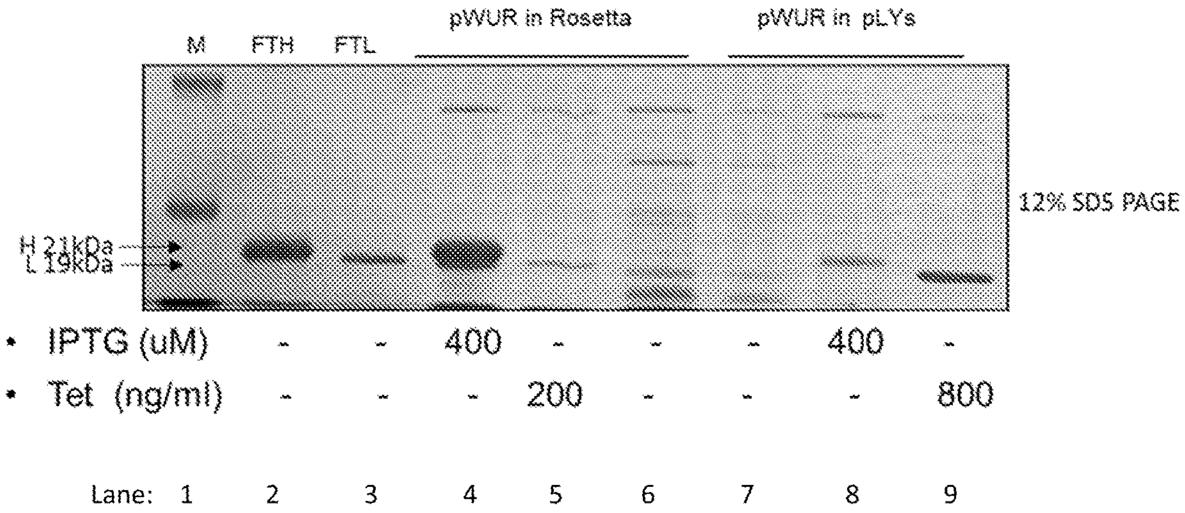
FIG. 19
FIG. 20A
FIG. 20B
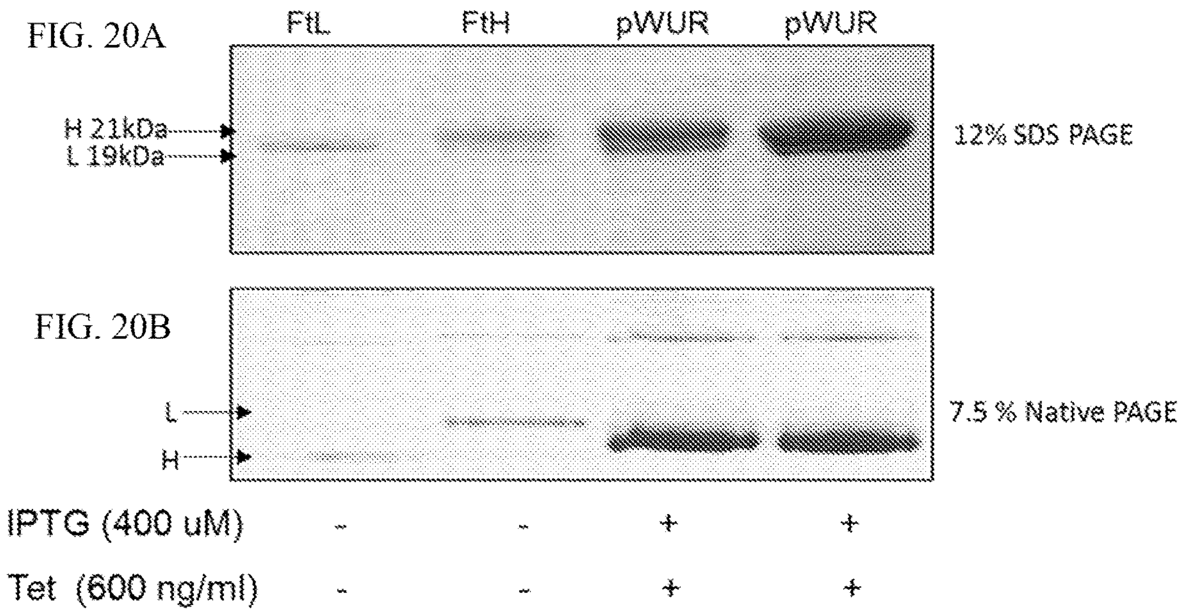

SEQUENCE LISTING

```
<160> NUMBER OF SEQ ID NOS: 18

<210> SEQ ID NO 1
<211> LENGTH: 87
<212> TYPE: DNA
<213> ORGANISM: Artificial Sequence
<220> FEATURE:
<223> OTHER INFORMATION: Synthetic Sequence
```

<400> SEQUENCE: 1
taatacgact cactataggg gaattgtgag cggataacaa ttcccctgta gaaataattt 60
tgtttaactt taataaggag atatacc 87

<210> SEQ ID NO 2
<211> LENGTH: 558
<212> TYPE: DNA
<213> ORGANISM: Artificial Sequence
<220> FEATURE:
<223> OTHER INFORMATION: Synthetic Sequence

<400> SEQUENCE: 2
atggctagca cgaccgcgtc cacctcgcag gtgcgccaga actaccacca ggactcagag 60
gccgccatca accgccagat caacctggag ctctacgcct cctacgttta cctgtccatg 120
tcttactact ttgaccgcga tgatgtggct ttgaagaact ttgccaaata ctttcttcac 180
caatctcatg aggagaggga acatgctgag aaactgatga agctgcagaa ccaacgaggt 240
ggccgaatct tccttcagga tatcaagaaa ccagactgtg atgactggga gagcgggctg 300
aatgcaatgg agtgtgcatt acatttggaa aaaaatgtga atcagtcact actggaactg 360
cacaaactgg ccactgacaa aaatgacccc catttgtgtg acttcattga gacacattac 420
ctgaatgagc aggtgaaagc catcaaagaa ttgggtgacc acgtgaccaa cttgcgcaag 480
atgggagcgc ccgaatctgg cttggcggaa tatctctttg acaagcacac cctgggagac 540
agtgataatg aaagctaa 558

<210> SEQ ID NO 3
<211> LENGTH: 570
<212> TYPE: DNA
<213> ORGANISM: Artificial Sequence
<220> FEATURE:
<223> OTHER INFORMATION: Synthetic Sequence

<400> SEQUENCE: 3
gcggccgcgg ctgttttggc ggatgagaga agattttcag cctgatacag attaaatcag 60
aacgcagaag cggtctgata aaacagaatt tgcctggcgg cagtagcgcg gtggtcccac 120
ctgaccccat gccgaactca gaagtgaaac gccgtagcgc cgatggtagt gtggggtctc 180
cccatgcgag agtagggaac tgccaggcat caaataaaac gaaaggctca gtcgaaagac 240
tgggcctttc gttttatctg ttgtttgtcg gtgaacgctc tcctgagtag gacaaatccg 300
ccgggagcgg atttgaacgt tgcgaagcaa cggcccggag ggtggcgggc aggacgcccg 360
ccataaactg ccaggcatca aattaagcag aaggccatcc gtcaggatgg cctttttgcg 420
tttctacaaa ctctgctagc aagtaaggcc gactcgagtc cctatcagtg atagagattg 480
acatccctat cagtgataga gatactgagc acatcagcag gacgcactga ccgaattcat 540
taaatttaac tttaagaagg agatatacat 570

<210> SEQ ID NO 4
<211> LENGTH: 528
<212> TYPE: DNA
<213> ORGANISM: Artificial Sequence
<220> FEATURE:
<223> OTHER INFORMATION: Synthetic Sequence

<400> SEQUENCE: 4
atgagctccc agattcgtca gaattattcc accgacgtgg aggcagccgt caacagcctg 60
gtcaatttgt acctgcaggc ctcctacacc tacctctctc tgggcttcta tttcgaccgc 120
gatgatgtgg ctctggaagg cgtgagccac ttcttccgcg aattggccga ggagaagcgc 180
gagggctacg agcgtctcct gaagatgcaa aaccagcgtg gcggccgcgc tctcttccag 240
gacatcaaga agccagctga agatgagtgg ggtaaaaccc cagacgccat gaaagctgcc 300
atggccctgg agaaaaagct gaaccaggcc cttttggatc ttcatgccct gggttctgcc 360
cgcacggacc cccatctctg tgacttcctg gagactcact tcctagatga ggaagtgaag 420
cttatcaaga agatgggtga ccacctgacc aacctccaca ggctgggtgg cccggaggct 480
gggctgggcg agtatctctt cgaaaggctc actctcaagc acgactaa 528

<210> SEQ ID NO 5
<211> LENGTH: 4291
<212> TYPE: DNA
<213> ORGANISM: Artificial Sequence
<220> FEATURE:
<223> OTHER INFORMATION: Synthetic Sequence

<400> SEQUENCE: 5
gccttaatta acggcactcc tcagcaaata taatgaccct cttgataacc caagagggca 60 tttttaatg cccatggcgt ttaccacagc taacaccacg tcgtccctat ctgctgccct 120
aggtctatga gtggttgctg gataacttta cgggcatgca taaggctcgt aggctatatt 180
cagggagacc acaacggttt ccctctacaa ataattttgt ttaactttga aataaggagg 240
taatacaaat gtctcgttta gataaaagta aagtgattaa cagcgcatta gagctgctta 300
atgaggtcgg aatcgaaggt ttaacaaccc gtaaactcgc ccagaagcta ggtgtagagc 360
agcctacatt gtattggcat gtaaaaaata agcgggcttt gctcgacgcc ttagccattg 420
agatgttaga taggcaccat actcactttt gccctttaga aggggaaagc tggcaagatt 480
ttttacgtaa taacgctaaa agttttagat gtgctttact aagtcatcgc gatggagcaa 540
aagtacattt aggtacacgg cctacagaaa aacagtatga aactctcgaa aatcaattag 600
cctttttatg ccaacaaggt ttttcactag agaatgcatt atatgcactc agcgctgtgg 660
ggcattttac tttaggttgc gtattggaag atcaagagca tcaagtcgct aaagaagaaa 720
gggaaacacc tactactgat agtatgccgc cattattacg acaagctatc gaattatttg 780
atcaccaagg tgcagagcca gccttcttat tcggccttga attgatcata tgcggattag 840
aaaaacaact taaatgtgaa agtgggtctt aataagcgac ctcgagtctg gtaaagaaac 900
cgctgctgcg aaatttgaac gccagcacat ggactcgtct actagcgcag cttaattaac 960
ctaggctgct gccaccgctg agcaataact agcataaccc cttggggcct ctaaacgggt 1020
cttgaggggt tttttgctga aacctcaggc atttgagaag cacacggtca cactgcttcc 1080
ggtagtcaat aaaccggtaa accagcaata gacataagcg gctatttaac gaccctgccc 1140
tgaaccgacg accgggtcat cgtggccgga tcttgcggcc cctcggcttg aacgaattgt 1200
tagacattat ttgccgacta ccttggtgat ctcgcctttc acgtagtgga caaattcttc 1260
caactgatct gcgcgcgagg ccaagcgatc ttcttcttgt ccaagataag cctgtctagc 1320
ttcaagtatg acgggctgat actgggccgg caggcgctcc attgcccagt cggcagcgac 1380
atccttcggc gcgattttgc cggttactgc gctgtaccaa atgcgggaca acgtaagcac 1440
tacatttcgc tcatcgccag cccagtcggg cggcgagttc catagcgtta aggtttcatt 1500
tagcgcctca aatagatcct gttcaggaac cggatcaaag agttcctccg ccgctggacc 1560
taccaaggca acgctatgtt ctcttgcttt tgtcagcaag atagccagat caatgtcgat 1620

```
cgtggctggc tcgaagatac ctgcaagaat gtcattgcgc tgccattctc caaattgcag   1680
ttcgcgctta gctggataac gccacggaat gatgtcgtcg tgcacaacaa tggtgacttc   1740
tacagcgcgg agaatctcgc tctctccagg ggaagccgaa gtttccaaaa ggtcgttgat   1800
caaagctcgc cgcgttgttt catcaagcct tacggtcacc gtaaccagca aatcaatatc   1860
actgtgtggc ttcaggccgc catccactgc ggagccgtac aaatgtacgg ccagcaacgt   1920
cggttcgaga tggcgctcga tgacgccaac tacctctgat agttgagtcg atacttcggc   1980
gatcaccgct tccctcatac tcttcctttt tcaatattat tgaagcattt atcagggtta   2040
ttgtctcatg agcggataca tatttgaatg tatttagaaa aataaacaaa tagctagctc   2100
actcggtcgc tacgctccgg gcgtgagact gcggcgggcg ctgcggacac atacaaagtt   2160
acccacagat tccgtggata agcaggggac taacatgtga ggcaaaacag cagggccgcg   2220
ccggtggcgt ttttccatag gctccgccct cctgccagag ttcacataaa cagacgcttt   2280
tccggtgcat ctgtgggagc cgtgaggctc aaccatgaat ctgacagtac gggcgaaacc   2340
cgacaggact taaagatccc caccgtttcc ggcgggtcgc tccctcttgc gctctcctgt   2400
tccgaccctg ccgtttaccg gatacctgtt ccgcctttct cccttacggg aagtgtggcg   2460
ctttctcata gctcacacac tggtatctcg gctcggtgta ggtcgttcgc tccaagctgg   2520
gctgtaagca agaactcccc gttcagcccg actgctgcgc cttatccggt aactgttcac   2580
ttgagtccaa cccggaaaag cacggtaaaa cgccactggc agcagccatt ggtaactggg   2640
agttcgcaga ggatttgttt agctaaacac gcggttgctc ttgaagtgtg cgccaaagtc   2700
cggctacact ggaaggacag atttggttgc tgtgctctgc gaaagccagt taccacggtt   2760
aagcagttcc ccaactgact taaccttcga tcaaaccacc tccccaggtg gttttttcgt   2820
ttacagggca aaagattacg cgcagaaaaa aaggatctca agaagatcct ttgatctttt   2880
ctactgaacc gctctagatt tcagtgcaat ttatctcttc aaatgtagca cctgaagtca   2940
gccccatacg atataagttg taattctcat gttagtcatg ccccgcgccc accggaagga   3000
gctgactggg ttgaaggctc tcaagggcat cggtcgagat cccggtgcct aatgagtgag   3060
ctaacttaca ttaattgcgt tgcgctcact gcccgctttc cagtcgggaa acctgtcgtg   3120
ccagctgcat taatgaatcg gccaacgcgc ggggagaggc ggtttgcgta ttgggcgcca   3180
gggtggtttt tcttttcacc agtgagacgg gcaacagctg attgcccttc accgcctggc   3240
cctgagagag ttgcagcaag cggtccacgc tggtttgccc cagcaggcga aaatcctgtt   3300
tgatggtggt taacggcggg atataacatg agctgtcttc ggtatcgtcg tatcccacta   3360
ccgagatgtc cgcaccaacg cgcagcccgg actcggtaat ggcgcgcatt gcgcccagcg   3420
ccatctgatc gttggcaacc agcatcgcag tgggaacgat gccctcattc agcatttgca   3480
tggtttgttg aaaaccggac atggcactcc agtcgccttc ccgttccgct atcggctgaa   3540
tttgattgcg agtgagatat ttatgccagc cagccagacg cagacgcgcc gagacagaac   3600
ttaatgggcc cgctaacagc gcgatttgct ggtgacccaa tgcgaccaga tgctccacgc   3660
ccagtcgcgt accgtcttca tgggagaaaa taatactgtt gatgggtgtc tggtcagaga   3720
catcaagaaa taacgccgga acattagtgc aggcagcttc cacagcaatg gcatcctggt   3780
catccagcgg atagttaatg atcagcccac tgacgcgttg cgcgagaaga ttgtgcaccg   3840
ccgctttaca ggcttcgacg ccgcttcgtt ctaccatcga caccaccacg ctggcaccca   3900
gttgatcggc gcgagattta atcgccgcga caatttgcga cggcgcgtgc agggccagac   3960
```

tggaggtggc aacgccaatc agcaacgact gtttgcccgc cagttgttgt gccacgcggt 4020
tgggaatgta attcagctcc gccatcgccg cttccacttt ttcccgcgtt ttcgcagaaa 4080
cgtggctggc ctggttcacc acgcgggaaa cggtctgata agagacaccg gcatactctg 4140
cgacatcgta taacgttact ggtttcacat tcaccaccct gaattgactc tcttccgggc 4200
gctatcatgc cataccgcga aaggttttgc gccattcgat ggtgtccggg atctcgacgc 4260
tctcccttat gcgactcctg cattaggaaa t 4291

<210> SEQ ID NO 6
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 6
agccttaatt aacggcactc c 21

<210> SEQ ID NO 7
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 7
ggtatatctc cttattaaag ttaaac 26

<210> SEQ ID NO 8
<211> LENGTH: 38
<212> TYPE: DNA
<213> ORGANISM: artificial Sequence
<220> FEATURE:
<223> OTHER INFORMATION: Synthetic Sequence

<400> SEQUENCE: 8
ctttaataag gagatatacc atggctagca cgaccgcg 38

<210> SEQ ID NO 9
<211> LENGTH: 38
<212> TYPE: DNA
<213> ORGANISM: Artificial Sequence
<220> FEATURE:
<223> OTHER INFORMATION: Synthtetic Sequence

<400> SEQUENCE: 9
ccgcggccgc ttagctttca ttatcactgt ctcccagg 38

<210> SEQ ID NO 10
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 10
tgaaagctaa gcggccgcgg ctgttttg 28

<210> SEQ ID NO 11
<211> LENGTH: 58
<212> TYPE: DNA
<213> ORGANISM: Artificial Sequence
<220> FEATURE:
<223> OTHER INFORMATION: Synthetic Sequence

<400> SEQUENCE: 11
gggagctcat atgtatatct ccttcttaaa gttaaattta atgaattcgg tcagtgcg 58

<210> SEQ ID NO 12
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 12
agatatacat atgagctccc agattcgtc 29

<210> SEQ ID NO 13
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 13
gagtgccgtt aattaaggct ttagtcgtgc ttgagagtg 39

<210> SEQ ID NO 14
<211> LENGTH: 6034
<212> TYPE: DNA
<213> ORGANISM: Artificial Sequence
<220> FEATURE:
<223> OTHER INFORMATION: Synthetic Sequence

<400> SEQUENCE: 14
taatacgact cactataggg gaattgtgag cggataacaa ttcccctgta gaaataattt 60
tgtttaactt taataaggag atataccatg gctagcacga ccgcgtccac ctcgcaggtg 120
cgccagaact accaccagga ctcagaggcc gccatcaacc gccagatcaa cctggagctc 180
tacgcctcct acgtttacct gtccatgtct tactactttg accgcgatga tgtggctttg 240
aagaactttg ccaaatactt tcttcaccaa tctcatgagg agagggaaca tgctgagaaa 300
ctgatgaagc tgcagaacca acgaggtggc cgaatcttcc ttcaggatat caagaaacca 360
gactgtgatg actgggagag cgggctgaat gcaatggagt gtgcattaca tttggaaaaa 420
aatgtgaatc agtcactact ggaactgcac aaactggcca ctgacaaaaa tgacccccat 480
ttgtgtgact tcattgagac acattacctg aatgagcagg tgaaagccat caaagaattg 540
ggtgaccacg tgaccaactt gcgcaagatg ggagcgcccg aatctggctt ggcggaatat 600
ctctttgaca agcacaccct gggagacagt gataatgaaa gctaagcggc cgcggctgtt 660
ttggcggatg agagaagatt ttcagcctga tacagattaa atcagaacgc agaagcggtc 720
tgataaaaca gaatttgcct ggcggcagta gcgcggtggt cccacctgac cccatgccga 780
actcagaagt gaaacgccgt agcgccgatg gtagtgtggg gtctccccat gcgagagtag 840
ggaactgcca ggcatcaaat aaaacgaaag gctcagtcga aagactgggc ctttcgtttt 900
atctgttgtt tgtcggtgaa cgctctcctg agtaggacaa atccgccggg agcggatttg 960
aacgttgcga agcaacggcc cggagggtgg cgggcaggac gcccgccata aactgccagg 1020
catcaaatta agcagaaggc catccgtcag gatggccttt ttgcgtttct acaaactctg 1080
ctagcaagta aggccgactc gagtccctat cagtgataga gattgacatc cctatcagtg 1140
atagagatac tgagcacatc agcaggacgc actgaccgaa ttcattaaat ttaactttaa 1200

```
gaaggagata tacatatgag ctcccagatt cgtcagaatt attccaccga cgtggaggca   1260
gccgtcaaca gcctggtcaa tttgtacctg caggcctcct acacctacct ctctctgggc   1320
ttctatttcg accgcgatga tgtggctctg gaaggcgtga gccacttctt ccgcgaattg   1380
gccgaggaga agcgcgaggg ctacgagcgt ctcctgaaga tgcaaaacca gcgtggcggc   1440
cgcgctctct tccaggacat caagaagcca gctgaagatg agtggggtaa aaccccagac   1500
gccatgaaag ctgccatggc cctggagaaa aagctgaacc aggccctttt ggatcttcat   1560
gccctgggtt ctgcccgcac ggacccccat ctctgtgact tcctggagac tcacttccta   1620
gatgaggaag tgaagcttat caagaagatg ggtgaccacc tgaccaacct ccacaggctg   1680
ggtggcccgg aggctgggct gggcgagtat ctcttcgaaa ggctcactct caagcacgac   1740
taagccttaa ttaacggcac tcctcagcaa atataatgac cctcttgata acccaagagg   1800
gcatttttta atgcccatgg cgtttaccac agctaacacc acgtcgtccc tatctgctgc   1860
cctaggtcta tgagtggttg ctggataact ttacgggcat gcataaggct cgtaggctat   1920
attcagggag accacaacgg tttccctcta caaataattt tgtttaactt tgaaataagg   1980
aggtaataca aatgtctcgt ttagataaaa gtaaagtgat taacagcgca ttagagctgc   2040
ttaatgaggt cggaatcgaa ggtttaacaa cccgtaaact cgcccagaag ctaggtgtag   2100
agcagcctac attgtattgg catgtaaaaa ataagcgggc tttgctcgac gccttagcca   2160
ttgagatgtt agataggcac catactcact tttgcccttt agaaggggaa agctggcaag   2220
atttttacg taataacgct aaaagtttta gatgtgcttt actaagtcat cgcgatggag   2280
caaaagtaca tttaggtaca cggcctacag aaaaacagta tgaaactctc gaaaatcaat   2340
tagccttttt atgccaacaa ggtttttcac tagagaatgc attatatgca ctcagcgctg   2400
tggggcattt tactttaggt tgcgtattgg aagatcaaga gcatcaagtc gctaaagaag   2460
aaagggaaac acctactact gatagtatgc cgccattatt acgacaagct atcgaattat   2520
ttgatcacca aggtgcagag ccagccttct tattcggcct tgaattgatc atatgcggat   2580
tagaaaaaca acttaaatgt gaaagtgggt cttaataagc gacctcgagt ctggtaaaga   2640
aaccgctgct gcgaaatttg aacgccagca catggactcg tctactagcg cagcttaatt   2700
aacctaggct gctgccaccg ctgagcaata actagcataa ccccttgggg cctctaaacg   2760
ggtcttgagg ggttttttgc tgaaacctca ggcatttgag aagcacacgg tcacactgct   2820
tccggtagtc aataaaccgg taaaccagca atagacataa gcggctattt aacgaccctg   2880
ccctgaaccg acgaccgggt catcgtggcc ggatcttgcg gcccctcggc ttgaacgaat   2940
tgttagacat tatttgccga ctaccttggt gatctcgcct ttcacgtagt ggacaaattc   3000
ttccaactga tctgcgcgcg aggccaagcg atcttcttct tgtccaagat aagcctgtct   3060
agcttcaagt atgacgggct gatactgggc cggcaggcgc tccattgccc agtcggcagc   3120
gacatccttc ggcgcgattt tgccggttac tgcgctgtac caaatgcggg acaacgtaag   3180
cactacattt cgctcatcgc cagcccagtc gggcggcgag ttccatagcg ttaaggtttc   3240
atttagcgcc tcaaatagat cctgttcagg aaccggatca aagagttcct ccgccgctgg   3300
acctaccaag gcaacgctat gttctcttgc ttttgtcagc aagatagcca gatcaatgtc   3360
gatcgtggct ggctcgaaga tacctgcaag aatgtcattg cgctgccatt ctccaaattg   3420
cagttcgcgc ttagctggat aacgccacgg aatgatgtcg tcgtgcacaa caatggtgac   3480
ttctacagcg cggagaatct cgctctctcc aggggaagcc gaagtttcca aaaggtcgtt   3540
gatcaaagct cgccgcgttg tttcatcaag ccttacggtc accgtaacca gcaaatcaat   3600
```

atcactgtgt ggcttcaggc cgccatccac tgcggagccg tacaaatgta cggccagcaa 3660
cgtcggttcg agatggcgct cgatgacgcc aactacctct gatagttgag tcgatacttc 3720
ggcgatcacc gcttccctca tactcttcct tttcaatat tattgaagca tttatcaggg 3780
ttattgtctc atgagcggat acatatttga atgtatttag aaaaataaac aaatagctag 3840
ctcactcggt cgctacgctc cgggcgtgag actgcggcgg gcgctgcgga cacatacaaa 3900
gttacccaca gattccgtgg ataagcaggg gactaacatg tgaggcaaaa cagcagggcc 3960
gcgccggtgg cgtttttcca taggctccgc cctcctgcca gagttcacat aaacagacgc 4020
ttttccggtg catctgtggg agccgtgagg ctcaaccatg aatctgacag tacgggcgaa 4080
acccgacagg acttaaagat ccccaccgtt tccggcgggt cgctccctct tgcgctctcc 4140
tgttccgacc ctgccgttta ccggatacct gttccgcctt tctcccttac gggaagtgtg 4200
gcgctttctc atagctcaca cactggtatc tcggctcggt gtaggtcgtt cgctccaagc 4260
tgggctgtaa gcaagaactc cccgttcagc ccgactgctg cgccttatcc ggtaactgtt 4320
cacttgagtc caacccggaa aagcacggta aaacgccact ggcagcagcc attggtaact 4380
gggagttcgc agaggatttg tttagctaaa cacgcggttg ctcttgaagt gtgcgccaaa 4440
gtccggctac actggaagga cagatttggt tgctgtgctc tgcgaaagcc agttaccacg 4500
gttaagcagt tccccaactg acttaacctt cgatcaaacc acctccccag gtggtttttt 4560
cgtttacagg gcaaaagatt acgcgcagaa aaaaaggatc tcaagaagat cctttgatct 4620
tttctactga accgctctag atttcagtgc aatttatctc ttcaaatgta gcacctgaag 4680
tcagccccat acgatataag ttgtaattct catgttagtc atgccccgcg cccaccggaa 4740
ggagctgact gggttgaagg ctctcaaggg catcggtcga gatcccggtg cctaatgagt 4800
gagctaactt acattaattg cgttgcgctc actgcccgct ttccagtcgg gaaacctgtc 4860
gtgccagctg cattaatgaa tcggccaacg cgcggggaga ggcggtttgc gtattgggcg 4920
ccagggtggt ttttcttttc accagtgaga cgggcaacag ctgattgccc ttcaccgcct 4980
ggccctgaga gagttgcagc aagcggtcca cgctggtttg ccccagcagg cgaaaatcct 5040
gtttgatggt ggttaacggc gggatataac atgagctgtc ttcggtatcg tcgtatccca 5100
ctaccgagat gtccgcacca acgcgcagcc cggactcggt aatggcgcgc attgcgccca 5160
gcgccatctg atcgttggca accagcatcg cagtgggaac gatgccctca ttcagcattt 5220
gcatggtttg ttgaaaaccg gacatggcac tccagtcgcc ttcccgttcc gctatcggct 5280
gaatttgatt gcgagtgaga tatttatgcc agccagccag acgcagacgc gccgagacag 5340
aacttaatgg gcccgctaac agcgcgattt gctggtgacc caatgcgacc agatgctcca 5400
cgcccagtcg cgtaccgtct tcatgggaga aaataatact gttgatgggt gtctggtcag 5460
agacatcaag aaataacgcc ggaacattag tgcaggcagc ttccacagca atggcatcct 5520
ggtcatccag cggatagtta atgatcagcc cactgacgcg ttgcgcgaga agattgtgca 5580
ccgccgcttt acaggcttcg acgccgcttc gttctaccat cgacaccacc acgctggcac 5640
ccagttgatc ggcgcgagat ttaatcgccg cgacaatttg cgacggcgcg tgcagggcca 5700
gactggaggt ggcaacgcca atcagcaacg actgtttgcc cgccagttgt tgtgccacgc 5760
ggttgggaat gtaattcagc tccgccatcg ccgcttccac tttttcccgc gttttcgcag 5820
aaacgtggct ggcctggttc accacgcggg aaacggtctg ataagagaca ccggcatact 5880
ctgcgacatc gtataacgtt actggtttca cattcaccac cctgaattga ctctcttccg 5940
ggcgctatca tgccataccg cgaaaggttt tgcgccattc gatggtgtcc gggatctcga 6000
cgctctccct tatgcgactc ctgcattagg aaat 6034

<210> SEQ ID NO 15
<211> LENGTH: 8571
<212> TYPE: DNA
<213> ORGANISM: Homo sapiens

<400> SEQUENCE: 15
tcagcatccc aaggagctgg gattacaggt gcctgccacc acacccagct aatttttgta 60
tttatttatt ttgagatgga gttttgctct tgttgcccag gctggagtgc aatggcgcaa 120
cctcggctca ctgcaacctc cgcctcccgg gttcaagcaa ttctcctgcc tcagactccc 180
aagtagctgg gattacaggc atgtgccacc acgcccggct aattttgtat ttttagtaga 240
gatggcatta ctccgtattg gtcaggctgg tcttgaactc ccgacctcaa gtgatccgcc 300
tgccttggcc tcccaaagtg ctgggattac aggcatgagc cgccgcacct ggccatgttt 360
acaatttttg aagccgactt caattgtggg tggcagaaat ctttgagggg aggcaaagaa 420
ttgacaaagg aggtttgggg ccactatctc caggcagtgg ggacaaggtt cagtccctaa 480
cgcccactcc actccccaca ggccctgtgc accaaggtgc cggaactgat cagaaccatc 540
atgggctgga cattggactt cctccgggag cggctgttgg gctggatcca agaccagggt 600
ggttgggtga gactcctcaa gcctcctcac ccccaccacc gcgccctcac caccgcccct 660
gccccaccgt ccctgccccc cgccactcct ctgggaccct gggccttctg gagcaggtca 720
cagtggtgcc ctctccccat cttcagatca tcagatgtgg tctataatgc gttttcctta 780
cgtgtctgat caatccccga ttcatctacc ctgctgacct cccagtgacc cctgacctca 840
ctgtgacctt gacttgatta gtgccttctg ccctccctgg agcctccact gcctctggaa 900
ttgctcaagt tcattgatga ccctctgacc ctagctcttt ccttttttttt tttttcccca 960 ctgagaaggg gtctcgctat gttgcccagg ttggtctcga actcctggcc tcaagcgatc 1020
ctcccgcctc agcctctcaa agtgctggga ttacaggtgt gagccaccat gcctggcctg 1080
agtccagctc tttaatgccc gttcatctca gtcccctgcc cgcaatcctg ccttctggcc 1140
tcctccgtcc ctgatcccgc ctctgcctgc ccaggggctg cccctggccg agtcactgaa 1200
gcgactgatg tccctgtctc caggacggcc tcctctccta ctttgggacg cccacgtggc 1260
agaccgtgac catctttgtg gcgggagtgc tcaccgcctc actcaccatc tggaagaaga 1320
tgggctgagg cccccagctg ccttggactg tgtttttcct ccataaatta tggcattttt 1380
ctgggagggg tggggattgg gggacgtggg catttttctt acttttgtaa ttattggggg 1440
gtgtggggaa gagtggtctt gagggggtaa taaacctcct tcgggacaca cttcggcatc 1500
tgagtcactg ggcctctgcc ccgctccccg gcacgtcagg agagcaggcc ctgtccgctg 1560
ccccacgccg ggcccgccgt ctgctggcct agagatacct gcttgggcca ctcagggacg 1620
tggggctctc tgcactcact tgacatcttt ttctggggtg ccctgtgggg tctgtgggtt 1680
agggatgagt tggtcctggg cctgacctgc aggagctcac gggaaaggaa aagaagggag 1740
ctcacgggaa aggaaaaggg agctcacggg aaacgagggt gataggtggt acatctgtcg 1800
cagcccagga tgatctgtgc gggacagagg cagcggcctg tgaggcccaa gcaggcgtgt 1860
gggtaaggga agaacagcac ggccggctgc agagcaagcc tcctcggccc ggggaccaca 1920
gcctggcgtg tcacacgtgg gacctcagga ggccatacct ttaccgagct ggagaatggg 1980
agtgggggga ggagggatgg gaggaccaga ggagcaggaa gggctctgga gcctggtggt 2040

```
gaggtcgctg gagggtggca ggctgaggac accagggcga gggcccacgg gagaggcctc   2100
ctgagctggg ctgaggacag agaggaaggg acctggctgg cgactgagag gctggagggc   2160
agggcagagg aggaggaacc tggtctggcc ccacagctgg gtggggcccc cctggagagg   2220
aactgccgga agaaggtgct gagctcagag gcccagtgac cttagacaca ggcggagcga   2280
agacaagggg gctagaggat gtgggttctc agtcacaggg tctctggcac ccccctctgg   2340
gtctttaccc cctcccatct ctgggtctct gtccccatgc tctgggtctt tgctttccga   2400
gcctctgttc ccaccccacc tttggccctc tttctctggg cctctttcca cccctggcac   2460
ccagacctct ggccccctct ctctgggtct ctgtcccccc ctctggatct ctggcccccc   2520
atctctctct gggtctgtcc cccgaccctg agtttctgtc tccctctctc tgggtctctg   2580
tcctctctct ggctgtcact ctctcttggg tctctgtacc tcccctctct ctgggtctct   2640
ttccctctcc ccggtctctg tcccccgccc ccgggtccct gtccccgccc ccccaggtct   2700
cagtcctccc tagtctctgt ccccttctct ctgagtccct gtccccccctc tctctgggtc   2760
tctgtacccc cttctctgga tctctgtccc cacctctctc tggatctctg tcccccactc   2820
tggatttctg tcccctcccg ccgggtccct ctgggtctct atcccccccca cccctgggtc   2880
tctgtacctc cctgcctctg tcccccccca cctctgtccc cccctctctc tgggtctctt   2940
ttcccctccc tctgggtctc tgccctcctc tctctaggtc tgtccccctc ccctctctct   3000
cagggtctct gtacccctct gtctccgggt ctgttttccc ctctctctgg gtctctgtcc   3060
ccctctctct cagggtctct gtctgagtct ctttttctct gggcctctgt ctccccaccc   3120
cacgttctct atggtcttca gatcctgtct ctctcagccc ctcctctccc tccacctatg   3180
ggccccaagg cccctctcgg ccgactaaag gtctctgggc tgaggtatga catttggtaa   3240
atgagtaact cgggccccac agtcaacggg gtgctttgga cggctgcccc tcctccatgg   3300
actcttccca gagaccccaa gtcaggggag agagaggggc agaggatcaa tgagtgtaca   3360
ctgagccacc acccagagtg aggggacaat atggccacag gcaggatccc agaaaaaaaa   3420
aaattatggg aaccaaaaag acacggagac aaagcacaca gccggcttcc aacaaggggg   3480
gaccttgggg tagggggccc gatttgggtc tgagccaggt ctagttctga gggtcccacc   3540
aaaaaagtcg gggagtgcca aggggatgag gtcagcgagt ggccccaccc ccatccgtcc   3600
ccgcgggggc cccttcccgc gctgagctca gcatgactca gcagtcgctg cctgcaacaa   3660
ggaccccaga taccggcctg gcggggcatc tgcagatccc ctcggtcagg ggctgccccg   3720
cctgggctgt tcggagcagc tcctctgtag ggcagggcct gacctcaccc cacaccccag   3780
tggcttcagc tccctgccca gcgcacgggc tgcctccatc agggcactta agtagagtca   3840
aggtttgcgc cgactccgtc tcccagaaat caacgtggac caggcccact taaaaaatat   3900
gcattagtcg aagacagacg tctcgtccat aggtccccag actgtttgtc cacaacgcag   3960
ggcttctctt tgtgggcctg aaggagcaca cgtcaggcaa gacacgaggg caacttcaga   4020
gacactgttc agggccacgg agaattctcg aagtctgtga gttgtctcca aaacagcctc   4080
caggaaatgc aatcccagag acaccgcaaa gctcaaaaca gacttttcat tcctccccat   4140
ttccactccc agaaaaagcc tgggccccctg aaagagctcc aaggtatccc caaagtccca   4200
gcccatcttt ggagggttcc agagggctgt ccagggttcc agaagtcacc ctacctcata   4260
caatgctcct cctgggcttc ccgcactggg tgaaacccac ggctccagaa taactgccct   4320
ttccaacttg cagagcacct caagaaccta aagatttccc cggggagggc tccaaaatat   4380
```

-continued agagagtttg catcgtgaac ccccacccct gtaaatccca ggactccagt ccccgcaaca 4440
ctccatcttc cagagatctc caggggtcca gaaataacac ctcacagcct tccaagcttc 4500
ccaaggatcc ggagactcct tatctcgcag cgcaaacctc aggcaactac aggtcctccc 4560
tgcacctttg aggtgcccct ccccccactc aaggttccag aaaaatccat gccctcggaa 4620
accccagaat cttactttcc cgaggcaccc caggacccca gggtcatcag ttcacagggc 4680
tgttagtgct cccataaaac tctagcctcc cagagggacc ccagccccca ccctcccgcc 4740
cacgaacccc tgcatttcca gaatcagccc cagggcccca acccccccaa gcccccattt 4800
cacaacacgc tggcgctaca ggcgcgtgac ttccccttgc tttggggcgg ggggctgaga 4860
ctcctatgtg ctccggattg gtcaggcacg gccttcggcc ccgcctcctg ccaccgcaga 4920
ttggccgcta gccctccccg agcgccctgc ctccgagggc cggcgcacca taaaagaagc 4980
cgccctagcc acgtcccctc gcagttcggc ggtcccgcgg gtctgtctct tgcttcaaca 5040
gtgtttggac ggaacagatc cggggactct cttccagcct ccgaccgccc tccgatttcc 5100
tctccgcttg caacctccgg gaccatcttc tcggccatct cctgcttctg ggacctgcca 5160
gcaccgtttt tgtggttagc tccttcttgc caaccaacca tgagctccca gattcgtcag 5220
aattattcca ccgacgtgga ggcagccgtc aacagcctgg tcaatttgta cctgcaggcc 5280
tcctacacct acctctctct ggtgagtccc caggacgccc ctggccctaa tttcctccag 5340
ctgcgcacct ccggccctca ctgcacgcgc cagccttctt tgtgcggtcg ggtaaacaga 5400
gggcggagtc cccttggcct cgcctcccgc taaccattgt tgcctccatc tcttcccgta 5460
gggcttctat ttcgaccgcg atgatgtggc tctggaaggc gtgagccact tcttccgcga 5520
attggccgag gagaagcgcg agggctacga gcgtctcctg aagatgcaaa accagcgtgg 5580
cggccgcgct ctcttccagg acatcaaggt aactagtgtg tgggtaatgg actacatctc 5640
ccagcaggcc gtgcgcgcga ggagccttga tttgagggcg taggtgtcgc gtgggcttct 5700
gggagattga gttcggtctt gtgagccctc ttaaccgctg gaaatagagg cgcacctcgt 5760
gcagtgccca caacacgcgg cagtccacac cgctgcgtgg tcttagggac gtatagctgt 5820
aagagctagg acagggtgcg gagagtgata aatacaagct gtcacatgtc tttgtggcct 5880
gggcctctga cccccaacga ctcttgggaa atgtaggttt agttctatgt gccgagtgtg 5940
tgtattctga gccatttctc ccttctatat agaagccagc tgaagatgag tggggtaaaa 6000
ccccagacgc catgaaagct gccatggccc tggagaaaaa gctgaaccag gccctttttgg 6060 atcttcatgc cctgggttct gcccgcacgg acccccatgt acgtacccgc tgcatccatg 6120
gctacccaac catacccctc aagcctctgc tccctttggg caaatttcct tcagagcctc 6180
atttcacacc tgtcacattt taatctgcaa ctggctgctc tctccccctc ttttccaggg 6240
attgggtttc taatttctcc ctcttctctc tcagctctgt gacttcctgg agactcactt 6300
cctagatgag gaagtgaagc ttatcaagaa gatgggtgac cacctgacca acctccacag 6360
gctgggtggc ccggaggctg ggctgggcga gtatctcttc gaaaggctca ctctcaagca 6420
cgactaagag ccttctgagc ccagcgactt ctgaagggcc ccttgcaaag taatagggct 6480
tctgcctaag cctctccctc cagccaatag gcagctttct taactatcct aacaagcctt 6540
ggaccaaatg gaaataaagc tttttgatgc agctggtggt tttgtgtgtg gtgtggaaga 6600
tgaggtggga tctgttctca taaagcttct ggctgggttg ggatgccagt gaaagaggag 6660
ttggccccat ctcccatttt cttaactgtc ctaagacaag aggctatctg ggtagtgttg 6720
aacctgaggg ttctctgctt gcctggctgt taactgtccc tcccagatgg tagagataga 6780
ctccagggag ttgaattaag acctaggttg gtatctagaa acagatgtta ggtctcagcc 6840
agaaacagcc ctatttaacg agtgattatg gggccaggtg ggtcgctcac ctgatgtcag 6900
gagttcgaga ccagcctgac caacatgaag aaaccccgtc tctactaaaa tacaaaatta 6960
gctgggtgtg gtggctcata cctgtaatcc cagctagtca ggaggttgag gtaggagaat 7020
cgcttgaatc tgggaggcgg aggttgcagt gagctgagat ggcgtcattg cactccagcc 7080
tgggcaaaaa gagtggaact cccatctcaa acaaaaaaca tgtctgcctc acggaagttg 7140
cggtgagctg agatggcgcc actgtgctcc agcttgggca acagagtaag actctgtctc 7200
aaaaaagaaa aaagcctcaa ttctgggagg cagttggaat tattaggccc tttatatggg 7260
cacattgacg ctattgctat gcaacttgca tggcaaccgg ggggctcact gaggtctttg 7320
ctccagagtt taagagatta tggcccgagc ttgagtgatc ccaatgtgag gcgcacactg 7380
agaggaactg gccagtggag ctgagcagcc aggaacacgt gatgcccaag caatgctgga 7440
caaggggttt agggttcatc acagaaatgg gatgtgaaac cttgggccgg attctccaaa 7500
tgggaactga agaagcttaa aacaggcctt aaaaagcact tgctgtgtcc aagctgcaaa 7560
actgctgtgt cagctctgac tcttcccctt ctccttcccc tgggtctggg gcagggtggt 7620
tcaagcctgt aatcccagca ctttgggagg ccaaggcagg acgatcactt gagcccagga 7680
ggttgagacc agcctaagca acatagggag accccccaag tctctctaga ataagaggat 7740
gagctcagac cagggaaggg gtggtactgg ggggacgtca cagccaggcc caccaagtgt 7800
catgtctgac cacacctggg attcttaaat atagatgtat ttttttcatc tcatctccgg 7860
acacactcca atcacacccc tcctgccctc ccctctcaac tgcaaaccaa gcggtgcaga 7920
cacagcacag cacacatgag gggccctccc tttcaccaaa gctgaaggca gggcacagtt 7980
tggggatgga agagcctcga ggtaaatgtg ggggttctag aacccagtga cctcagttct 8040
ggatcatggg aaagggatca gtatgcagta acgtggtaag gttccagatc tagaagccag 8100
gacctagaac ctagtggttt cacagtgggc agagcagttg ggaataagcc aggttagggg 8160
tgggggaaga cagccagctc tgtcctctgc aggcggattc cctggaggga gatctcagat 8220
ttagaaagga agagtaggat ctggtccaga aagggccaga aagacaggaa ggcatctgga 8280
ctgagactgt gtgtcctcca gaaggaatga gcagccaagt ggttctacca cctcttgctt 8340
ggccaaagtg taggggatga caggagccgg atggagggat cctccaggca gagcctggct 8400
ctgacatgcc agggagggct agaacatccc tcccagagcc ccacttctgg agttgaaatg 8460
gaggaccatc tgctctcagt taccttcaaa ctctgaaagt gccccggctc tggacttgat 8520
cgccccattc gcagggacac cacgtggttt ccagaacttg gtggcccgca t 8571

<210> SEQ ID NO 16
<211> LENGTH: 10376
<212> TYPE: DNA
<213> ORGANISM: Homo Sapiens

<400> SEQUENCE: 16
gcattcctgc acacacacat tccagcaaca cacttattaa acacacttac tgtatttaat 60
ggccatgcgg ggttccatca tgtgccctgt cctagttttc agcttgtgtt tcagccagtg 120
actctacggc tttgggcaag cctaaccttt tttgggtctc accttatctg taaaacatga 180
tgatttggaa gctctaacgt cctttccaaa gccttaaaat ttgtgggggg tctatgattt 240
cctagctgtg gatcctaaat tgtgactaca caataacaat ccctagaaga gaaagggacc 300

```
caacatctat tgagaattcc ccatgcggcg ggaaggcact gagcgaggga taggtaggaa    360
aagtgacacc taggcttgcc agcaaaaaca ccatcagagg cccccctgag tgatctcaga    420
cccctttgtt cccagtccgg cctctggact ttgtcccatt aggaaatggg gggaggggga    480
cactctccct ccctccctcc ctccctccct ccctccctcc acagtgaagc cacagccctc    540
caggtcttat gactgctctt ctcctccatg acaaagcact ttttgagccc aagcccagcc    600
tagcagagtg ctgagtcacg gtgggacagc aactctccac cgcaaccccc accaccgccc    660
cctcctgctc caggatgtgc tgaacctcca gaaaccaccg gcttggctct tctctcatct    720
gaggtccctc ccgccactcc tggccctggg aggcggctgt cctgggagac cagccaaact    780
ctctgctgcc tccaagtcac gaggagctga gctggagggt gggggaggta gaaccctggt    840
caacaaaggt cccaagacca ggccacagct tcggaagaat ctaaaggctt agacattgca    900
gttctgacac ctcaagttac cagaaagtag ggaacggaca caagcaatca tataaacaat    960
cataaacaca cacacacact cacactcccc caccaataga tttcccttcc attgttccca   1020
gccagcctcc tcccaatgac cttctacagc acaagctgtc cctcagtctt gctgcgatgt   1080
tcactgcagc tacatgcatg tttagccaag catggagcca acactgattc aggaaaccta   1140
ctccctgcag cagaccgact tccctccagt gggtccgaga gcttcatgct ggctttgtcc   1200
ccctggacat cccggaagcc tggaaactca gcacatctag tccaaaacca agcaggcctt   1260
ccccaagggc tttccccgaa accttcattt cctcctgtgc tccttggctc agggaatggc   1320
agcagcagcc aggcctacca aatcataaag ctgagagatc tcttacacac tgcccacccc   1380
tggcccccga ctttcgccaa tcagtctgtt catttgatct tctccagatc tgtcaaatct   1440
gtgttctatc ttctctgctc actaataact aaggctgctg cctcctgact ggtgcccagc   1500
cctctagcct cactctcatc catcctccac attcaatcat gaatccatct gttcatgcaa   1560
cagatactgg gcaccaagta acaagcaatt tgcaaaaagc tgggagtgca gagacaagac   1620
agaaacaatg cctgccttcc aggagcttac catctacagc accagcgcag gcaatcaaaa   1680
gggtctcata aggccaggtg cggtgggtca tgcctgtaat cccagcactt tgggaggccg   1740
aggcaggtgg atcacttgag gtcaggagtt cgagaccagc ctggccaaca tggtgaaacc   1800
ccgtctctat taaaaacaca aaaatcagcc aggtgtggtg gtaggcacct gtagtcccag   1860
ctacttggga ggctgtggca ggaggatctc ttgaacccgg gaggtggagg ttgcagtgag   1920
ccgagatcaa gccactgcac tccagcctgg gcaacaaggg caaaactcca tctcaaaaaa   1980
aaaggtgtga cacatacata gtacttcatt aaacatacaa atatatatta tagttcctaa   2040
tcttcatcac ttacatgagc tacaaatatc atcccaattt gtcatctctg ttttaacctt   2100
gtttacaaca tcttttgtct tacagctttt catttttaaa taggcaaacc tgccaactgt   2160
acttttacgg cttctgacag cctcagaaga acattcccta ccccaaaatt ataaaaataa   2220
tcttgtatat attcttctca aaactttata cttttttttaa ggcttggatt tttaatctat   2280
ctggaatgta tttttaaata ctgagtgagt cacttttctc cacatgactg tcaattgttt   2340
caacataatt tgttaaaccc attctttctt ccctaatgtg acacaacagt ttagcatata   2400
ccaagttctc ataatagggg ggcaggacta ttttgttgca ttaatctagt catctcttcc   2460
tgtgccagta ccatactgct tatagcactt tactgtacct ttattatagc accaaatgca   2520
aatctatcaa cacactgact cctccaaatg aactttagaa tcattttgtg aagtttcaaa   2580
aaaaaaaaaa atactgtccc agagacagta atggctgagg aaaaacaaaa acaaaaaact   2640
gcctcttatg gaaattgcag tgaatttatg cttatttggg gaaactgaca tctttacaga   2700
```

```
atgaagattg accgaccatt tgggaatatg gtacctcttc atttatgcta ggctttttga   2760
atttttgtc cagcagtaag catttatagt tttttctata tatttcttgt taactttatt   2820
ccaaggtact ttaagctttt gttgtcaatg taagtgaaaa acattttttt ttccattctt   2880
ttttccccat attttctaac tggtggttac tgttataaag gaaagctttg gatcctatat   2940
atggtgactt tgctatactc ttatcctaag agattcccag tgtaaggttt ctaaaaacaa   3000
agctaatgag gtgtctctat gctgtctcta ggatcaagtt taacctcttt ttatggaaca   3060
caaccctgcc cgatcttgcc cctattctcc accctaacca gcatccccca acataaactg   3120
tactttccag gccaacattc tttctttctt tcttttttt tttttttttt gagacggagt   3180
tttgttttgt cttccaggct ggagtgcaaa ggcgcgatct cggctcactg caacctccgc   3240
ctcccaggtt caagcgattc tcctgcctca gcctccagaa tagctaggat tacaggcgca   3300
tgccaccacg cccggctaat ttttgtattt tcagtagaga agggtttagc catgttagtt   3360
agccaggctg atctccaact ccgacctcaa gtgatccgcc cgcctcggcc tcccaaaatg   3420
ctgggattac aggcatgagc caccgcgccc agccccaggc aacatatttt cttaaggcag   3480
ctttaacagg ccatgcattt ccacatttcc acacctttgc atatgctgtt cactctgctc   3540
caaattccct tccctgtttc tctcccgcac ttcaccttcc ttttaacttt ttcttcaaac   3600
tcagctcacg tgtcttgctt agggagggct tccccgacct cctcctatcc cagactgggt   3660
aaggtactcc tggtctagca gcatccttct gtttacctta ttcttgtagc tctagcacca   3720
ctaaaacgtt tttcctgtaa ataacatagg tgcattttta aatgaaaccg tgaacaagaa   3780
atcaccctaa ttccgtcggc aatttatttt agtatttcag tagagttgct tttttaaact   3840
aaggtttgga agtctagctt ccagctgcag gtttgtgagc atcctgaaat tcagttcttc   3900
caccgatgcg tcaaaagacg cgacagaaca gtggacctcg aagccaggac ctaggtaagg   3960
gcagggccta gctctagctc tgccacccat aaattcacat ccaccctgtg cctgggactc   4020
agcttagcca cacacaccgg ccccacccct ccggggtctc tttcacctgt cacccgccat   4080
taaccccgtc agcttctctc caatgacacc ccagggttgt cctacagggc caccgaagcc   4140
tgaagctcct gtgagtgggg ccgataagag gccattttga aaagtcctca gcatgggctt   4200
cgcctttaga tccacgtcgt ttctcccttc taacccgaga tgtgtccctt gggtgcgaag   4260
cgacaccagc gattctctcg gaggccccgg tggctcaccc ccacgactcc ccggggaggc   4320
ggtccccatc cctagggaaa cccggcccgc ccagcctttg ttgcagaaac cgcacacgga   4380
gccatatttg ctttcagcca aaggcagacg tggtcggagg agtcggaagg gcaggggcgg   4440
acccgaaacc cgccgtgcgc cccacttctc catcgcgctc cttcctggac tctgaggaag   4500
agaaaatgcg ctcgaccacc taaggaccgc gtctccacct tccaccttcc caatcatctg   4560
cagcttccca atctgcagca aggtgtcaca agggcttctc cgcagctatg atttctaaca   4620
ccatgccccg ggccaggagc ctcagggtgc ccgttcggga aaatgggagc cgaatcagga   4680
tcaccccatg cgcccccgca cccttccccc gccggttcca acgcccgggc gcccctagac   4740
cggggggggg gttctgaggt ggacttcctg cgcctcctcg cagcttccct ccaactccac   4800
taaacgggca cagagacgcc accgctgtcc cagaggcagt cggctaccgg tccccgctcc   4860
cgagctccgc cagagcgcgc gagggcctcc agcggccgcc cctcccccac agcaggggcg   4920
gggtcccgcg cccaccggaa ggagcgggct cggggcgggc ggcgctgatt ggccggggcg   4980
ggcctgacgc cgacgcggct ataagagacc acaagcgacc cgcagggcca gacgttcttc   5040
```

```
gccgagagtc gtcggggttt cctgcttcaa cagtgcttgg acggaacccg gcgctcgttc   5100
cccaccccgg ccggccgccc atagccagcc ctccgtcacc tcttcaccgc accctcggac   5160
tgccccaagg cccccgccgc cgctccagcg ccgcgcagcc accgccgccg ccgccgcctc   5220
tccttagtcg ccgccatgac gaccgcgtcc acctcgcagg tgcgccagaa ctaccaccag   5280
gactcagagg ccgccatcaa ccgccagatc aacctggagc tctacgcctc ctacgtttac   5340
ctgtccatgg tgagcgcggg cgggcctaag cggtggcggg ggccgggcgc ggttcccggg   5400
gcgcgcgctg ggcgggccg ggggtgtggc cacccgcggg ctctcccgcc tccctgcgcc   5460
cttctggaaa atggaggctg ctcgaggttt ccgaggactt ctctggcgca gaaagtcggg   5520
gcagctggtt cttctcggct gtaccctgag aatgctccct cctaggccag ggccgcctct   5580
gcacaccctt ctttttaag gagaccttgg tgtcctgaaa tcctggggtt gcaagactgc   5640
cagcctgtgt gatcaatcct gcggttagga aggtggagtt ttgctttccc atcttttcct   5700
ctgcctccgg catttggccc taaatgccag cgtttttgc ttaggtatcc agctcccgtc   5760
cgcctgtgtg tggcggagct gctgggtaac ggtgtcgaat agcaaacctt gggggctggc   5820
gggaggtggc ttatcttgtg ggtagatccc tctcgagcag ccgtatccac ctctcggctc   5880
tgcttatctc taagtcccac ttgctttgaa gcatatctct aggaatcgcc ccttctgcag   5940
tcaccgaagt gtcacctgac cttgcgccta ggggacctaa tttatctttt atgtatctta   6000
ctgtaagagg tgtggagttt ggcctactaa ttgaaccccc agttcttgga taaagtccac   6060
cgacagttac tgggcaagaa atttttcagt gatcagtgga atcagttttc ccaaatcttg   6120
gtcttaggca gtgtcgtggg agtcttcctt agaattgcct tgtgattgtc caaactatcc   6180
caagaataaa tgtgttccaa atggatttga aaacaggcct gtatttctgt gactgtcact   6240
gcctttcaca aacacttgac tacatcaaat gtctaaaact gaaaatcaaa tttttgtgat   6300
ataactatta taaaagtatg tttacatcaa catactgtcc acatttgcca ccttgcatgg   6360
gggtttttaa tttgtgtgtg tgtgtgagag acagagtctc gctctgtcgc ccaggctgga   6420
gtgcagtggc gcgatctcgg ctcactgcag cctccgcctc ctgggttcaa gtgattctct   6480
tacctcaggc tcctgagtag ctggaattac aggcgcacgc caccacgccc agctattttt   6540
ttttattttt agtagagacg gggtttcacc atgttgacca ggatggtctc gatctgctga   6600
cctcgtgatc cgcctgcctc ggcctcccaa agtgctggga ttacaggctg agccaccgca   6660
cccagcaggg gtttttaatt ttataaataa atatgtggta cagctggcag actcctgagc   6720
tcagttttaa ccatgcttta acatggttaa tacaggagca gggaggagaa aaggactaag   6780
tgcagggtca gtactccagc gccctctcat cagacaatga attctgacac tggctgtaag   6840
ttttctgtgc agtaatacag atccttaaga cattgcccca ggcaatgccc ataatatcct   6900
aaaggttcct tgaagttaag tttcaaggat caagtttcag ttttctattt tagaatagaa   6960
acattactct tgggttcaat ccagtagctc atctgccccc cagtctcctt aggcactgat   7020
tccttcatgc tgtgctttga gaaaggaagc ctaggctgac gagaccatct tgcctccctg   7080
tagatcgtca cagctacctg tctctgggga tccctagtat aacacattca gtgttcccct   7140
ttcagtctta ctactttgac cgcgatgatg tggctttgaa gaactttgcc aaatactttc   7200
ttcaccaatc tcatgaggag agggaacatg ctgagaaact gatgaagctg cagaaccaac   7260
gaggtggccg aatcttcctt caggatatca aggtgaacaa aagatcctag ggtgtcata    7320
cttcatcatc tggcagtgtt cgggtatcag aaatcactta aactagcaat tgcccttata   7380
aagtgatgat acactgggct tttgcctttt gtgcttttt aggcttacca tctaaactaa    7440
```

```
attaggcaaa tagtaatgtc ccttttgcca aaacgtggtg gttagagatg atgggcttgc   7500
tgacttctag gttagttggt agagatgcat taacctattc tcattcagaa accagactgt   7560
gatgactggg agagcgggct gaatgcaatg gagtgtgcat tacatttgga aaaaaatgtg   7620
aatcagtcac tactggaact gcacaaactg gccactgaca aaaatgaccc ccatgtgagt   7680
attggaaccc caggaaataa atggaggaaa tcatttgcct tagggattgg gaaagctgcc   7740
cactaactgt cttccccatt gttttgcagt tgtgtgactt cattgagaca cattacctga   7800
atgagcaggt gaaagccatc aaagaattgg gtgaccacgt gaccaacttg cgcaagatgg   7860
gagcgcccga atctggcttg gcggaatatc tctttgacaa gcacaccctg ggagacagtg   7920
ataatgaaag ctaagcctcg ggctaatttc cccatagccg tggggtgact tccctggtca   7980
ccaaggcagt gcatgcatgt tggggtttcc tttacctttt ctataagttg taccaaaaca   8040
tccacttaag ttctttgatt tgtaccattc cttcaaataa agaaatttgg tacccaggtg   8100
ttgtctttga ggtcttggga tgaatcagaa atctatccag gctatcttcc agattcctta   8160
agtgccgttg ttcagttcta atcacactaa tcaaaaagaa acgagtattt gtatttatta   8220
aactcattag tttgggcagt atactaaggt gtggctgtct tggattcaga tagaactaag   8280
ggttcccgac tctgaatcca gagtctgagt taaatgtttc caatggttca gtctagcttt   8340
cacagttttt atgaataaaa ggcattaaag gctgaagtag tctgggattt ttatctatta   8400
agctaaccat ttgattcagg ctgttgtagg acatgttctt cagtgtggac agctgtatgg   8460
ctgtgactgg atcagtgtcc tgctggtgta cacacaggtg aggacctggc tggcgaagca   8520
tccccattag gaagcaggtt aggaatgtgc ttcatcccta gtgagaatga aagtattaac   8580
agcataagta tggaaggtcc cttcatttca aataccaaaa tgttgcagta ggagggcaaa   8640
ggttgagacg atcctttttt tttttttttt gagacagtct cactccgtcg cccaggctgg   8700
attgcagttg ctcaatctca ctgcaaccac cacctcctgg gttcaagcaa ttctcccctc   8760
aacctcctgc gttgggacta caggcacacc acgacgccca gctgatttgt attttttttg   8820
gtagagatgg ggtttcatca tgttggccag gttggtctca aactcctgac ctcctgtgat   8880
ccacttgcct ccacacccag cccaagacaa gattcttaaa tattaacatc ctttgctgaa   8940
caggccacag atgtttgcca agttcctgtc tagccctaga agcaagactg aaattgttgc   9000
ccttttaagt tttcaatcat aatagctgcg tgttctgacc gtgaaagtaa ctgcttgaga   9060
atccagaaaa gggaagttac acttcctccc acgtgattgg ggctgaagtg gggtgtttat   9120
aattgggtga aagtgtccag gaaatctgga ataaagggaa atatctgatt ttgtgacagc   9180
tttgggctga ccccaaggaa gcaagaagta ttttggtgag gttcccaggc agtgagaaaa   9240
tgacctaagg gcgctggaca ccctcaacct caccatctac cagttcctag gagtgaggca   9300
gttcctgcca ccctttcctg tagtgcttgg gtactaccct aaatagttat gggggaagtg   9360
ttcatctgtc atccagctga ctgccacctc atggttttgg gtcagccacc cttgctcaaa   9420
gtaagttggg gccagtgata acatctgctc agctaagcct ggcctgtcag ccctggggca   9480
gttctccagc agcattctgg tcagcacaac ctcatcttcc ttcacctggt cccaagaagt   9540
cttccgggtg ataccagggt gaagtgagaa aaggtcccga acacttccct aggatccctg   9600
tgaaggtggc caagtatata ccccaagcca gtgctgggcg taggtccagt gtgctctggc   9660
agtgatggaa ccctaggaaa ttgtggagga agggtaggct cagagcaagg gaagctgggg   9720
tggggcacag ggcaatgcag tgcccctggt tcaggtggag gacagacctg ttttccaagg   9780
```

```
cccaataagg atccatgtga tctttgagtg tagtgtgtat gttggttggt gattgttcca   9840

aaggttcttt gaggtgattt tcggggatct ctggcatatc cgtcaggtta aactccacag   9900

ttttcctcct cacttgagat acttctgggt gctccatcaa ggccccatcg ctctctgaga   9960

gcaattcaaa acttttcttg gccccagaac tcacagtctt taagcttttg tctttggtgt  10020

ctatgcctgt gacactgtga agctttgacg gcgctgatgg ttctaggggg aagaacatgg  10080

gagtggggct gaggggcgtc tgtggggcac tgtagtagcc tggcctctga tacagtgggg  10140

cagacttgaa ggcgtccaca gccttaagct tccaggcctt gttgtcttcc tggcccctaa  10200

cgttctgttt ggctgccttg tggtttttgg gcaggccctc gtggagaagg gattccctct  10260

tgggccacag tagtttggtc cttgagtttg ccctgggagg atggtgatca tgggactgca  10320

ggcctaggaa gcggccaatg atgccagcgt gagcatcctc ctcgtcctcc tgattg      10376
```

<210> SEQ ID NO 17
<211> LENGTH: 175
<212> TYPE: PRT
<213> ORGANISM: Homo sapiens

<400> SEQUENCE: 17

```
Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175
```

<210> SEQ ID NO 18
<211> LENGTH: 183
<212> TYPE: PRT
<213> ORGANISM: Homo sapiens

<400> SEQUENCE: 18

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
```

-continued

```
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180
```

EXPRESSION AND PURIFICATION OF RECOMBINANT HUMAN ISOFERRITINS USING A NOVEL EXPRESSION SYSTEM

CROSS REFERENCE TO RELATED APPLICATIONS

This Application is the National Phase entry under 35 U.S.C. § 371 of PCT International Application PCT/US2021/014473 filed Jan. 21, 2021, that claims the benefit of the filing date of U.S. Provisional Application No. 62/963,758 filed Jan. 21, 2020. The content of these earlier filed applications are hereby incorporated by reference herein in their entirety.

INCORPORATION OF THE SEQUENCE LISTING

The present application contains a sequence listing the content of which is hereby incorporated by reference.

FIELD OF THE INVENTION

The present disclosure is in the field of biotechnology and relates to the formation of one or more bioengineered ferritin proteins having a preselected ratio of H-subunits (ferritin heavy chain (FTH or H)) to L-subunits (ferritin light chain (FTL or L)). The disclosure further relates to cDNAs, vectors, and host cells for forming the bioengineered ferritin proteins of the present disclosure.

BACKGROUND

Ferritin is a unique molecule ideal for use in bionanotechnological applications as demonstrated by He and Marles-Wright in "Ferritin family proteins and their use in bio nanotechnology." N Biotechnol. (2015) and Jutz et al. in "Ferritin: A Versatile Building Block for Bio nanotechnology" Chem Rev. (2015). Ferritin is a major intracellular iron storage protein in prokaryotes and eukaryotes, including twenty-four subunits of heavy and light ferritin chains. Variation in ferritin subunit composition may affect the rates of iron uptake and release in different tissues. A major function of ferritin is the storage of iron in a soluble and nontoxic state.

Ferritin has a number of unique properties including high stability, easy purification, easy genetic manipulation, and self-assembly. Applications of ferritin may include: (i) fusion of targeting peptides at the N-terminus; (ii) insertion at exposed loop between D and E helix of immunogenic peptides (important in vaccines); (iii) fusion at the C-terminus for enzymes; (iv) the introduction of novel functions in a ferritin molecule; (v) insertion of an antigen per subunit to produce a bi-functional vaccine; (vi) modification of the metal binding site in the cavity and fusion of a targeting peptide on the surface; (vii) insertion of an antigen and an adjuvant; and (viii) fusion of an enzyme at an exposed N-terminus and a GFP site.

As a consequence of its unique properties and broad applicability, ferritin has been extensively studied in recent decades, however, the inventors have observed that is difficult and time consuming to synthesize heteropolymerferritin—with different ratios of FtH to FtL ("H:L"), from homopolymer ferritin using recombinant DNA technologies. In vitro reconstruction methods have attempted to do this by denaturing homopolymers under acidic or basic conditions, then re-assembling them by adjusting the solution's pH to a neutral value. However, the inventors have observed the re-naturation procedure used by in vitro methods problematically have very low recovery, reproducibility, and H:L ratio predictability. Moreover, in vitro reconstruction methods are tedious, produce low protein yield, and may introduce undesired modifications due to oxidation of subunit residues.

Accordingly, there is a continuing need in the art for improved methods for the synthesis of ferritin molecules, and production of ferritin molecules having variable ratios of H:L. For example, there is a continuing need for ferritin molecules having a predetermined or engineered ratio of H:L.

SUMMARY

The present disclosure provides bioengineered ferritin, such as recombinantly produced ferritin including a tuned or preselected ratio of H-subunits to L-subunits ("H:L"). In embodiments, the present disclosure provides a method for producing ferritin with a predefined ratio of ferritin heavy chain (FtH) to ferritin light chain (FtL), including: co-inserting a first cDNA sequence and a second cDNA sequence into a plasmid to construct a genetically modified plasmid; transforming the genetically modified plasmid into a host to form a genetically modified microbial host; and co-expressing a homopolymer ferritin molecule or a heteropolymer ferritin molecule at variable ratios of FtH to FtL, by exposing the genetically modified microbial host to a variable concentration of a first inducer and a variable concentration of a second inducer.

In embodiments, the present disclosure provides a method for producing ferritin with variable ratios of FtH to FtL subunits, including: forming a plasmid with a first cDNA sequence and a second cDNA sequence to produce a genetically modified plasmid capable of expressing ferritin molecule subunits at variable ratios; transforming the genetically modified plasmid into a bacterial host cell to form a genetically modified bacterial host; and exposing a genetically modified bacterial host to a variable concentration of a first inducer and second inducer to form a ferritin molecule at variable ratios of FtH to FtL.

In embodiments, the present disclosure includes a complementary deoxynucleotide (cDNA) sequence encoding an amino acid sequence having at least 90%, at least 95%, or at least 99% sequence identity to SEQ ID NO:17.

In embodiments, the present disclosure includes a complementary deoxynucleotide (cDNA) sequence encoding an amino acid sequence having at least 90%, at least 95%, or at least 99% sequence identity to SEQ ID NO:18.

In embodiments, the present disclosure includes a vector including a first complementary deoxynucleotide (cDNA) sequence encoding an amino acid sequence having at least 80%, at least 90%, at least 95%, or at least 99% sequence identity to SEQ ID NO:17, and a second complementary deoxynucleotide (cDNA) sequence encoding an amino acid sequence having at least 80%, at least 90%, at least 95%, or at least 99% sequence identity to SEQ ID NO:18.

In embodiments, the present disclosure includes a bacterial host cell including the vector of the present disclosure.

In embodiments, the present disclosure includes a complementary deoxynucleotide (cDNA) sequence including a nucleic acid sequence having at least 80% at least 90%, at least 95%, or at least 99% sequence identity to SEQ ID NO:2 or consisting of SEQ ID NO:2.

In embodiments, the present disclosure includes a complementary deoxynucleotide (cDNA) sequence including a nucleic acid sequence having at least 80% at least 90%, at least 95%, or at least 99% sequence identity to SEQ ID NO: 4, or consisting of SEQ ID NO:4.

In embodiments, the present disclosure includes a vector including a first complementary deoxynucleotide (cDNA) sequence including a nucleic acid sequence having at least 80% at least 90%, at least 95%, or at least 99% sequence identity to SEQ ID NO:2 or consisting of SEQ ID NO:2, and a second complementary deoxynucleotide (cDNA) sequence including a nucleic acid sequence having at least 80% at least 90%, at least 95%, or at least 99% sequence identity to SEQ ID NO:4 or consisting of SEQ ID NO: 4.

In embodiments, the present disclosure includes a bacterial host cell including the a vector including a first complementary deoxynucleotide (cDNA) sequence including a nucleic acid sequence having at least 80% at least 90%, at least 95%, or at least 99% sequence identity to SEQ ID NO:2 or consisting of SEQ ID NO:2, and a second complementary deoxynucleotide (cDNA) sequence including a nucleic acid sequence having at least 80% at least 90%, at least 95%, or at least 99% sequence identity to SEQ ID NO:4 or consisting of SEQ ID NO:4. In embodiments, the present disclosure includes recombinant ferritin protein formed in the bacterial host cell of the present disclosure, or by the methods of the present disclosure.

In some embodiments, the present disclosure relates to a bacterial host cell including one or more vectors of the present disclosure.

The illustrative aspects of the present disclosure are designed to solve the problems herein described and/or other problems not discussed.

BRIEF DESCRIPTION OF THE DRAWINGS

Non-limiting and non-exhaustive features will be described with reference to the following figures, wherein like reference numerals refer to like parts throughout the various figures. The figures below were not intended to be drawn to any precise scale with respect to size, angular relationship, or relative position.

FIG. 19 depicts an electrophoretic analysis, on 12% SDS PAGE, of ferritin expressed by various cell cultures at various inducer ratios.

FIGS. 20(A) and 20(B) depict electrophoretic analyses of ferritin expressed by a Rosetta-gami B cell culture, on 12% SDS PAGE and 7.5% Native PAGE respectively, comparing the formation of FtH and FtL at various inducer ratios.

Figure 1:
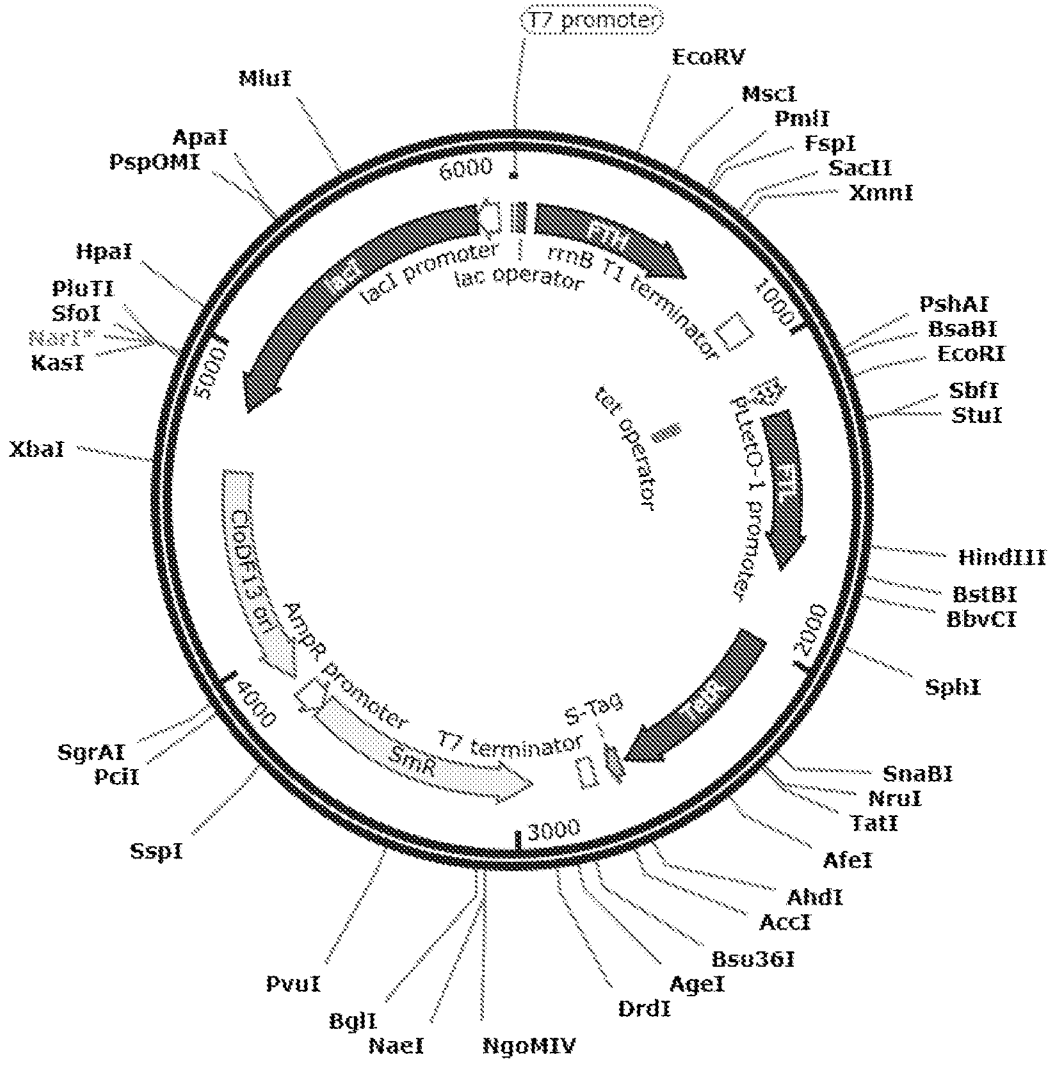
FIG. 1 depicts a software-generated plasmid map of the pWUR-FTH-tetO-FTL plasmid, a plasmid embodiment of the present disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

The present disclosure includes the formation of one or more bioengineered recombinant ferritin proteins having a preselected ratio of H-subunits (ferritin heavy chain (FTH)) to L-subunits (ferritin light chain (FTL)). More specifically, the present disclosure provides for expression of protein subunits in a bacterial host for assembly into a 3-D homo or heteropolymer protein, the genetic modification of plasmid vectors to optimize expression, and/or determining the appropriate bacterial host to optimize assembly. In embodiments, the present disclosure further relates to a genetic mechanism for expressing the Heavy-subunit ferritin gene sequences and Light-subunit ferritin gene sequences found in mammals, using multiple inducers and promoters, for subsequent assembly into 3-D homopolymer, or heteropolymer ferritin molecules with variable or preselected ratios of H-subunits to L-subunits. In embodiments, the present disclosure relates to recombinantly produced ferritin including a tuned or preselected ratio of H-subunits to L-subunits.

In embodiments, the present disclosure includes a method for producing ferritin with a predefined ratio of ferritin heavy chain (FtH) to ferritin light chain (FtL), including:

co-inserting a first cDNA sequence and a second cDNA sequence into a plasmid to construct a genetically modified plasmid; transforming the genetically modified plasmid into a host to form a genetically modified microbial host; and co-expressing a homopolymer ferritin molecule or a heteropolymer ferritin molecule at variable ratios of FtH to FtL, by exposing the genetically modified microbial host to a variable concentration of a first inducer and a variable concentration of a second inducer.

Ferritin was first described as readily crystallized protein in 1937. Ferritin is multimeric iron storage and detoxification protein present in prokaryotes, plants and animals, including 24 total subunits that assemble in a hollow shell. Individual subunits are poorly stable, however, when the subunits co-assemble, they form a highly stable ferritin nanostructure of about 8 nm inner diameter and 12 nm outer diameter capable of resisting temperatures up to 80° C. and resisting high concentrations of denaturing agents (e.g., urea).

Despite differences in the amino acid sequence of its subunits (See e.g., SEQ ID NO:17 the human amino acid sequences for ferritin light chain, and SEQ ID NO:18 for ferritin heavy chain), the 3-D structure of ferritin is conserved between animal species. The ferritin subunits are typically of 170 to 200 residues. Heavy ferritin subunits (i.e., H-subunits) have a mass of ~21,000 Da. Light ferritin subunits (i.e., L-subunits) have a mass of ~19,000 kDa. In embodiments, a residue may refer to a specific amino acid monomer within a polymeric chain of polypeptides that fold into a four-helical bundle, with a C-terminal fifth short helix at an acute angle with respect to the bundle.

In embodiments, ferritin is a homopolymer including, or consisting entirely of, one subunit. However, in some embodiments, one or more ferritin proteins include two subunits: (i) the H-subunit ("FtH"), and (ii) the L-subunit ("FtL"). In embodiments, FtH and FtL are provided in variable proportions or predetermined ratios.

In humans, separate FtH and FtL chains are encoded by distinct genes. See e.g., SEQ ID NO:15 which is a DNA sequence that encodes *Homo sapiens* ferritin light chain (FTL) located on chromosome 19, and SEQ ID NO:16 which is a DNA sequence that encodes *Homo sapiens* ferritin heavy chain (FTH) on located on chromosome 11. In embodiments, ferritin expression is tuned to include variable or preselected ratios of FtH to FtL depending on the specific need for expressing the ferritin molecule.

The primary biological function of ferritin is to sequester ferrous iron and induce mineralization. In principle, each subunit may carry a different function. In embodiments, heteropolymer ferritin molecules include two subunits having an independent but interrelated function: the ferroxidase of FtH and the Fe-nucleation of the FtL. The ferroxidase site of FtH is important for the mechanism of iron incorporation into the protein's interior cavity (in vitro and in vivo).

The FtH oxidizes iron and thus removes redox-active ferrous ions in cells and interacts with nuclear receptor coactivator 4 ("NCOA4") to facilitate ferritin degradation and cellular iron recycling. In contrast, the ferroxidase site of FtL is inactive due to the substitution of key amino acids. Furthermore, the FtL has an iron nucleation center that facilitates iron mineralization and deposition inside the ferritin hollow cavity.

In accordance with the present disclosure, a method for producing 24-mer heteropolymer ferritin molecules in various ratios of FtH subunits to FtL subunits is provided. In embodiments, a first process sequence includes providing a first cDNA sequence and a second cDNA sequence and co-inserting the first cDNA sequence and second cDNA, either stepwise or simultaneously, into a plasmid or vector to create a genetically modified plasmid or vector. In embodiments, a first cDNA sequence encodes a first ferritin subunit of the present disclosure, and the second cDNA sequence encodes a second ferritin subunit of the present disclosure. In embodiments, the subunits may be combined to form a 24-mer ferritin protein of the present disclosure. In a second process sequence a genetically modified microbial or bacterial host (such as *E. coli*) is formed by exposure to the genetically modified plasmid. In a third process sequence, co-expression of: 1) homopolymer; or 2) heteropolymer ferritin molecules is induced by exposing the genetically modified microbial host to various concentrations of a first inducer, such as 3-D-1 thiogalactopyranoside ("IPTG"), and a second inducer, such as tetracycline ("Tet"). As used herein, tetracycline or Tet may include any of a large group of antibiotics with a molecular structure containing four rings, or derivatives thereof such as derivatives suitable for tetracycline-controlled gene expression systems in bacteria. In embodiments, Tet may include anhydrotetracycline, which is a derivative of tetracycline that exhibits no antibiotic activity, however, may be used for tetracycline-controlled gene expression systems in bacteria.

In embodiments, the methods of the present disclosure produce ratios of FtH to FtL subunits, which correspond to different ratios of inducer concentrations. Non-limiting examples of concentration ratios and their corresponding average subunit ratios include: (I) 100 μM IPTG to 100 ng/ml Tet=21 FtH subunits to 3 FtL subunits; (II) 50-100 μM IPTG to 600 ng/ml Tet=21 FtH subunits to 3 FtL subunits; (III) 10 μM IPTG to 600 ng/ml Tet=9 FtH subunits to 15 FtL subunits; (IV) 10 μM IPTG to 800 ng/ml Tet=20 FtH subunits to 4 FtL subunits; (V) 20 μM IPTG to 800 ng/ml Tet=19 FtH subunits to 5 FtL subunits; (VI) 50 μM IPTG to 800 ng/ml Tet=21 FtH subunits to 3 FtL subunits; (VII) 100 μM IPTG to 800 ng/ml Tet=21 FtH subunits to 3 FtL subunits; (VIII) 10 μM IPTG to 1000 ng/ml Tet=6 FtH subunits to 18 FtL subunits; and (IX) 0 μM IPTG to 800-1200 ng/ml Tet=1 FtH subunits to 23 FtL subunits. In embodiments, a predetermined concentration ratio is selected for the formation of variable or predetermined ferritin proteins, such as having predetermined numbers of FtL and FtH subunits, for a total of 24 subunits.

By varying concentrations of inducers, such as e.g., isopropyl β-D-1 thiogalactopyranoside ("IPTG"), and tetracycline ("Tet"), the present disclosure advantageously provides efficient and cost-effective recombinant human ferritin production. Moreover, the present disclosure provides for synthesis of ferritin at any tuned or preselected ratio of H:L.

Definitions

As used in the present specification, the following words and phrases are generally intended to have the meanings as set forth below, except to the extent that the context in which they are used indicates otherwise.

As used herein, the singular forms "a", "an", and "the" include plural references unless the context clearly dictates otherwise. Thus, for example, references to "a compound" include the use of one or more compound(s). "A step" of a method means at least one step, and it could be one, two, three, four, five or even more method steps.

As used herein the terms "about," "approximately," and the like, when used in connection with a numerical variable, generally refers to the value of the variable and to all values of the variable that are within the experimental error (e.g., within the 95% confidence interval [CI 95%] for the mean) or within ±10% of the indicated value, whichever is greater.

cDNA: The term "complementary deoxynucleotide" or "cDNA" means a DNA molecule that can be prepared by reverse transcription from a mature, spliced, mRNA molecule obtained from a eukaryotic or prokaryotic cell. cDNA lacks introns or intron sequences that may be present in corresponding genomic DNA. In embodiments, cDNA may refer to a nucleotide sequence that correspond to the nucleotide sequence of an mRNA from which it is derived. In embodiments, cDNA refers to a double-stranded DNA that is complementary to and derived from mRNA.

The term "complementary" is used to describe the relationship between nucleotide bases that are capable of hybridizing to one another. For example, with respect to DNA, adenosine is complementary to thymine and cytosine is complementary to guanine.

"Codon degeneracy" refers to the property in the genetic code that permits variations in nucleotide sequence without resulting in the amino acid sequence of the encoded polypeptide. Those skilled in the art understand "codon bias" exhibited by a particular host cell when using nucleotide codons to identify a given amino acid. Therefore, in embodiments, when a gene is synthesized with the intention of improved expression in a host cell, it is desirable to design the gene so that its codon usage is close to the preferred codon usage of the host cell.

Coding sequence: The term "coding sequence" means a polynucleotide, which directly specifies the amino acid sequence of a polypeptide. The boundaries of the coding sequence are generally determined by an open reading frame, which begins with a start codon and ends with a stop codon. The coding sequence may be a genomic DNA, a cDNA, a synthetic DNA, or a combination thereof. In embodiments, "coding sequence" may refer to a DNA sequence that codes for a specific amino acid sequence. An "appropriate regulatory sequence" is located upstream (5' non-coding sequence), internal, or downstream (3' non-coding sequence) of the coding sequence, and transcription, RNA processing or stability, or translation of the associated coding sequence The term "expression" as used herein refers to the transcription and stable accumulation of sense (mRNA) or antisense RNA. Expression can also indicate translation of mRNA into a polypeptide.

As used herein the term "fragment" means a polypeptide having one or more amino acids absent from the amino and/or carboxyl terminus of a mature polypeptide or domain.

The term "isolated" means a substance in a form or environment that does not occur in nature. For example, an isolated polypeptide may include a polypeptide or a fragment, variant, or derivative thereof that is not in its natural milieu. No particular level of purification is required. For example, an isolated polypeptide can be removed from its native or natural environment. In embodiments, recombinantly produced polypeptides and proteins such as ferritin expressed in host cells are considered isolated for purposes of the present disclosure, as are native or recombinant polypeptides such as ferritin which have been separated, fractionated, or partially or substantially purified by any suitable technique.

As used herein, the terms "isolated nucleic acid fragment", "isolated nucleic acid molecule" and "gene construct" are used interchangeably and are optionally single-stranded or double-stranded with synthetic, non-natural or modified nucleotide bases. This will indicate a single-stranded RNA or DNA polymer. An isolated nucleic acid fragment in the form of a polymer of DNA can include one or more segments of cDNA, genomic DNA or synthetic DNA.

The term "operably linked" refers to a binding of nucleic acid sequences on a single nucleic acid fragment such that one function is affected by the other. For example, a promoter is operably linked to a coding sequence if it is capable of acting on the expression of the coding sequence (e.g., the coding sequence is under transcriptional control of the promoter). Coding sequences can be operably linked to regulatory sequences in sense or antisense orientation. In some embodiments the term "operably linked" means that the specified components are in a relationship permitting them to function in the intended manner, including but not limited to being contiguous. For example, a regulatory sequence is operably linked to a coding sequence such that expression of the coding sequence is under the control of the regulatory sequence.

The term "mature polypeptide" means a polypeptide in its final form following translation and any post-translational modifications. A "mature" protein refers to a post-translationally processed polypeptide, e.g., one from which any pre- or propeptides present in the primary translation product have been removed. "Precursor" proteins represent the primary product of translation of mRNA, i.e., where pre- and propeptides are still present. Pre- and propeptides can be, but are not limited to, intracellular localization signals.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology but is not necessarily translated from a designated nucleic acid sequence. It may be generated in any manner including by chemical synthesis.

"Promoter" refers to a DNA sequence capable of controlling the expression of a coding sequence or functional RNA. In general, a coding sequence is located 3' to a promoter sequence. A promoter can be derived from the native gene in its entirety, can include different elements from different promoters found in nature, or can further include a synthetic DNA segment. It is understood by those skilled in the art that different promoters can induce gene expression in different tissues or cell types, or at different stages of development, or in response to different environmental or physiological conditions. Promoters that cause gene expression almost always in most cell types are commonly referred to as "constitutive promoters". It is further understood that DNA fragments of different lengths can have the same promoter activity, since in most cases the exact boundaries of the regulatory sequences are not fully defined.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Percent identity can be readily determined by any known method, including but not limited to those described in: 1) Computational Molecular Biology (Lesk, A. M., Ed.) Oxford University: NY (1988); 2) Biocomputing: Informatics and Genome Projects (Smith, D. W., Ed.) Academic: NY (1993); 3) Computer Analysis of Sequence Data, Part I (Griffin, A. M., and Griffin, H. G., Eds.) Humana: NJ (1994); 4) Sequence Analysis in Molecular Biology (von Heinje, G., Ed.) Academic (1987); and 5) Sequence Analysis Primer (Gribskov, M. and Devereux, J., Eds.) Stockton: NY (1991), all of which are incorporated herein by reference. In embodiments, sequence identity between two amino acid sequences is determined using the Needleman-Wunsch algorithm (Needleman and Wunsch, 1970, J. Mol. Biol. 48: 443-453). In some embodiments, the degree of sequence identity refers to and may be calculated as described under "Degree of Identity" in U.S. Pat. No. 10,531,672 starting at Column 11, line 56. U.S. Pat. No. 10,531,672 is incorporated by reference in its entirety.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques. The term recombinant when used herein to characterize a polypeptide or protein sequence refers to a polypeptide or protein sequence encoded in whole or in part by recombinant DNA. In embodiments, the term "recombinant" when used in reference to a subject cell, nucleic acid, protein or vector indicates that the subject has been modified from its native state. Thus, for example, a recombinant cell expresses a gene that is not found within the native (non-recombinant) form of the cell, or expresses a native gene at a level that differs from the native level or under conditions that differ from those at which it naturally occurs. Recombinant nucleic acids may differ from the native sequence by one or more nucleotides and/or by being operably linked to a heterologous sequence, such as a heterologous promoter in an expression vector. In some embodiments, recombinant proteins may differ from the native sequence by one or more amino acids and/or by fusion with a heterologous sequence. In embodiments, a vector including nucleic acid encoding the ferritin of the present disclosure is a recombinant vector.

"RNA transcript" refers to the product resulting from RNA polymerase-catalyzed transcription of a DNA sequence. If the RNA transcript is a complete complementary copy of the DNA sequence, it is referred to as the primary transcript or it can be an RNA sequence derived from post-transcriptional processing of the primary transcript, referred to as mature RNA. The "Messenger RNA" or "mRNA" refers to RNA that resides within an intron and can be translated into protein by the cell.

The term "substantially purified," as used herein, refers to a component of interest that may be substantially or essentially free of other components which normally accompany or interact with the component of interest prior to purification. For example, a component of interest may be "substantially purified" when the preparation of the component of interest contains less than about 10%, less than about 5%, less than about 4%, less than about 3%, less than about 2%, or less than about 1% (by dry weight) of contaminating components. Thus, a "substantially purified" component of interest may have a purity level of about 90%, about 95%, about 96%, about 97%, about 98%, about 99% or greater.

"Transformation" refers to the transfer of a nucleic acid molecule into a host organism, resulting in a genetically stable genetic trait. The nucleic acid molecule can be, for example, a self-replicating plasmid or can be integrated into the genome of the host organism. Host organisms that have transformed nucleic acid fragments are referred to as "transgenic" or "recombinant" or "transformed" organisms.

In some embodiments, the terms "plasmid" and "vector" often carry genes that are not part of the cell's central metabolism and usually indicate extra chromosomal factors that take the form of circular double-stranded DNA fragments. Such factors can be self-replicating sequences, genomic integration sequences, phage, or linear or circular nucleotide sequences of single or double stranded DNA or RNA from any source, where multiple The nucleotide sequence has been ligated or recombined into a unique construct that can introduce the expression cassette into the cell.

The term "expression cassette" refers to regulatory sequences before (5' non-coding sequence) and after (3' non-coding sequence) the coding sequence of a selected gene and the coding sequence required for expression of the selected gene product. Thus, an expression cassette is typically composed of 1) a promoter sequence, 2) a coding sequence (i.e., ORF), and 3) a 3' untranslated region (i.e., a terminator) which usually has a polyadenylation site in eukaryotes. An expression cassette is usually contained within the vector to facilitate cloning and transformation. Different expression cassettes can be transformed into different organisms including bacteria, yeast, plants and mammalian cells as long as the correct regulatory sequences are used for each host.

A "selectable marker" or "selectable marker" refers to a gene that is capable of being expressed in a host cell to facilitate selection of the host cell harboring the gene. Examples of selectable markers include, but are not limited to, antimicrobial substances and/or genes that confer a metabolic advantage, such as a nutritional advantage to the host cell.

In some embodiments, the term "vector" refers to a polynucleotide sequence designed to introduce a nucleic acid into one or more cell types. Vectors include cloning vectors, expression vectors, shuttle vectors, plasmids, phage particles, cassettes, and the like.

An "expression vector" refers to a DNA construct including a DNA sequence encoding a polypeptide of interest, wherein the coding sequence is operably linked to suitable control sequences capable of effecting the expression of the DNA in a suitable host. Such control sequences may include a promoter to effect transcription, an optional operator sequence to control transcription, a sequence encoding a suitable ribosome binding site on the mRNA, an enhancer, and sequences which control termination of transcription and translation.

A "host strain" or "host cell" is an organism into which has been introduced an expression vector, phage, virus or other DNA construct, including a polynucleotide encoding a polypeptide of interest (e.g., ferritin). Exemplary host strains are microbial cells (e.g., bacteria) capable of expressing a polypeptide of interest. The term "host cell" includes protoplasts created from a cell.

The term "heterologous" with respect to a polynucleotide or protein refers to a polynucleotide or protein that is not naturally occurring in a host cell.

The term "endogenous" with respect to a polynucleotide or protein refers to a polynucleotide or protein that is naturally present in the host cell.

The term "expression" refers to the process of producing a polypeptide based on a nucleic acid sequence. The process includes both transcription and translation.

The terms "recovered", "isolated" and "isolated" refer to a compound, protein (polypeptide), cell, nucleic acid, amino acid, or other particular material or component that is removed from at least one other material or component with which it naturally occurs with which it is naturally associated. In embodiments, an "isolated" polypeptide thereof includes, but is not limited to, a culture broth comprising a secreted polypeptide expressed in a heterologous host cell. See U.S. patent publication no. 20160017305 (herein entirely incorporated by reference).

DESCRIPTION OF CERTAIN EMBODIMENTS

Embodiments of the present disclosure include a method for producing ferritin with a predefined ratio of ferritin heavy chain (FtH) to ferritin light chain (FtL), including: co-inserting a first cDNA sequence and a second cDNA sequence into a plasmid to construct a genetically modified plasmid; transforming the genetically modified plasmid into a host to form a genetically modified microbial host; and co-expressing a homopolymer ferritin molecule or a heteropolymer ferritin molecule at variable ratios of FtH to FtL, by exposing the genetically modified microbial host to a variable concentration of a first inducer and a variable concentration of a second inducer.

In embodiments, the present disclosure includes one or more DNA constructs including a nucleic acid encoding ferritin of the present disclosure which can be constructed for expression in a host cell. An example of a nucleic acid encoding one or more ferritin subunits in accordance with the present disclosure includes SEQ ID NO:2 and SEQ ID NO:4. Due to the well-known degeneracy of the genetic code, polynucleotide variants encoding the same amino acid sequence can be designed and prepared with routine skill. Moreover, it is possible to have several conservative alterations that do not change the amino acid sequence. Optimization of codons for a particular host cell is well known in the art. In embodiments, one or more nucleic acids encoding the amino acid sequence for ferritin of the present disclosure can be incorporated into a vector. The vectors may be transferred to host cells using well-known transformation techniques, such as those disclosed below.

In embodiments, a vector may be any vector which can be transformed into a host cell and replicated in the host cell. For example, a vector including a nucleic acid encoding an amino acid sequence having at least 90%, at least 95%, or at least 99% sequence identity to SEQ ID NO:17 and/or an amino acid sequence having at least 90%, at least 95%, or at least 99% sequence identity to SEQ ID NO:18 can be transformed and replicated in a bacterial host cell as a means of propagating and amplifying the vector. In another example, a vector including a nucleic acid sequence having at least 90%, at least 95%, or at least 99% sequence identity to SEQ ID NO:2 and/or nucleic acid sequence having at least 90%, at least 95%, or at least 99% sequence identity to SEQ ID NO:4 can be transformed and replicated in a bacterial host cell as a means of propagating and amplifying the vector.

One or more vectors of the present disclosure may also be transformed into an expression host such that the encoding nucleic acid is expressed as a functional ferritin, or functional ferritin subunit. Host cells that serve as expression hosts may include, for example, bacteria cells such as *E. Coli*, or a strain of *E. coli*. such as Rosetta-gami B, or BL21 (DE3) pLys. A non-limiting example of a vector of the present disclosure is shown in FIG. 1, which is suitable for use in *E. Coli*.

In embodiments, one or more nucleic acid encoding ferritin subunits of the present disclosure can be operably linked to one or more suitable promoters that allows transcription in a host cell. The promoter may be any DNA sequence which shows transcriptional activity in the host cell of choice and may be derived from genes encoding proteins either homologous or heterologous to the host cell in question. Exemplary promoters for directing transcription of a DNA sequence encoding ferritin of the present disclosure or ferritin subunits of the present disclosure, particularly in a bacterial host, are the promoter of the lac operon of *Escherichia coli* (*E. coli*), and/or a T7 promoter. Exemplary promoters are also shown in FIG. 1 of the present disclosure.

In some embodiments, an expression vector suitable for use herein may also include one or more suitable transcription terminators.

In embodiments, a vector may further include a DNA sequence enabling the vector to replicate in a host cell. Examples of such a sequence include an origin of replication of plasmids such as pUC19.

In embodiments, the vector may also include a selectable marker, e.g., such as a gene which confers antibiotic resistance (such as, for example, ampicillin resistance).

Intracellular expression may be advantageous in some aspects, for example, when certain bacteria are used as host cells to produce large quantities of ferritin of the present disclosure for subsequent enrichment or purification. Extracellular secretion of ferritin of the present disclosure into culture medium can also be used to produce cultured cellular material including the isolated ferritin of the present disclosure.

In embodiments, an expression vector may also include components of a cloning vector such as, for example, elements that allow autonomous replication of the vector in the selected host organism and one or more markers detectable on the phenotype for selection purposes. In embodiments, an expression vector may include one or more control nucleotide sequences such as a promoter, operator, ribosome binding site, transcription initiation signal, or a repressor gene or one or more activator genes. In embodiments, for expression under the direction of a control sequence, the one or more nucleic acid sequences of the ferritin of the present disclosure may be operatively linked to a control sequence in a manner that is correct with respect to expression.

Methods for ligating ferritin-encoding DNA constructs, promoters, terminators and other elements, respectively, and inserting them into suitable vectors containing information required for replication are well known to those skilled in the art (see, e.g., Sambrook et al, Molecular Cloning: A Laboratory Manual, second edition, Cold Spring Harbor, 1989, and third edition, 2001). Embodiments, of the present disclosure include standard recombinant DNA and molecular cloning techniques that are well known in the art and are described in Sambrook J. et al. Fritsch E.; F. And Maniatis T. "Molecular Cloning: A Laboratory Manual", 2nd edition, Cold Spring Harbor Laboratory (Cold Spring Harbor, NY) (1989) (hereinafter "Maniatis"); J. et al. Bennan M.; L. And Enquist L. W. "Experiments with Gene Fusions," Cold Spring Harbor Laboratory (Cold Spring Harbor, NY) (1984); and Ausubel F. M. M. Et al., "Current Protocols in Molecular Biology", Green Publishing Assoc. and Wiley Interscience (Hoboken, NJ) (1987) "An Overview: Microbiology of Fatty Acids and Triacylylylols". See e.g., U.S. Pat. No. 8,735,108 herein incorporated entirely by reference. In some embodiments, nucleic acids and expression vectors can be generated via methods known per se for modifying nucleic acids. Such methods are, for example, presented in relevant manuals such as the one by Fritsch, Sambrook and Maniatis, "Molecular cloning: a laboratory manual", Cold Spring Harbor Laboratory Press, New York, 1989, and familiar to a person skilled in the art in the field of biotechnology. Examples of such methods are chemical synthesis or the polymerase chain reaction (PCR), optionally in conjunction with further standard methods in molecular biology and/or chemistry or biochemistry.

In embodiments, a bacterial host cell including an expression vector according to the present disclosure is provided. In embodiments, an expression vector is introduced into the host cell by the transformation thereof. For example, transforming a vector according to the present disclosure into a microorganism, which then constitutes a host cell according to the present disclosure. Alternatively, it is also possible for individual components, i.e., nucleic acid portions or fragments, for example the components of a vector according to the present disclosure to be introduced into a host cell in such a way that the thus resulting host cell includes a vector according to the present disclosure.

Methods for transforming cells are established in the prior art and well known to a person skilled in the art. In embodiments, prokaryotic cells, are suitable as host cells as they can be advantageously manipulated genetically, for example with regard to transformation with the vector and the stable establishment thereof. In addition, host cells may be easily manipulatable from a microbiological and biotechnological perspective, for example, ease of culture, high growth rates, low demands on fermentation media, and good production for foreign proteins.

In embodiments, host cells are prokaryotic or bacterial cells. Non-limiting examples of suitable host cells include host cell selected from the group of the genera of *Escherichia*. In embodiments, the host cells can be modified with respect to their requirements in terms of culture conditions, can have other or additional selection markers, antibiotic selection marker(s), or can express other or additional proteins. More particularly, the host cells can be those which express multiple proteins or polypeptides.

In embodiments, the host cells are cultured and fermented in a manner known in the art, for example in batch systems or continuous systems. In some embodiments, host cells are used to prepare proteins encoded by the nucleic acid sequence encoding ferritin polypeptides or subunits thereof in accordance with the present disclosure. The disclosure therefore further provides a method for producing a ferritin of the present disclosure in a bacterial host cell, the method including: transforming one or more bacterial host cells with an expression vector including a nucleotide sequence encoding ferritin of the present disclosure; and culturing the transformed bacterial host cells in a medium suitable for expression of the ferritin of the present disclosure. In embodiments, the host cell may be cultured under suitable conditions that allow for expression of the ferritin and/or ferritin subunits H, L, alone or in combination. In embodiments, production is characterized as inducible, and/or requiring stimulation to elicit expression. For inducible expression, protein production can be initiated when desired, for example by adding one or more, such as two inducer substances (e.g., isopropyl β-D-1 thiogalactopyranoside ("IPTG"), or a member of the antibiotic group of tetracyclines, tetracycline compound or derivative thereof) to the culture medium, and ferritin polypeptides and/or subunits (H, L) of the present disclosure can also be produced recombinantly. In embodiments, a first inducer is isopropyl β-D-1 thiogalactopyranoside ("IPTG"). In embodiments, a second inducer is a member of the antibiotic group of tetracyclines, and/or a tetracycline compound or derivative thereof such as anhydrotetracycline. In embodiments, a variable concentration of the first inducer, such as from 0-100 μM, or 0.5-100 μM and a variable concentration of the second inducer, from 100-1200 ng/ml, produce variable ratios of FtH to FtL. In embodiments, a variable concentration of the first inducer, such as from 10-75 μM, or 20-50 μM and a variable concentration of the second inducer, from 150-1000 ng/ml, or 350-800 ng/ml produce variable ratios of FtH to FtL. In embodiments, different concentrations within specific ranges of inducer concentration ratios, of the first inducer to the second inducer, will produce corresponding distinct average subunit ratios of FtH to FtL. In embodiments, the concentration ratio of the first inducer to the second inducer is: 100 μM to 100 ng/ml, which produces the corresponding average subunit ratio of 21 FtH subunits to 3 FtL subunits; 50-100 μM to 600 ng/ml, which produces the corresponding average subunit ratio of 21 FtH subunits to 3 FtL subunits; 10 μM to 600 ng/ml, which produces the corresponding average subunit ratio of 9 FtH subunits to 15 FtL subunits; 10 μM to 800 ng/ml, which produces the corresponding average subunit ratio of 20 FtH subunits to 4 FtL subunits; 20 μM to 800 ng/ml, which produces the corresponding average subunit ratio of 19 FtH subunits to 5 FtL subunits; 50 μM to 800 ng/ml, which produces the corresponding average subunit ratio of 21 FtH subunits to 3 FtL subunits; 100 μM to 800 ng/ml, which produces the corresponding average subunit ratio of 21 FtH subunits to 3 FtL subunits; 10 μM to 1000 ng/ml, which produces the corresponding average subunit ratio of 21 FtH subunits to 3 FtL subunits; or 0 μM to 800-1200 ng/ml, which produces the corresponding average subunit ratio of 1 FtH subunits to 23 FtL subunits.

In embodiments, the present disclosure includes a method for producing ferritin (or subunits thereof) with a predefined ratio of ferritin heavy chain (FtH) to ferritin light chain (FtL), including: co-inserting a first cDNA sequence and a second cDNA sequence into a plasmid to construct a genetically modified plasmid; transforming the genetically modified plasmid into a host to form a genetically modified microbial host; and co-expressing a homopolymer ferritin molecule or a heteropolymer ferritin molecule at variable ratios of FtH to FtL, by exposing the genetically modified microbial host to a variable concentration of a first inducer and a variable concentration of a second inducer. In embodiments, the microbial host is a bacterial host. In embodiments, the bacterial host is a strain of *E. coli*. In embodiments, the strain of *E. coli* is Rosetta-gami B, or BL21 (DE3) pLys. In embodiments, the first cDNA sequence comprises or consisting of SEQ ID NO:2 and the second cDNA sequence comprises or consists of SEQ ID NO:4, or a first cDNA sequence having at least 95% sequence identity to SEQ ID NO:2 and a second cDNA sequence having at least 95% sequence identity to SEQ ID NO:4. In embodiments, a first inducer is isopropyl β-D-1 thiogalactopyranoside ("IPTG"). In embodiments, the second inducer is a member of the antibiotic group of tetracyclines or derivatives thereof. In embodiments, the second inducer is a tetracycline compound or derivative thereof such as anhydrotetracycline. In embodiments, a variable concentration of the first inducer, from 0-100 μM or 0.5-100 μM, and a variable concentration of the second inducer, from 100-1200 ng/ml, produce variable ratios of FtH to FtL. In embodiments, different concentrations within specific ranges of inducer concentration ratios, of the first inducer to the second inducer, will produce corresponding distinct average subunit ratios of FtH to FtL.

In some embodiments, the concentration ratio of the first inducer to the second inducer is: 100 μM to 100 ng/ml, which produces the corresponding average subunit ratio of 21 FtH subunits to 3 FtL subunits; 50-100 μM to 600 ng/ml, which produces the corresponding average subunit ratio of 21 FtH subunits to 3 FtL subunits; 10 μM to 600 ng/ml, which produces the corresponding average subunit ratio of 9 FtH subunits to 15 FtL subunits; 10 μM to 800 ng/ml, which produces the corresponding average subunit ratio of 20 FtH subunits to 4 FtL subunits; 20 μM to 800 ng/ml, which produces the corresponding average subunit ratio of 19 FtH subunits to 5 FtL subunits; 50 μM to 800 ng/ml, which produces the corresponding average subunit ratio of 21 FtH subunits to 3 FtL subunits; 100 μM to 800 ng/ml, which produces the corresponding average subunit ratio of 21 FtH subunits to 3 FtL subunits; 10 μM to 1000 ng/ml, which produces the corresponding average subunit ratio of 21 FtH subunits to 3 FtL subunits; or 0 μM to 800-1200 ng/ml, which produces the corresponding average subunit ratio of 1 FtH subunits to 23 FtL subunits.

In some embodiments, the first cDNA sequence and the second cDNA are in are co-inserted simultaneously. In some embodiments, a simultaneous co-insertion is carried out via Gibson Assembly. In embodiments, the first cDNA sequence and the second cDNA sequences are co-inserted stepwise. In some embodiments, the stepwise co-insertion is carried out via heatshock or electroporation.

In embodiments, the present disclosure includes a method for producing ferritin with variable ratios of FtH to FtL subunits, including: forming a plasmid with a first cDNA sequence and a second cDNA sequence to produce a genetically modified plasmid capable of expressing ferritin molecule subunits at variable ratios; transforming the genetically modified plasmid into a bacterial host cell to form a genetically modified bacterial host; and exposing a genetically modified bacterial host to a variable concentration of a first inducer and second inducer to form a ferritin molecule at variable ratios of FtH to FtL. In embodiments, the bacterial host is a strain of *E. coli*. In embodiments, the first inducer is isopropyl β-D-1 thiogalactopyranoside ("IPTG"), and the second inducer is a member of the antibiotic group of tetracyclines or derivative thereof. In embodiments, the second inducer is an anhydrotetracycline compound.

In some embodiments, the present disclosure includes a complementary deoxynucleotide (cDNA) sequence encoding an amino acid sequence having at least 80 at least 90%, at least 95%, or at least 99% sequence identity to SEQ ID NO:17. In some embodiments, the present disclosure includes a complementary deoxynucleotide (cDNA) sequence encoding an amino acid sequence comprising or consisting of SEQ ID NO:17.

In some embodiments, the present disclosure includes a complementary deoxynucleotide (cDNA) sequence encoding an amino acid sequence having at least 80% at least 90%, at least 95%, or at least 99% sequence identity to SEQ ID NO:18. In some embodiments, the present disclosure includes a complementary deoxynucleotide (cDNA) sequence encoding an amino acid sequence comprising or consisting of SEQ ID NO:18.

In some embodiments, the present disclosure includes a vector including a first complementary deoxynucleotide (cDNA) sequence encoding an amino acid sequence having at least 80% at least 90%, at least 95%, or at least 99% sequence identity to SEQ ID NO:17, and a second complementary deoxynucleotide (cDNA) sequence encoding an amino acid sequence having at least 80%, at least 90%, at least 95%, or at least 99% sequence identity to SEQ ID NO:18. In some embodiments, the present disclosure includes a bacterial host cell including a vector of the present disclosure.

In some embodiments, the present disclosure includes a complementary deoxynucleotide (cDNA) sequence comprising a nucleic acid sequence having at least 80%, at least 90%, at least 95%, or at least 99% sequence identity to SEQ ID NO:2. In some embodiments, the present disclosure includes a complementary deoxynucleotide (cDNA) sequence comprising a nucleic acid sequence having at least 80%, at least 90%, at least 95%, or at least 99% sequence identity to SEQ ID NO:4. In some embodiments, the present disclosure includes a complementary deoxynucleotide (cDNA) sequence comprising a nucleic acid sequence from humans (H, L), mouse (H, L), and frog (H, M). In embodiments, Mouse L has about 83% percent identity to the human nucleic acid encoding L. In embodiments, Mouse H has about 93% percent identity to the human nucleic acid encoding H.

In embodiments, the present disclosure includes a vector including a first complementary deoxynucleotide (cDNA) sequence including a nucleic acid sequence having at least 80%, at least 90%, at least 95%, or at least 99% sequence identity to SEQ ID NO:2, and a second complementary deoxynucleotide (cDNA) sequence including a nucleic acid sequence having at least 80%, at least 90%, at least 95%, or at least 99% sequence identity to SEQ ID NO:4. In embodiments, the present disclosure includes a vector including a first complementary deoxynucleotide (cDNA) sequence comprising or consisting of SEQ ID NO:2, and a second complementary deoxynucleotide (cDNA) sequence comprising a or consisting of SEQ ID NO:4. In embodiments, the present disclosure includes a bacterial host cell including these vectors or vectors of the present disclosure.

The present disclosure also includes a recombinant ferritin protein formed in the bacterial host cell of the present disclosure. In embodiments, the recombinant ferritin has preselected ratios of FtH to FtL. In some embodiments, the ferritin of the present disclosure includes 24 subunits consisting of FtH. In some embodiments, the ferritin of the present disclosure includes 24 subunits consisting of FtL. Accordingly, homopolymers may be formed by the methods of the present disclosure.

In some embodiments, the ferritin of the present disclosure includes 24 subunits including: 24 subunits of FtH and 0 subunit of FtL, 23 subunits of FtH and 1 subunit of FtL, 22 subunits of FtH and 2 subunit of FtL, 21 subunits of FtH and 3 subunit of FtL, 20 subunits of FtH and 4 subunit of FtL, 19 subunits of FtH and 5 subunit of FtL, 18 subunits of FtH and 6 subunit of FtL, 17 subunits of FtH and 7 subunit of FtL, 16 subunits of FtH and 8 subunit of FtL, 15 subunits of FtH and 9 subunit of FtL, 14 subunits of FtH and 10 subunit of FtL, 13 subunits of FtH and 11 subunit of FtL, 12 subunits of FtH and 12 subunit of FtL, 11 subunits of FtH and 13 subunit of FtL, 10 subunits of FtH and 14 subunit of FtL, 9 subunits of FtH and 15 subunit of FtL, 8 subunits of FtH and 16 subunit of FtL, 7 subunits of FtH and 17 subunit of FtL, 6 subunits of FtH and 18 subunit of FtL, 5 subunits of FtH and 19 subunit of FtL, 4 subunits of FtH and 20 subunit of FtL, 3 subunits of FtH and 21 subunit of FtL, 2 subunits of FtH and 22 subunit of FtL, 1 subunits of FtH and 23 subunit of FtL, 0 subunits of FtH and 24 subunit of FtL.

In some embodiments, the ferritin of the present disclosure includes 24 subunits including: 23 subunits of FtH and 1 subunit of FtL, 22 subunits of FtH and 2 subunit of FtL, 21 subunits of FtH and 3 subunit of FtL, 20 subunits of FtH and 4 subunit of FtL.

In some embodiments, the ferritin of the present disclosure includes 24 subunits including: 19 subunits of FtH and 5 subunit of FtL, 18 subunits of FtH and 6 subunit of FtL, 17 subunits of FtH and 7 subunit of FtL, 16 subunits of FtH and 8 subunit of FtL, 15 subunits of FtH and 9 subunit of FtL, 14 subunits of FtH and 10 subunit of FtL.

In some embodiments, the ferritin of the present disclosure includes 24 subunits including:13 subunits of FtH and 11 subunit of FtL, 12 subunits of FtH and 12 subunit of FtL, 11 subunits of FtH and 13 subunit of FtL.

In some embodiments, the ferritin of the present disclosure includes 24 subunits including: 10 subunits of FtH and 14 subunit of FtL, 9 subunits of FtH and subunit of FtL, 8 subunits of FtH and 16 subunit of FtL.

In some embodiments, the ferritin of the present disclosure includes 24 subunits including: 7 subunits of FtH and 17 subunit of FtL, 6 subunits of FtH and 18 subunit of FtL, 5 subunits of FtH and 19 subunit of FtL, 4 subunits of FtH and 20 subunit of FtL, 3 subunits of FtH and 21 subunit of FtL, 2 subunits of FtH and 22 subunit of FtL, 1 subunits of FtH and 23 subunit of FtL, 0 subunits of FtH and 24 subunit of FtL.

In embodiments, since it is possible to preselect the ratio of subunits of the present disclosure, it is possible to deselect undesirable 24-mer ferritin proteins should particular ferritin proteins be undesirable for a particular study or experiment. For example, if a study or protocol wanted to exclude the formation of the ferritin of the present disclosure having 24 subunits including: 12 subunits of FtH and 12 subunit of FtL, the concentration of the one or more inducers may be preselected to preclude formation of a ferritin of the present disclosure having 24 subunits including: 12 subunits of FtH and 12 subunit of FtL. This is true for any particular isoferritin should formation thereof become undesirable or unwanted. Accordingly, it is possible to exclude one or more particular species and/or further tune the characteristics of desired isoferritin.

In embodiments, a recombinant ferritin protein is made by the methods of the present disclosure. In embodiments, ferritin of the present disclosure is isolated and/or substantially purified.

ADDITIONAL EMBODIMENTS

In embodiments, FtH rich ferritin may be useful in the study of Neuroferritinopathy ("NF"), a rare genetic neurodegenerative disorder. NF is caused by heterogeneous nucleotide insertions at the C-terminus of the FtL, which alters the sequence and folding of the C-terminus. It was shown that the presence of 2 or 3 mutant pathogenic FtL per 24-mer ferritin is sufficient to alter the permeability of the ferritin shell, thereby reducing the capacity to accumulate and store iron. This result partially explains the brain iron excess condition characteristic of NF patients.

However, there is a continuing need to express heteropolymer ferritin molecules in *E. coli*, and excellent research value for a method to synthesize heteropolymer ferritin at specific H:L ratios, and/or express ferritin molecules with distinct proportions of the two ferritin subunits.

Thus, synthesis of ferritin molecules—at various ratios of ferritin subunits—is a priority in the field because it facilitates studying animal cells, tissues, and organs. Furthermore, the study of heteropolymer ferritins may confer unique features, such as iron core structure, nanomaterial synthesis, iron uptake, and iron mobilization processes that may occur in homopolymer ferritins.

Given the foregoing, the development of an improved ferritin synthesis system capable of manufacturing large quantities of heteropolymer ferritin has independent value. While such a system in which the specific ratio of H:L is controllable and capable of reproducing molecules across the entire spectrum of ferritin subunit ratios has even greater valuable.

The approach to heteropolymer ferritin synthesis described herein enables the expression of FtH and FtL under the control of their respective inducible promoters within the same vector. The dual promoter method allows for transcription to be differentially induced.

Constructing the pWUR-FtH-tetO-FTL Plasmid of the Present Disclosure

In embodiments, a vector—pWUR-FtH-tetO-FtL as shown in FIG. 1—is suitable for use in accordance with the present disclosure. This vector contains 7,356 base pairs (distributed by Addgene as plasmid #80102). Addgene plasmid #80102 was acquired because its Cas1-Cas2 wild type proteins, and their inactive mutants, are independently induced.

Addgene plasmid #80102 was modified using the Gibson Assembly technology, by inserting two ferritin chains together, the FtH and the FtL. Each chain is expressed under a different promoter. In principle, this allows production of homopolymer FtH ferritin, FtL ferritin, and heteropolymer ferritin with variable subunit ratios.

The pWUR-FtH-tetO-FtL vector of 7,365 base pairs contains the wild type Cas1 and Cas2 protein-coding genes. The Cas1 and Cas2 genes are separated by a nucleotide (A) followed by an intervening sequence containing: the (i) rrnB T1 terminator, the (ii) Tet operator, and the (iii) PLtetO-1 promoter; which are followed by the mutant Cas1 and Cas2 gene sequences.

In embodiments, the method claimed herein replaces the wild type and mutant Cas1 and Cas2 gene sequences with the gene sequences that code for the ferritin FtH and the ferritin FtL genes. In embodiments, the cDNA of the human ferritin FtH is substituted for that of the Cas1 and Cas2 wild type proteins. In embodiments, the cDNA of the human ferritin FtL is substituted for that of the inactive Cas1 and Cas2 mutants.

In embodiments, instead of using the normal cloning procedure, which is comprised of at least two separate cloning steps, embodiments utilized the Gibson Assembly technology that enables the assembly of multiple DNA fragments with compatible termini in one step. The Gibson Assembly method is facilitated by: (i) the availability of a program that designs the assembly and the primers to produce the fragments by PCR (NEB building); and (ii) a Gibson master mix that contains the enzymes and buffers necessary for the assembly.

In embodiments, the system requires that the DNA fragments contain approximately 20 to 40 base pair overlap with adjacent DNA fragments. The fragments are combined with a mixture of three enzymes and other buffer components. The enzymes include: (1) an exonuclease to remove DNA from the 5' terminus to expose protruding complementary 3' ends; (2) a DNA polymerase to fill the gaps; and (3) a ligase to seal the nicks.

In embodiments, the construction involved the assembly of 4 DNA fragments: (1) covering all the pWUR plasmid without the Cas genes and intervening sequence; (2) the H-ferritin such as H-ferritin cDNA; (3) the intervening sequence; and (4) the L-ferritin such as L-ferritin cDNA.

Fragment (1) and (3) were produced by PCR using the pWUR 1+2 tetO mut89 plasmid as template.

Fragment (2) and (4) were produced by PCR using a previously constructed templated plasmid named pASK-FTH-T7-FTL.

```
To produce a fragment of 4,593 base pairs,
the primers for fragment(1) are:
Forward:
                                  (SEQ ID NO: 6)
AGCCTTAATTAACGGCACTCC

Reverse:
                                  (SEQ ID NO: 7)
GGTATATCTCCTTATTAAAGTTAAAC

To produce a fragment of 558 base pairs,
the primers for fragment (2) were:
Forward:
                                  (SEQ ID NO: 8)
CTTTAATAAGGAGATATACCATGGCTAGCACGACCGCG

Reverse:
                                  (SEQ ID NO: 9)
CCGCGGCCGCTTAGCTTTCATTATCACTGTCTCCCAGG.

To produce a fragment of 520 base pairs,
the primers for fragment (3) were:
Forward:
                                 (SEQ ID NO: 10)
TGAAAGCTAAGCGGCCGCGGCTGTTTTG

Reverse:
                                 (SEQ ID NO: 11)
GGGAGCTCATATGTATATCTCCTTCTTAA

AGTTAAATTTAATGAATTCGGTCAGTGCG

To produce a fragment of 528 base pairs,
the primers for fragment (4) were:
Forward:
                                 (SEQ ID NO: 12)
AGATATACATATGAGCTCCCAGATTCGTC

Reverse:
                                 (SEQ ID NO: 13)
GAGTGCCGTTAATTAAGGCTTTAGTCGTGCTTGAGAGTG
```

The PCRs (using Pfu polymerase from Promega cod. M7745; PCR conditions set following manufacturing's instruction) produced single fragments, which were purified by gel electrophoresis (using Wizard SV Gel and PCR Clean-Up system, Promega cod. A9281), quantified and mixed at the right proportion. The recommended DNA Ratio for 4-6 Fragment Assembly was 1:1 (vector:insert, total amount of fragments: 0.2-0.5 pmols).

Specifically, 30 ng of each fragments (0.01 pmols for fragment (1); 0.062 pmols for fragment (2); 0.088 pmols for fragment (3); 0.087 pmols for fragment (4)) were added to the Gibson Assembly master mix (#M5510A, New England Biolabs), incubated for 60 min at 50° C., and used to transform competent XL1 *E. coli* strain. The bacteria were cloned and analyzed for the presence of a plasmid of 6035 base pairs ("bp").

The plasmid was verified by restriction enzyme digestion (with XhoI and XbaI) and DNA sequencing. XhoI corresponds to two restriction sites in the plasmid sequence, giving two fragments of 966 and 5,068 bp (cut position: 1,098 and 2,624). XbaI corresponds to one restriction site in the plasmid sequence (cut position: 4,636).

Table 1 below depicts the Sequence of the pWUR-FTH-tetO-FTL Plasmid.

Sequence 2, comprised of 558 bp, is FtH.

Sequence 3, comprised of 570 bp, is the intervening back sequence.

Sequence 4, comprised of 528 bp, is FtL.

The sequences provided in Table 1 are separated by Sequence I.D. Numbers ("Seq. I.D. No.") for clarity in identifying specific regions of interest and should be construed as being contiguous and a part of the same sequence.

TABLE 1

Sequence of the pWUR-FTH-tetO-FTL Plasmid (FIG. 1A)

Sequence 1.
TAATACGACTCACTATAGGGGAATTGTGAGCGGATAACAA
TTCCCCTGTAGAAATAATTTTGTTTAACTTTAATAAGGAG
ATATACC
(SEQ ID NO: 1)

Sequence 2.
ATGGCTAGCACGACCGCGTCCACCTCGCAGGTGCGCCAGA
ACTACCACCAGGACTCAGAGGCCGCCATCAACCGCCAGAT
CAACCTGGAGCTCTACGCCTCCTACGTTTACCTGTCCATG
TCTTACTACTTTGACCGCGATGATGTGGCTTTGAAGAACT
TTGCCAAATACTTTCTTCACCAATCTCATGAGGAGAGGGA
ACATGCTGAGAAACTGATGAAGCTGCAGAACCAACGAGGT
GGCCGAATCTTCCTTCAGGATATCAAGAAACCAGACTGTG
ATGACTGGGAGAGCGGGCTGAATGCAATGGAGTGTGCATT
ACATTTGGAAAAAAATGTGAATCAGTCACTACTGGAACTG
CACAAACTGGCCACTGACAAAAATGACCCCCATTTGTGTG
ACTTCATTGAGACACATTACCTGAATGAGCAGGTGAAAGC
CATCAAAGAATTGGGTGACCACGTGACCAACTTGCGCAAG
ATGGGAGCGCCCGAATCTGGCTTGGCGGAATATCTCTTTG
ACAAGCACACCCTGGGAGACAGTGATAATGAAAGCTAA
(SEQ ID NO: 2)

Sequence 3.
GCGGCCGCGGCTGTTTTGGCGGATGAGAGAAGATTTTCAG
CCTGATACAGATTAAATCAGAACGCAGAAGCGGTCTGATA
AAACAGAATTTGCCTGGCGGCAGTAGCGCGGTGGTCCCAC
CTGACCCCATGCCGAACTCAGAAGTGAAACGCCGTAGCGC
CGATGGTAGTGTGGGGTCTCCCCATGCGAGAGTAGGGAAC
TGCCAGGCATCAAATAAAACGAAAGGCTCAGTCGAAAGAC
TGGGCCTTTCGTTTTATCTGTTGTTTGTCGGTGAACGCTC
TCCTGAGTAGGACAAATCCGCCGGGAGCGGATTTGAACGT
TGCGAAGCAACGGCCCGGAGGGTGGCGGGCAGGACGCCCG
CCATAAACTGCCAGGCATCAAATTAAGCAGAAGGCCATCC
GTCAGGATGGCCTTTTTGCGTTTCTACAAACTCTGCTAGC
AAGTAAGGCCGACTCGAGTCCCTATCAGTGATAGAGATTG
ACATCCCTATCAGTGATAGAGATACTGAGCACATCAGCAG
GACGCACTGACCGAATTCATTAAATTTAACTTTAAGAAGG
AGATATACAT
(SEQ ID NO: 3)

Sequence 4.
ATGAGCTCCCAGATTCGTCAGAATTATTCCACCGACGTGG
AGGCAGCCGTCAACAGCCTGGTCAATTTGTACCTGCAGGC
CTCCTACACCTACCTCTCTCTGGGCTTCTATTTCGACCGC
GATGATGTGGCTCTGGAAGGCGTGAGCCACTTCTTCCGCG
AATTGGCCGAGGAGAAGCGCGAGGGCTACGAGCGTCTCCT
GAAGATGCAAAACCAGCGTGGCGGCCGCGCTCTCTTCCAG
GACATCAAGAAGCCAGCTGAAGATGAGTGGGGTAAAACCC
CAGACGCCATGAAAGCTGCCATGGCCCTGGAGAAAAAGCT
GAACCAGGCCCTTTTGGATCTTCATGCCCTGGGTTCTGCC
CGCACGGACCCCCATCTCTGTGACTTCCTGGAGACTCACT
TCCTAGATGAGGAAGTGAAGCTTATCAAGAAGATGGGTGA
CCACCTGACCAACCTCCACAGGCTGGGTGGCCCGGAGGCT
GGGCTGGGCGAGTATCTCTTCGAAAGGCTCACTCTCAAGC
ACGACTAA
(SEQ ID NO: 4)

Sequence 5.
GCCTTAATTAACGGCACTCCTCAGCAAATATAATGACCCT
CTTGATAACCCAAGAGGGCATTTTTTAATGCCCATGGCGT
TTACCACAGCTAACACCACGTCGTCCCTATCTGCTGCCCT
AGGTCTATGAGTGGTTGCTGGATAACTTTACGGGCATGCA
TAAGGCTCGTAGGCTATATTCAGGGAGACCACAACGGTTT
CCCTCTACAAATAATTTTGTTTAACTTTGAAATAAGGAGG
TAATACAAATGTCTCGTTTAGATAAAAGTAAAGTGATTAA
CAGCGCATTAGAGCTGCTTAATGAGGTCGGAATCGAAGGT
TTAACAACCCGTAAACTCGCCCAGAAGCTAGGTGTAGAGC
AGCCTACATTGTATTGGCATGTAAAAAATAAGCGGGCTTT
GCTCGACGCCTTAGCCATTGAGATGTTAGATAGGCACCAT
ACTCACTTTTGCCCTTTAGAAGGGGAAAGCTGGCAAGATT
TTTTACGTAATAACGCTAAAAGTTTTAGATGTGCTTTACT
AAGTCATCGCGATGGAGCAAAAGTACATTTAGGTACACGG
CCTACAGAAAAACAGTATGAAACTCTCGAAAATCAATTAG
CCTTTTTATGCCAACAAGGTTTTTCACTAGAGAATGCATT
ATATGCACTCAGCGCTGTGGGGCATTTTACTTTAGGTTGC
GTATTGGAAGATCAAGAGCATCAAGTCGCTAAAGAAGAAA TABLE 1-continued Sequence of the pWUR-FTH-tetO-FTL Plasmid (FIG. 1A)

GGGAAACACCTACTACTGATAGTATGCCGCCATTATTACG
ACAAGCTATCGAATTATTTGATCACCAAGGTGCAGAGCCA
GCCTTCTTATTCGGCCTTGAATTGATCATATGCGGATTAG
AAAAACAACTTAAATGTGAAAGTGGGTCTTAATAAGCGAC
CTCGAGTCTGGTAAAGAAACCGCTGCTGCGAAATTTGAAC
GCCAGCACATGGACTCGTCTACTAGCGCAGCTTAATTAAC
CTAGGCTGCTGCCACCGCTGAGCAATAACTAGCATAACCC
CTTGGGGCCTCTAAACGGGTCTTGAGGGGTTTTTTGCTGA
AACCTCAGGCATTTGAGAAGCACACGGTCACACTGCTTCC
GGTAGTCAATAAACCGGTAAACCAGCAATAGACATAAGCG
GCTATTTAACGACCCTGCCCTGAACCGACGACCGGGTCAT
CGTGGCCGGATCTTGCGGCCCCTCGGCTTGAACGAATTGT
TAGACATTATTTGCCGACTACCTTGGTGATCTCGCCTTTC
ACGTAGTGGACAAATTCTTCCAACTGATCTGCGCGCGAGG
CCAAGCGATCTTCTTCTTGTCCAAGATAAGCCTGTCTAGC
TTCAAGTATGACGGGCTGATACTGGGCCGGCAGGCGCTCC
ATTGCCCAGTCGGCAGCGACATCCTTCGGCGCGATTTTGC
CGGTTACTGCGCTGTACCAAATGCGGGACAACGTAAGCAC
TACATTTCGCTCATCGCCAGCCCAGTCGGGCGGCGAGTTC
CATAGCGTTAAGGTTTCATTTAGCGCCTCAAATAGATCCT
GTTCAGGAACCGGATCAAAGAGTTCCTCCGCCGCTGGACC
TACCAAGGCAACGCTATGTTCTCTTGCTTTTGTCAGCAAG
ATAGCCAGATCAATGTCGATCGTGGCTGGCTCGAAGATAC
CTGCAAGAATGTCATTGCGCTGCCATTCTCCAAATTGCAG
TTCGCGCTTAGCTGGATAACGCCACGGAATGATGTCGTCG
TGCACAACAATGGTGACTTCTACAGCGCGGAGAATCTCGC
TCTCTCCAGGGGAAGCCGAAGTTTCCAAAAGGTCGTTGAT
CAAAGCTCGCCGCGTTGTTTCATCAAGCCTTACGGTCACC
GTAACCAGCAAATCAATATCACTGTGTGGCTTCAGGCCGC
CATCCACTGCGGAGCCGTACAAATGTACGGCCAGCAACGT
CGGTTCGAGATGGCGCTCGATGACGCCAACTACCTCTGAT
AGTTGAGTCGATACTTCGGCGATCACCGCTTCCCTCATAC
TCTTCCTTTTTCAATATTATTGAAGCATTTATCAGGGTTA
TTGTCTCATGAGCGGATACATATTTGAATGTATTTAGAAA
AATAAACAAATAGCTAGCTCACTCGGTCGCTACGCTCCGG
GCGTGAGACTGCGGCGGGCGCTGCGGACACATACAAAGTT
ACCCACAGATTCCGTGGATAAGCAGGGGACTAACATGTGA
GGCAAAACAGCAGGGCCGCGCCGGTGGCGTTTTTCCATAG
GCTCCGCCCTCCTGCCAGAGTTCACATAAACAGACGCTTT
TCCGGTGCATCTGTGGGAGCCGTGAGGCTCAACCATGAAT
CTGACAGTACGGGCGAAACCCGACAGGACTTAAAGATCCC
CACCGTTTCCGGCGGGTCGCTCCCTCTTGCGCTCTCCTGT
TCCGACCCTGCCGTTTACCGGATACCTGTTCCGCCTTTCT
CCCTTACGGGAAGTGTGGCGCTTTCTCATAGCTCACACAC
TGGTATCTCGGCTCGGTGTAGGTCGTTCGCTCCAAGCTGG
GCTGTAAGCAAGAACTCCCCGTTCAGCCCGACTGCTGCGC
CTTATCCGGTAACTGTTCACTTGAGTCCAACCCGGAAAAG
CACGGTAAAACGCCACTGGCAGCAGCCATTGGTAACTGGG
AGTTCGCAGAGGATTTGTTTAGCTAAACACGCGGTTGCTC
TTGAAGTGTGCGCCAAAGTCCGGCTACACTGGAAGGACAG
ATTTGGTTGCTGTGCTCTGCGAAAGCCAGTTACCACGGTT
AAGCAGTTCCCCAACTGACTTAACCTTCGATCAAACCACC
TCCCCAGGTGGTTTTTTCGTTTACAGGGCAAAAGATTACG
CGCAGAAAAAAAGGATCTCAAGAAGATCCTTTGATCTTTT
CTACTGAACCGCTCTAGATTTCAGTGCAATTTATCTCTTC
AAATGTAGCACCTGAAGTCAGCCCCATACGATATAAGTTG
TAATTCTCATGTTAGTCATGCCCCGCGCCCACCGGAAGGA
GCTGACTGGGTTGAAGGCTCTCAAGGGCATCGGTCGAGAT
CCCGGTGCCTAATGAGTGAGCTAACTTACATTAATTGCGT
TGCGCTCACTGCCCGCTTTCCAGTCGGGAAACCTGTCGTG
CCAGCTGCATTAATGAATCGGCCAACGCGCGGGGAGAGGC
GGTTTGCGTATTGGGCGCCAGGGTGGTTTTTCTTTTCACC
AGTGAGACGGGCAACAGCTGATTGCCCTTCACCGCCTGGC
CCTGAGAGAGTTGCAGCAAGCGGTCCACGCTGGTTTGCCC
CAGCAGGCGAAAATCCTGTTTGATGGTGGTTAACGGCGGG
ATATAACATGAGCTGTCTTCGGTATCGTCGTATCCCACTA
CCGAGATGTCCGCACCAACGCGCAGCCCGGACTCGGTAAT
GGCGCGCATTGCGCCCAGCGCCATCTGATCGTTGGCAACC
AGCATCGCAGTGGGAACGATGCCCTCATTCAGCATTTGCA
TGGTTTGTTGAAAACCGGACATGGCACTCCAGTCGCCTTC
CCGTTCCGCTATCGGCTGAATTTGATTGCGAGTGAGATAT
TTATGCCAGCCAGCCAGACGCAGACGCGCCGAGACAGAAC
TTAATGGGCCCGCTAACAGCGCGATTTGCTGGTGACCCAA
TGCGACCAGATGCTCCACGCCCAGTCGCGTACCGTCTTCA
TGGGAGAAAATAATACTGTTGATGGGTGTCTGGTCAGAGA
CATCAAGAAATAACGCCGGAACATTAGTGCAGGCAGCTTC
CACAGCAATGGCATCCTGGTCATCCAGCGGATAGTTAATG

TABLE 1-continued

| Sequence of the pWUR-FTH-tetO-FTL Plasmid (FIG. 1A) |
|---|
| ATCAGCCCACTGACGCGTTGCGCGAGAAGATTGTGCACCG<br>CCGCTTTACAGGCTTCGACGCCGCTTCGTTCTACCATCGA<br>CACCACCACGCTGGCACCCAGTTGATCGGCGCGAGATTTA<br>ATCGCCGCGACAATTTGCGACGGCGCGTGCAGGGCCAGAC<br>TGGAGGTGGCAACGCCAATCAGCAACGACTGTTTGCCCGC<br>CAGTTGTTGTGCCACGCGGTTGGGAATGTAATTCAGCTCC<br>GCCATCGCCGCTTCCACTTTTTCCCGCGTTTTCGCAGAAA<br>CGTGGCTGGCCTGGTTCACCACGCGGGAAACGGTCTGATA<br>AGAGACACCGGCATACTCTGCGACATCGTATAACGTTACT<br>GGTTTCACATTCACCACCCTGAATTGACTCTCTTCCGGGC<br>GCTATCATGCCATACCGCGAAAGGTTTTGCGCCATTCGAT<br>GGTGTCCGGGATCTCGACGCTCTCCCTTATGCGACTCCTG<br>CATTAGGAAAT<br>(SEQ ID NO: 5) |

The resulting plasmid, pWUR-FtH-tetO-FtL, includes 6,034 base pairs. The distance between the two gene sequences (FtH and FtL) is 570 nucleotides, with 11 stop codons in between the sequences.

FIG. 1 depicts the software-generated plasmid map of the plasmid (pWUR-FtH-tetO-FtL). Arrows on the inside of the circle denote direction of transcription.

In embodiments of the pWUR-FtH-tetO-FtL plasmid, the FtH gene is cloned downstream of the Lac operator (the T7 promoter), under control of the Lac I repressor (the T1 terminator sequence), with T7 polymerase, and expression induced by isopropyl β-D-1 thiogalactopyranoside ("IPTG") (see FIG. 1). Exposure to a concentration of an IPTG inducer activates the T7 promoter, upstream from the ferritin cDNA.

In embodiments of the pWUR-FtH-tetO-FtL plasmid, the FtL gene is cloned downstream of the Tet operator (the Tet-On system), under the TetR repressor sequence, with expression induced by a member of the antibiotic group of tetracyclines such as anhydrotetracycline. Exposure to a concentration of a tetracycline, or a tetracycline derivative, inducer activates the Tet promoter, upstream from the ferritin cDNA.

The described cloning method works in *E. coli* hosts.

BL21 Embodiment

In embodiments, the present disclosure uses (as a bacterial host) the BL21 (DE3) pLys strain ("BL21") of *E. coli*. The BL21 strain contains the T7 RNA polymerase gene, under the control of the lac I operator, as well as the plasmid pLysE that constitutively expresses the T7 lysozyme. The T7 lysozyme is a natural inhibitor of T7 RNA polymerase. The strain of this embodiment is used to minimize basal level expression of potentially toxic gene products before induction with IPTG.

In initial experiments, the BL21 strain was transformed with the pWUR-FtH-tetO-FtL plasmid, and the two chains of ferritin were induced with different concentrations of IPTG and Tetracycline (e.g., anhydrous Tet or anhydrotetracycline). *E. coli* expressed ferritin supernatant were loaded for analysis in the presence of β-mercaptoethanol (β-SH), stained with Coomassie blue. Experiments were run on 12% Sodium Dodecyl Sulfate-Polyacrylamide Gel Electrophoresis ("12% SDS PAGE") and 7.5% Nondenaturing Polyacrylamide Gel Electrophoresis ("7.5% Native PAGE").

In SDS PAGE, SDS is an anionic detergent that imparts a series of negative charge in the protein molecule making it a linear negatively charged polypeptide chain. The charge being the same, the protein then migrates solely due to mass. In contrast in Native PAGE, the protein migrates by charge to mass ratio.

Figure 18A:
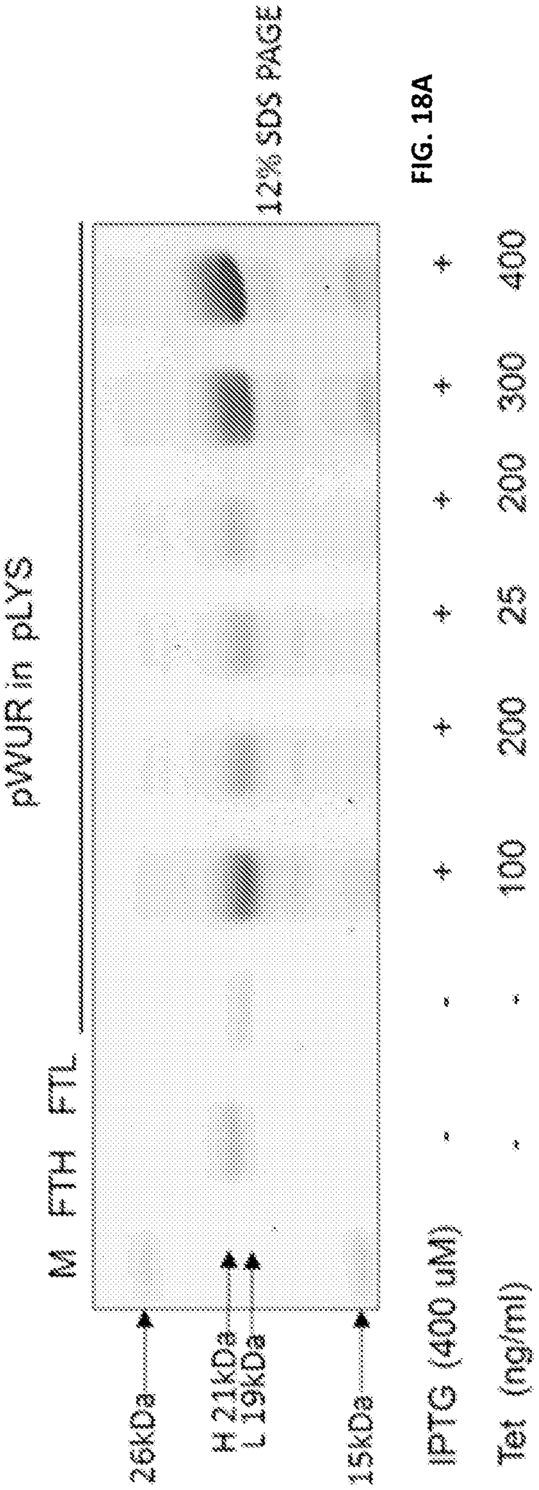
FIGS. 18(A) and 18(B) depict electrophoretic analyses, on 12% SDS PAGE and 7.5% Native PAGE respectively, of ferritin expressed by a BL21(DE3) pLys *E. coli* cell culture at various inducer ratios.

FIG. 18(A) depicts electrophoretic analyses, on 12% SDS PAGE, of a BL21(DE3) pLys *E. coli* cell culture with the following ratios of the inducer IPTG to the inducer Tet: 400 μM IPTG to 100 ng/mL Tet; 400 μM IPTG to 200 ng/mL Tet; 400 μM IPTG to 25 ng/mL Tet; 400 μM IPTG to 200 ng/mL Tet; 400 μM IPTG to 300 ng/mL Tet; and 400 μM IPTG to 400 ng/mL Tet.

Figure 18B:
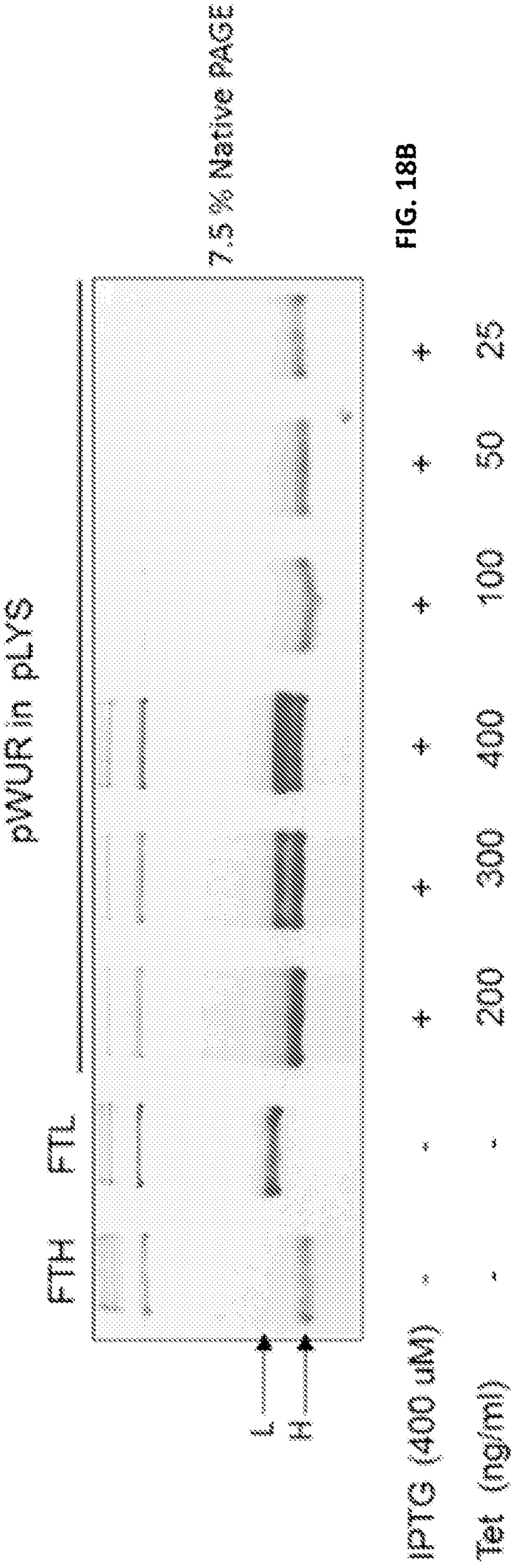

FIG. 18(B) depicts electrophoretic analyses, on 7.5% Native PAGE, of a BL21(DE3) pLys *E. coli* cell culture with the following ratios of the inducer IPTG to the inducer Tet: 400 μM IPTG to 200 ng/mL Tet; 400 μM IPTG to 300 ng/mL Tet; 400 μM IPTG to 400 ng/mL Tet; 400 μM IPTG to 100 ng/mL Tet; 400 μM IPTG to 50 ng/mL Tet; and 400 μM IPTG to 25 ng/mL Tet.

The protein molecular weight marker on 12% SDS PAGE and 7.5% Native PAGE consists of 1 μg FtH and 1 μg FtL and represents the control protein bands [FIGS. 18(A) and 18(B)]. Protein molecular weight markers, sometimes called protein ladders, are used to calculate sample molecular weights, to monitor the progress of an electrophoretic run, or as a positive control for analysis conditions. For the purposes of the invention described herein, molecular weight markers are used as a positive control to monitor the progress of electrophoretic run.

As shown in FIG. 18(A), analyses of 12% SDS PAGE results experimentally confirmed that the FtH is induced by increasing concentrations of IPTG, and the FtL is induced by increasing concentrations of Tet. In other words, increasing the concentration of IPTG corresponds to an increase in FtH expression, and increasing the concentration of Tet corresponds to an increase in FtL expression.

As shown in FIG. 18(B), electrophoretic analysis of the soluble fraction of the cell homogenates was also carried out on 7.5% Native PAGE, which separates fully assembled 24-mer ferritin shells. The 7.5% Native PAGE demonstrates the homogeneity of the ferritins and mobilities of heteropolymer related to the FtH and FtL in its native state.

The 7.5% Native PAGE showed two bands; one band corresponding to the FtH, and the other band corresponding to FtL. The bands are visible on the fourth lane (i.e., 400 uM IPTG and 300 ng/mL Tet) and the fifth lane (i.e. 400 uM IPTG and 400 Tet ng/mL) of the gel. The 7.5% Native PAGE analyses suggest that most of the two subunits did not co-assemble to form heteropolymers and remained as two separate homopolymer subunit entities.

Figure 22A:
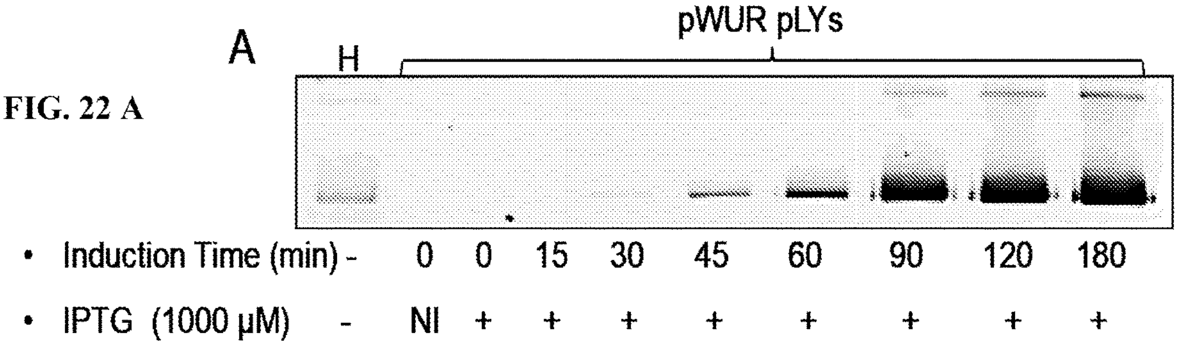
FIGS. 22A-22D depict: A) 1000 μM IPTG (B) 400 μM IPTG and (C) 300 ng/ml anhydrotetracycline: Expression rate represented on 7.5% Native-PAGE loaded with 1 μg of H and L purified protein as a reference. The samples collected from 0 to 180 min, time course. The samples were lysed following the previous protocol and the supernatant was loaded on to the gel. The gel was stained with Coomassie blue (D) Graphical representation of induction kinetics showing the rate formation of H and L at different time courses (0-180 min). The protein band observed on native-PAGE intensity was measured by densitometric analysis using Image J software.
Figure 22B:
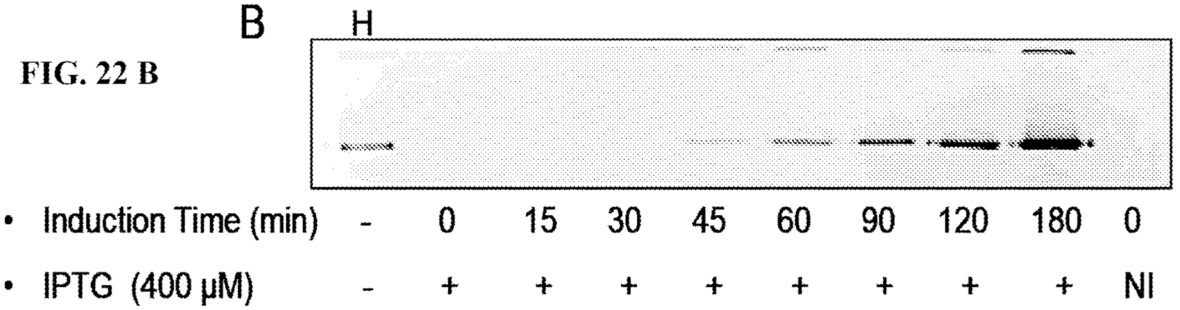
Figure 22C:
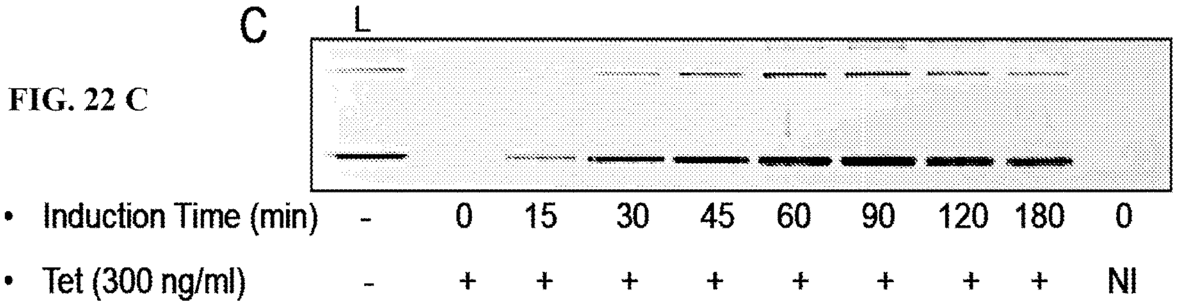
Figure 22D:
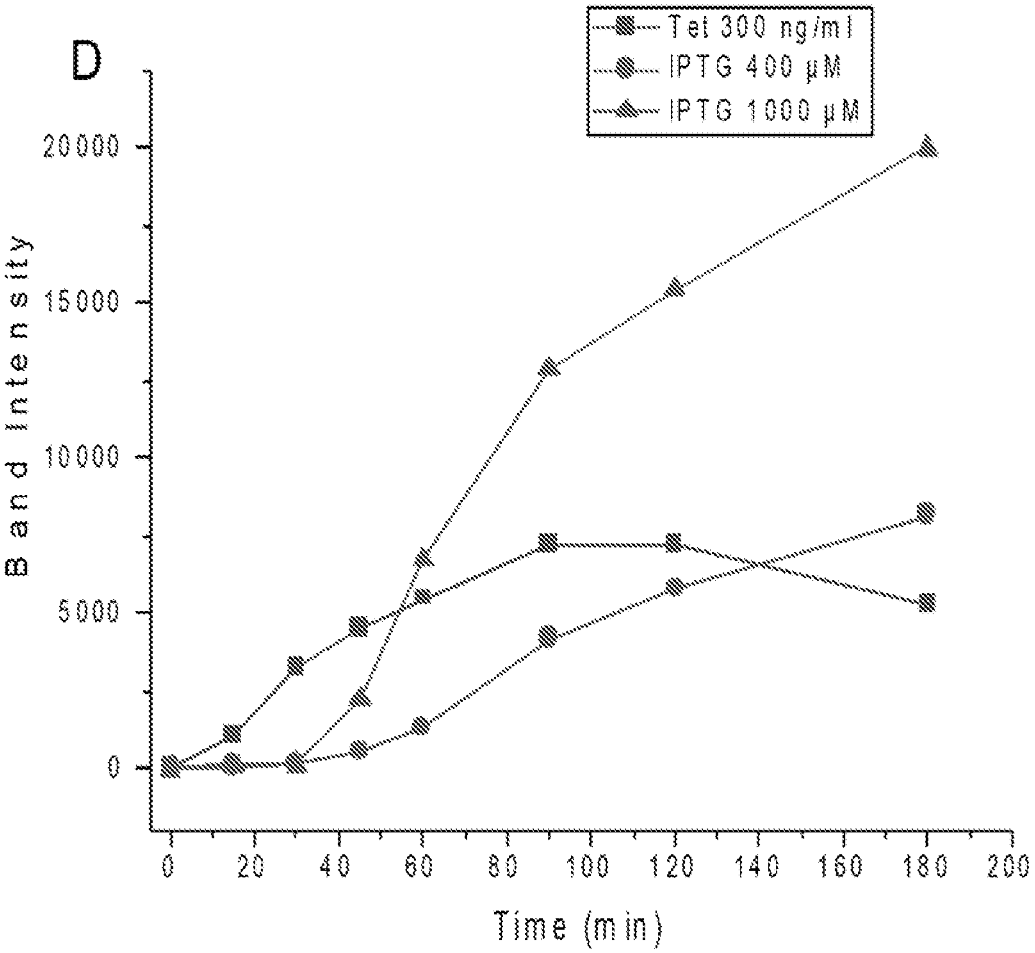

Referring now to FIG. 22A-22D, FIG. 22A (1000 μM IPTG) FIG. 22B (400 μM IPTG) and FIG. 22(C) (300 ng/ml anhydrotetracycline): Expression rate represented on 7.5% Native-PAGE loaded with 1 μg of H and L purified protein as a reference. The samples collected from 0 to 180 min, time course. The samples were lysed following the previous protocol and the supernatant was loaded on to the gel. The gel was stained with Coomassie blue and FIG. 22D is a graphical representation of induction kinetics showing the rate formation of H and L at different time courses (0-180 min). The protein band observed on native-PAGE intensity was measured by densitometric analysis using Image J software.

Figure 23:
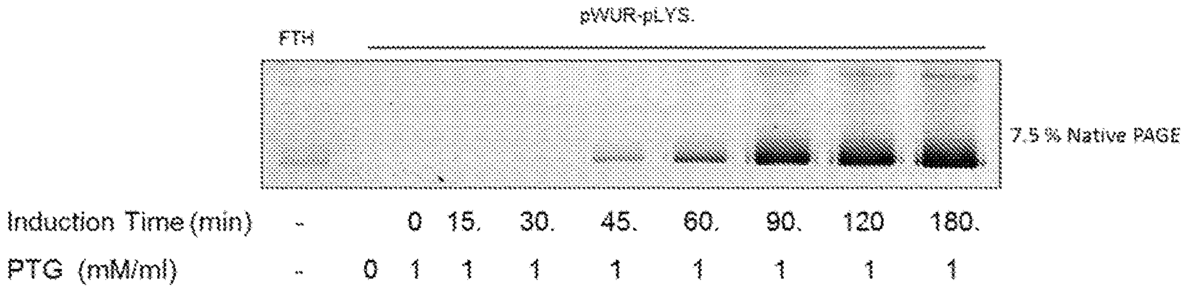
FIG. 23 depicts the same conditions as FIG. 22(A) but with a higher concentration of IPTG in BL21 host.

FIG. 23 depicts electrophoretic analyses, on 7.5% Native PAGE, of the induction rate of FtH with 1 mM/ml IPTG in BL21(DE3) pLys *E. coli* cell culture at the following time intervals: 0 minutes; 15 minutes; 30 minutes; 45 minutes; 60 minutes; 90 minutes; 120 minutes; and 180 minutes.

Even with higher concentrations of IPTG as shown in FIG. 23, 1 mM compared to the initial 0.4 mM IPTG, the 7.5% Native PAGE showed an increased amount of FtH, but it had no effect on the rate of production. In other words, as depicted in FIG. 23, it took the same amount of time, about 30 minutes, for FtH band to appear.

Figure 24:
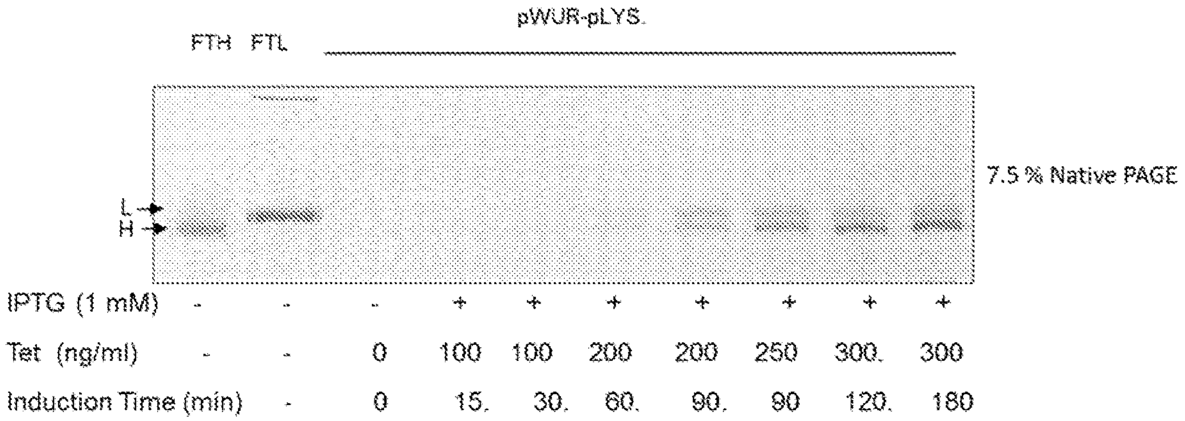
FIG. 24 depicts electrophoresis analysis, on 7.5% Native PAGE, of induction by IPTG and Tet at specific times in the BL21 host.

FIG. 24 depicts electrophoretic analyses, on 7.5% Native PAGE, of the induction rate of FtH and FtL at the following ratios of Inducer IPTG to Inducer Tet: 1 mM IPTG to Ong/ml Tet; 1 mM IPTG to 100 ng/ml Tet; 1 mM IPTG to 200 ng/ml Tet; 1 mM IPTG to 250 ng/ml; and 1 mM IPTG to 300 ng/ml, at the following time intervals: 0 minutes; 15 minutes; 30 minutes; 60 minutes; 90 minutes; 120 minutes; and 180 minutes.

As shown in FIG. 24, FtH and FtL induction was stopped at specific times, under conditions of 1 mM IPTG and concentrations of Tet that ranged from 100 ng/ml to 300 ng/ml. The resulting sample was analyzed on 7.5% Native PAGE that showed two distinct bands.

This means that neither varying the concentrations of inducers, nor varying the times at which samples were collected allowed for FtH and FtL to assemble into heteropolymer ferritin. As is evidence by FIG. 23 and FIG. 24, the two ferritin subunits were produced separately and in this case did not assemble into a heteropolymer structure.

In the BL21 host, the FtL, which is expressed first, assembles into a homopolymers prior to the expression of FtH. (FIG. 24). Thus, no FtL is available to co-assemble with FtH and a heteropolymer is not produced (FIG. 24).

Rosetta-Gami B Embodiment

Another embodiment of this disclosure uses (as the bacterial host) the Rosetta-gami B strain of *E. coli* [(Chromosomal Genotype: F-ompT hsdSB (rB-mB-) gal dcm lacY1 ahpC (DE3) gor522: Tn10 trxB pRARE (CamR, KanR, TetR)]. The Rosetta strain is functionally advantageous because it combines several features of the BL21, Origami, and Rosetta strains of *E. coli*, which enhance both the expression of eukaryotic proteins and the formation of target protein disulfide bonds in the bacterial cytoplasm. These strains are compatible with ampicillin- or spectinomycin-resistant vectors.

The Rosetta-gami B strain carries a chromosomal copy of the T7 RNA polymerase gene under control of the lacUV5 promoter. T7 RNA Polymerase synthesizes RNA at a rate serval times that of traditional *E. coli* RNA Polymerase, and it terminates transcription less frequently. The lacUV5 promoter recruit's RNA polymerase more effectively, leading to higher rate of transcription, than the traditional *E. coli* lac promoter.

The Rosetta-gami B strain of *E. coli* carries a mutation in the lac permease gene ("lacY") that enables uniform entry of IPTG into all cells in the population. The lacY mutation produces a fast and concentration-dependent level of induction. Expression can be regulated by adjusting the concentration of IPTG and range from low to high expression levels. Lower level expression may enhance solubility and activity of proteins that are typically difficult to express.

Similar to the BL21 host, the Rosetta-gami B strain was transformed with the pWUR-FtH-tetO-FtL plasmid, and the two chains of ferritin were induced with different concentrations of IPTG and Tetracycline (e.g., anhydrous Tet). Experiments were run on 12% SDS PAGE and 7.5% Native PAGE.

FIG. 19 depicts an electrophoretic analysis, on 12% SDS PAGE, of various cell cultures at the following ratios of the inducer IPTG to the inducer Tet: a Rosetta-gami B cell culture at 400 μM IPTG to 0 ng/mL Tet; a Rosetta-gami B cell culture 0 μM IPTG to 200 ng/mL Tet; a BL21(DE3) pLys *E. coli* cell culture at 400 μM IPTG to 0 ng/mL Tet; and a BL21(DE3) pLys *E. coli* cell culture at 0 μM IPTG to 800 ng/mL Tet. Preliminary results indicated that expression of the FtH and FtL—using the Rosetta-gami B host—are similarly efficient to, if not better than, that of the BL21 host.

FIG. 20(A) depicts an electrophoretic analysis, on 12% SDS PAGE, of a Rosetta-gami B cell culture, comparing the formation of FtH and FtL, at the following ratios of the inducer IPTG to the inducer Tet: 400 μM IPTG and 600 ng/mL Tet.

FIG. 20(B) depicts an electrophoretic analysis, on 7.5% Native PAGE, of a Rosetta-gami B cell culture, comparing the formation of FtH and FtL, at the following ratios of the inducer IPTG to the inducer Tet: 400 μM IPTG and 600 ng/mL Tet.

As shown in FIG. 20(B), electrophoretic analysis showed the formation of a single band, even when the two subunits were expressed at similar levels indicating that the two subunits co-assembled to form 24-mer heteropolymer ferritin (a single, observable protein band is indicative of presence of a single protein species).

Figure 21A:
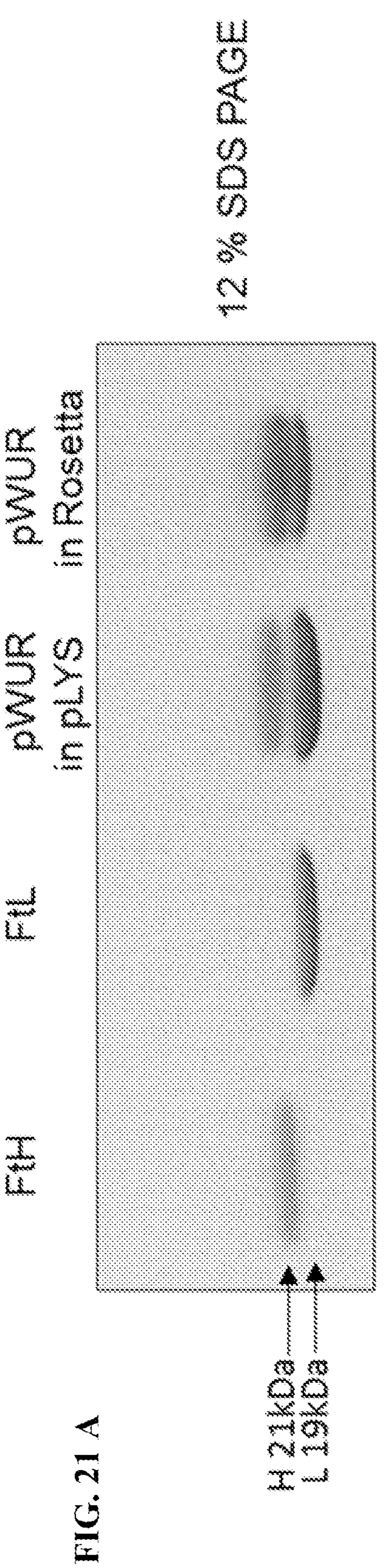
FIGS. 21(A) and 21(B) depict electrophoretic analyses, on 12% SDS PAGE and 7.5% Native PAGE respectively, of ferritin expressed by a Rosetta-gami B cell culture and a BL21(DE2) pLys cell culture, comparing the formation of FtH and FtL, at various inducer ratios.

FIG. 21(A) depicts an electrophoretic analysis, on 12% SDS PAGE, comparing the formation of FtH and FtL in a Rosetta-gami B cell culture at a ratio of 400 μM IPTG and 300 ng/mL Tet and the formation of FtH and FtL in a BL21(DE2) pLys cell culture at a ratio of 100 μM IPTG and 600 ng/mL Tet.

Figure 21B:
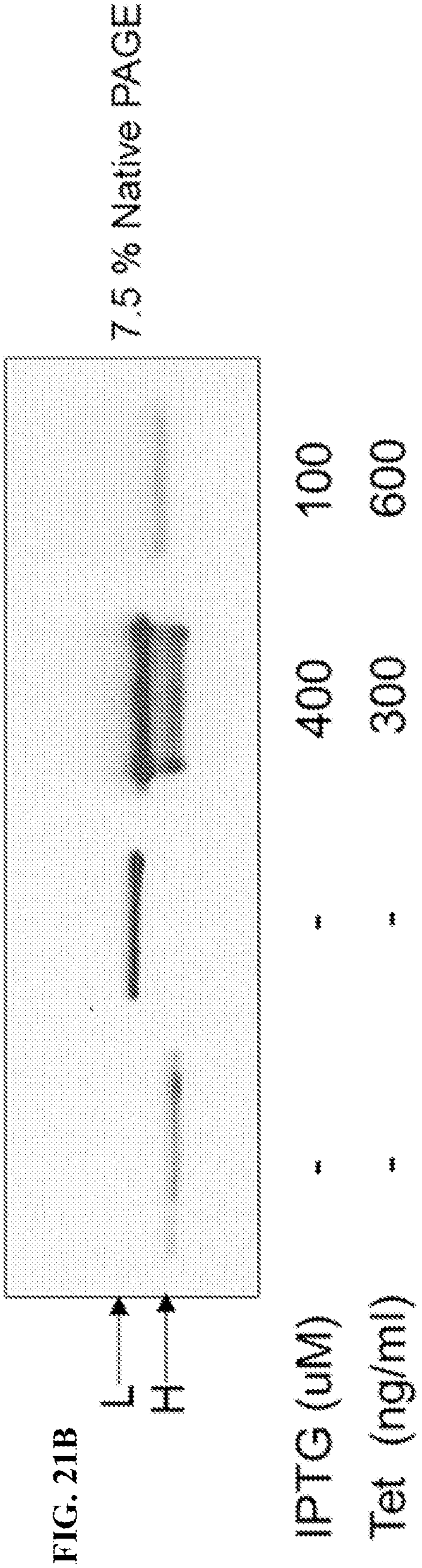

FIG. 21(B) depicts an electrophoretic analysis, on 7.5% Native PAGE, comparing the formation of FtH and FtL in a Rosetta-gami B cell culture at a ratio of 400 μM IPTG and 300 ng/mL Tet and the formation of FtH and FtL in a BL21 cell culture at a ratio of 100 μM IPTG and 600 ng/mL Tet.

As shown in FIG. 21, when both FtH and FtL are produced through the BL21 host two distinct bands are visible on the 7.5% Native PAGE; one representing homopolymer FtH ferritin and one representing homopolymer FtL ferritin. The presence of two distinct protein bands indicates that FtH and FtL did not combine to form heteropolymer Ferritin.

In contrast, when both FtH and FtL are produced through the Rosetta-gami B host only one distinct band is visible. The presence of one distinct protein band indicates that the FtH and FtL subunits combined to form heteropolymer Ferritin. The result supports the conclusion that ferritin subunits produced through the Rosetta host are co-assembled to form a 24-mer heteropolymer ferritin molecules.

Method for Expression

The transformation of the Rosetta bacterial host using the pWUR-FtH-tetO-FtL plasmid embodies the method for expressing ferritin heteropolymers; the transformation of the BL21 bacterial host using the pWUR-FtH-tetO-FtL plasmid embodies the method for expressing ferritin homopolymers. In embodiments, regardless of which specific host is used, recombinant ferritin cloned in the pWUR-FtH-tetO-FtL plasmid is used to transform the bacterial host.

The *E. coli* bacterial host is grown at 37° C. with 250 RPM agitation for the duration of a 4-hour inducement. Subsequently, ferritin expression is induced with IPTG to produce FtH and Tetracycline (e.g., anhydrous Tet or anhydrotetracycline) for production of FtL.

In embodiments, to produce heteropolymer ferritin at different H:L ratios, FtH and FtL hybrid expression is carried out using different inducer concentrations. The two inducers (e.g., IPTG and Tet) are added together in an inoculum of 0.4-0.5 OD and induced for 4 hours.

Following incubation, culture pellets are lysed/sonicated to disrupt bacterial walls and obtain a homogenate. The homogenate is subsequently centrifuged, and the cell pellets are discarded. This results in a supernatant derived from the culture pellets.

Standard protein purification procedure is performed on the resulting supernatant. Specifically, taking advantage of the thermal stability of the ferritin, the supernatant is heated at 75° C. for 10 minutes centrifuged at 12,000 rpm for 20 minutes, and analyzed on 12% denaturing SDS-PAGE and 7.5% non-denaturing gel.

In embodiments, ferritin is further purified by treating the supernatant with ammonium sulfate for 4-hours at 4° C. (5.3 g of ammonium sulfate is used for every 10 mL of supernatant). The resulting sample (ammonium sulfate treated sample) is centrifuged at 12,000 rpm for 30 minutes. The surplus supernatant is discarded, and the ammonium sulfate protein precipitate is collected.

Thereafter, the ammonium sulfate protein precipitate is resuspended and then dialyzed, for at least 18 hours, against a 20 mM Tris buffer with a pH of 7.4. The dialyzed protein sample is then loaded on a GE Healthcare Life Sciences 16/100 column packed with superose 6 resin equilibrated in 20 mM Tris buffer with a pH of 7.4. In other embodiments, alternative columns may be employed to purify the ferritin, and depending on the column diameter and depth, different resins such as sepharose 6B or ABT agarose can be used. Using a linearflow rate of 1 mL/min, protein fractions are collected and analyzed on 12% SDS PAGE. The fractions containing pure ferritin are then pooled, collected and concentrated with 100 kDa cut-off membrane filter (Millipore).

Experiments were run on 12% SDS PAGE and 7.5% Native PAGE following induction at various IPTG and Tet concentrations. The band intensity and migration of each subunit was examined as an indication of formation of heteropolymer ferritin species of different H:L ratio.

Figure 2B:
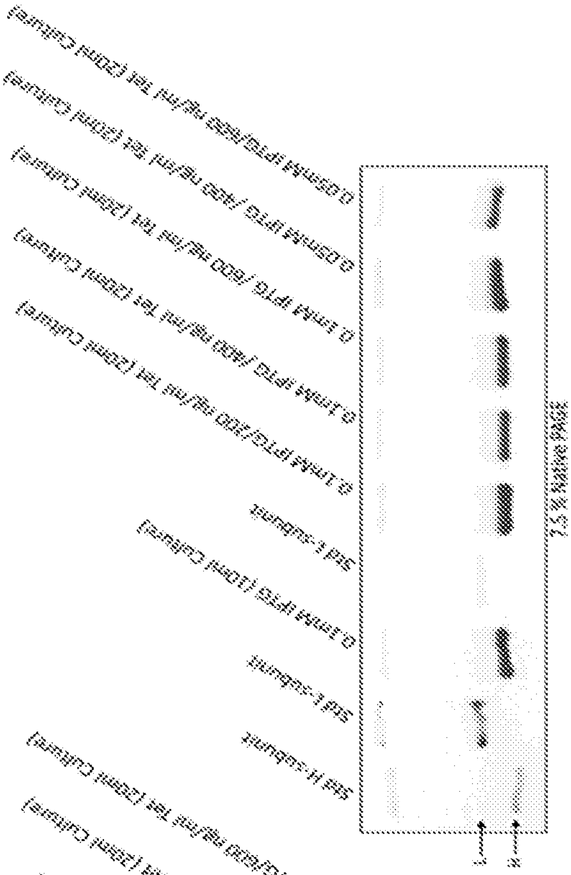
FIGS. 2(A) and 2(B), depict electrophoretic analyses, on 12% SDS PAGE and 7.5% Native PAGE respectively, of ferritin expressed by an *E. coli* cell culture at various inducer ratios and cell culture sizes.
Figure 2A:
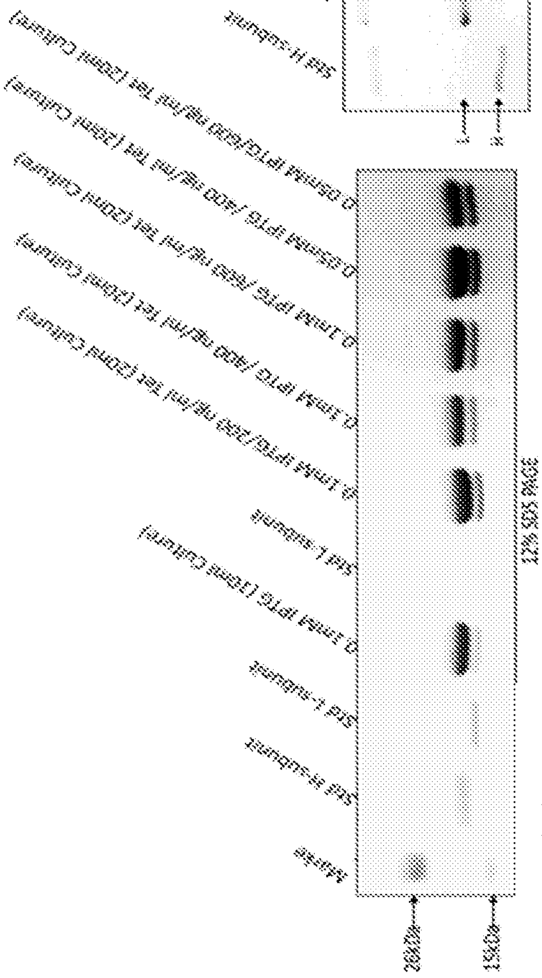

FIG. 2(A) depicts an electrophoretic analysis of FtH and FtL synthesized by the Rosetta-gami B strain, on 12% SDS PAGE, at the following ratios of the inducer IPTG to the inducer Tet and cell culture sizes: 0.1 mM IPTG to 0 ng/ml Tet with a 10 ml cell culture; 0.1 mM to 200 ng/mL Tet with a 20 ml cell culture; 0.1 mM to 400 ng/mL with a 20 ml cell culture; 0.1 mM to 600 ng/mL with a 20 ml cell culture; 0.05 mM to 400 ng/mL with a 20 ml cell culture; and 0.05 mM to 600 ng/mL Tet with a 20 ml cell culture.

FIG. 2(B) depicts an electrophoretic analysis of FtH and FtL synthesized by the Rosetta-gami B strain of *E. coli*, on 7.5% Native PAGE, at the following ratios of the inducer IPTG to the inducer Tet and cell culture sizes: 0.1 mM IPTG to 0 ng/ml Tet with a 10 ml cell culture; 0.1 mM to 200 ng/mL Tet with a 20 ml cell culture; 0.1 mM to 400 ng/mL with a 20 ml cell culture; 0.1 mM to 600 ng/mL with a 20 ml cell culture; 0.05 mM to 400 ng/mL with a 20 ml cell culture; and 0.05 mM to 600 ng/mL Tet with a 20 ml cell culture.

Figure 3B:
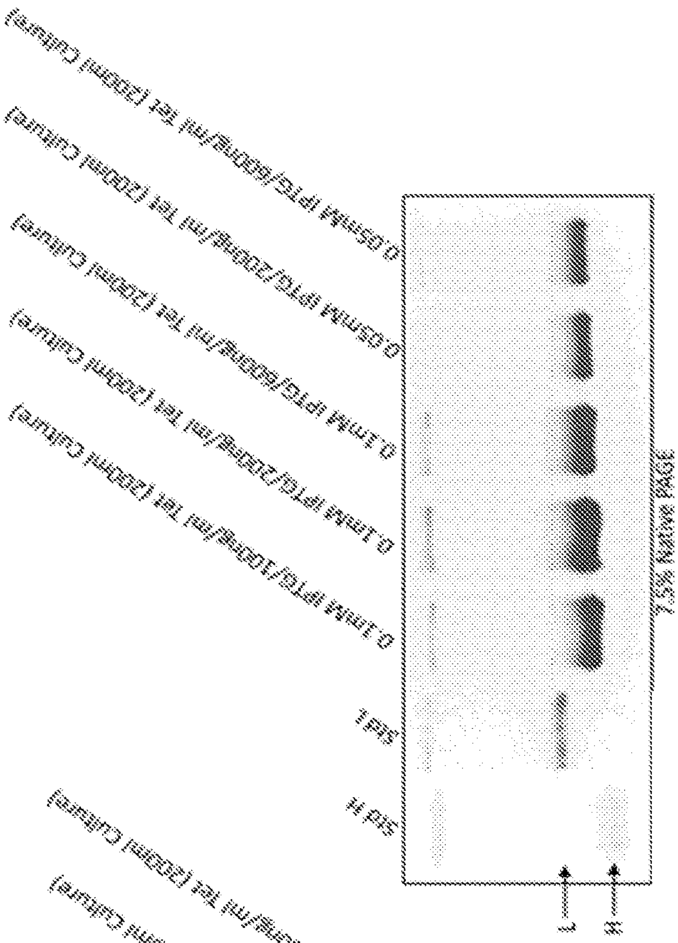
FIGS. 3(A) and 3(B), depict electrophoretic analyses, on 12% SDS PAGE and 7.5% Native PAGE respectively, of ferritin expressed by an *E. coli* cell culture at various inducer ratios and a constant cell culture size.
Figure 3A:
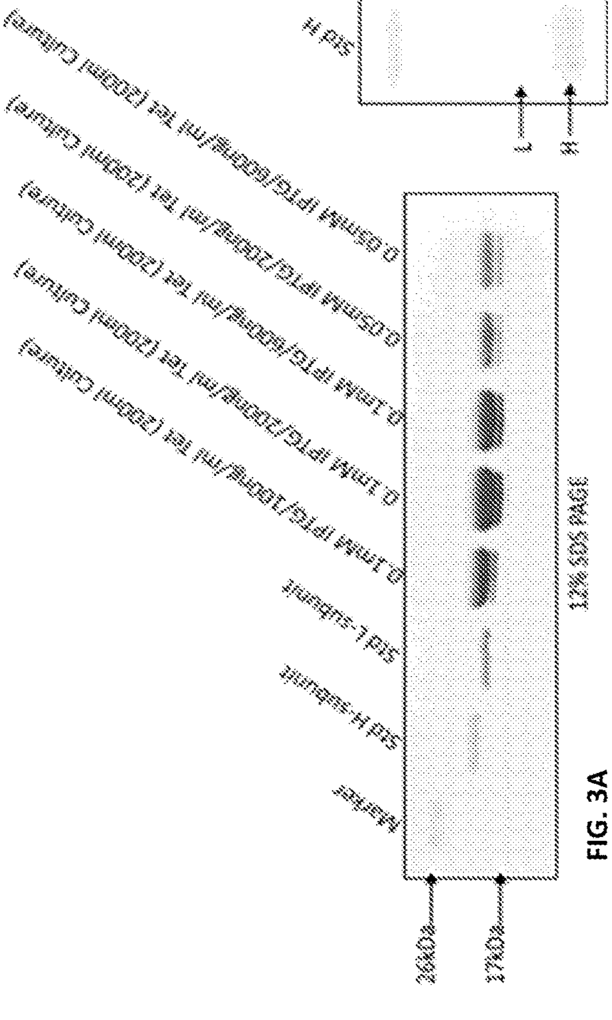

FIG. 3(A) depicts an electrophoretic analysis of FtH and FtL synthesized by the Rosetta-gami B strain, on 12% SDS PAGE, with a 200 mL cell culture at following ratios of the inducer IPTG to the inducer Tet: 0.1 mM IPTG to 100 ng/ml Tet; 0.1 mM to 200 ng/mL Tet; 0.1 mM IPTG to 600 ng/mL Tet; 0.05 mM IPTG to 200 ng/mL Tet; 0.05 mM IPTG to 600 ng/mL Tet; and 0.05 mM to 600 ng/mL Tet with a 20 ml cell culture.

FIG. 3(B) depicts an electrophoretic analysis of FtH and FtL synthesized by the Rosetta-gami B strain of *E. coli*, on 7.5% Native PAGE, with a 200 mL cell culture at following ratios of the inducer IPTG to the inducer Tet: 0.1 mM IPTG to 100 ng/ml Tet; 0.1 mM to 200 ng/mL Tet; 0.1 mM IPTG to 600 ng/mL Tet; 0.05 mM IPTG to 200 ng/mL Tet; 0.05 mM IPTG to 600 ng/mL Tet; and 0.05 mM to 600 ng/mL Tet with a 20 ml cell culture.

As shown in FIG. 3(A), with a 10-fold volume increase, bands in 12% SDS PAGE showed a similar trend with protein bands moving closer to standard FtH when high concentration of IPTG is used (FtH rich ferritin) but closer to standard L, when high concentration of Tet is used (FtL rich ferritin). Moreover, a more intense band corresponding to FtH is observed under 0.1 mM IPTG. On the contrary, an intense FtL band is observed when higher concentration of Tet is used.

Figure 4B:
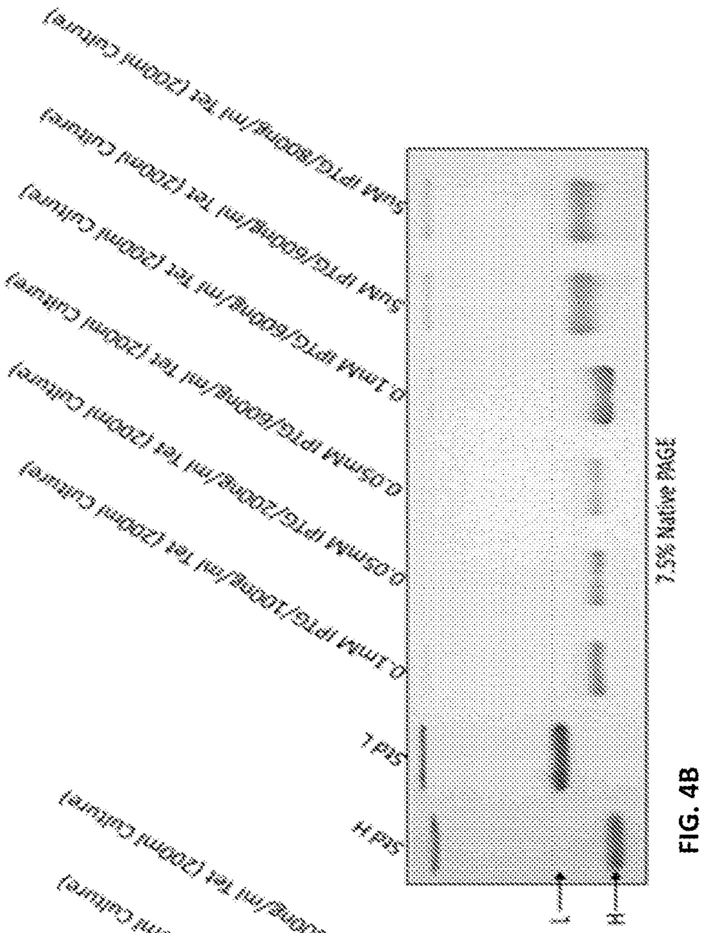
FIGS. 4(A) and 4(B), depict electrophoretic analyses, on 12% SDS PAGE and 7.5% Native PAGE respectively, of ferritin expressed by an *E. coli* cell culture at various inducer ratios and a constant cell culture size.
Figure 4A:
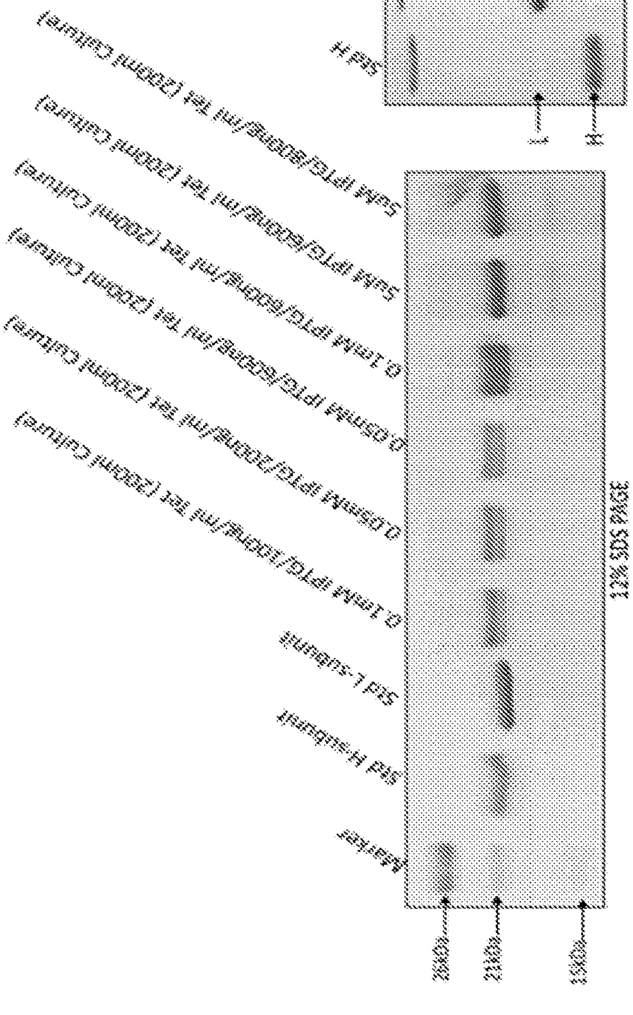

FIG. 4(A) depicts an electrophoretic analysis of FtH and FtL synthesized by the Rosetta-gami B strain of *E. coli*, on 12% SDS PAGE, with a 200 mL cell culture at following ratios of the inducer IPTG to the inducer Tet: 0.1 mM IPTG to 100 ng/ml Tet; 0.05 mM IPTG to 200 ng/mL Tet; 0.05 mM IPTG to 600 ng/mL Tet; 0.1 mM IPTG to 600 ng/mL Tet; 5 μM IPTG to 600 ng/mL Tet; and 5 μM to 800 ng/m L.

FIG. 4(B) depicts an electrophoretic analysis of FtH and FtL synthesized by the Rosetta-gami B strain of *E. coli*, on 7.5% Native PAGE, with a 200 mL cell culture at following ratios of the inducer IPTG to the inducer Tet: 0.1 mM IPTG to 100 ng/ml Tet; 0.05 mM IPTG to 200 ng/mL Tet; 0.05 mM IPTG to 600 ng/mL Tet; 0.1 mM IPTG to 600 ng/mL Tet; 5 μM IPTG to 600 ng/mL Tet; and 5 μM to 800 ng/mL Tet.

Further, induction of FtH and FtL, and subsequent ferritin formation, was compared within the two hosts in 12% SDS PAGE and 7.5% Native PAGE.

Figure 5B:
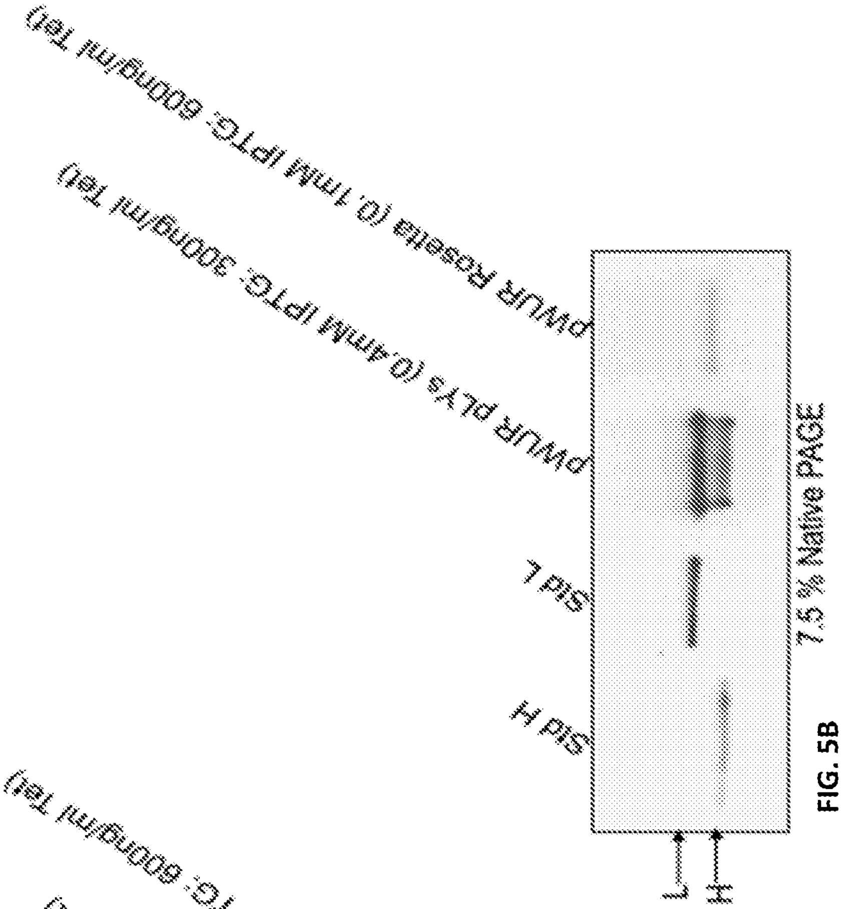
FIGS. 5(A) and 5(B), depict electrophoretic analyses, on 12% SDS PAGE and 7.5% Native PAGE respectively, of ferritin expressed by various *E. coli* cell cultures at various inducer ratios.
Figure 5A:
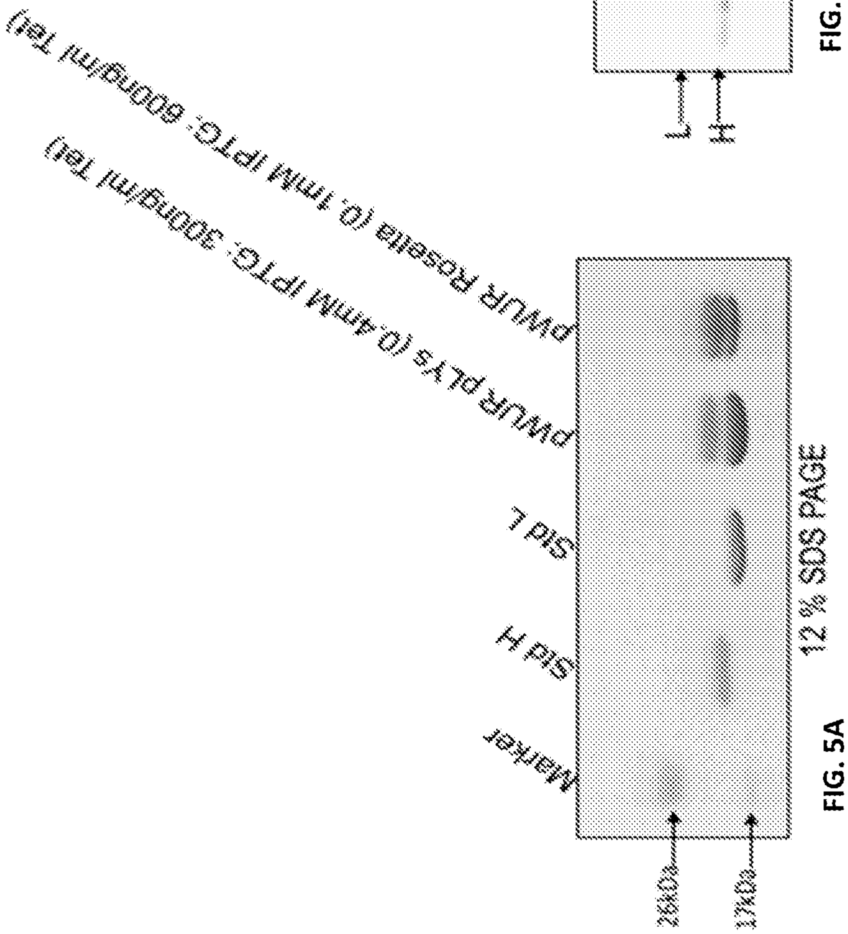

FIG. 5(A) depicts an electrophoretic analysis, on 12% SDS PAGE, of a cell culture of the BL21(DE3) pLys strain of *E. coli* at a ratio of 0.4 mM IPTG to 300 ng/mL Tet and a cell culture of the Rosetta-gami B strain of *E. coli* at a ratio of 0.1 mM IPTG to 500 ng/mL Tet. FIG. 5(B) depicts an electrophoretic analysis, on 7.5% Native PAGE, of a cell culture of the BL21(DE3) pLys strain of *E. coli* at a ratio of 0.4 mM IPTG to 300 ng/mL Tet and a cell culture of the Rosetta-gami B strain of *E. coli* at a ratio of 0.1 mM IPTG to 500 ng/mL Tet.

As depicted in FIG. 5, Rosetta-gami B showed a single observable band indicative of heteropolymer ferritin whereas BL21 showed two distinct bands indicative of FtH homopolymer and FtL homopolymer ferritin.

Having set up the conditions to simultaneously modulate the expression of FtH and FtL in a fully assembled 24-mer protein shell, further fine-tuning of the inducers concentrations led to the synthesis of various heteropolymer ferritins of different H:L ratios.

Figures 15A, 15B, 16:
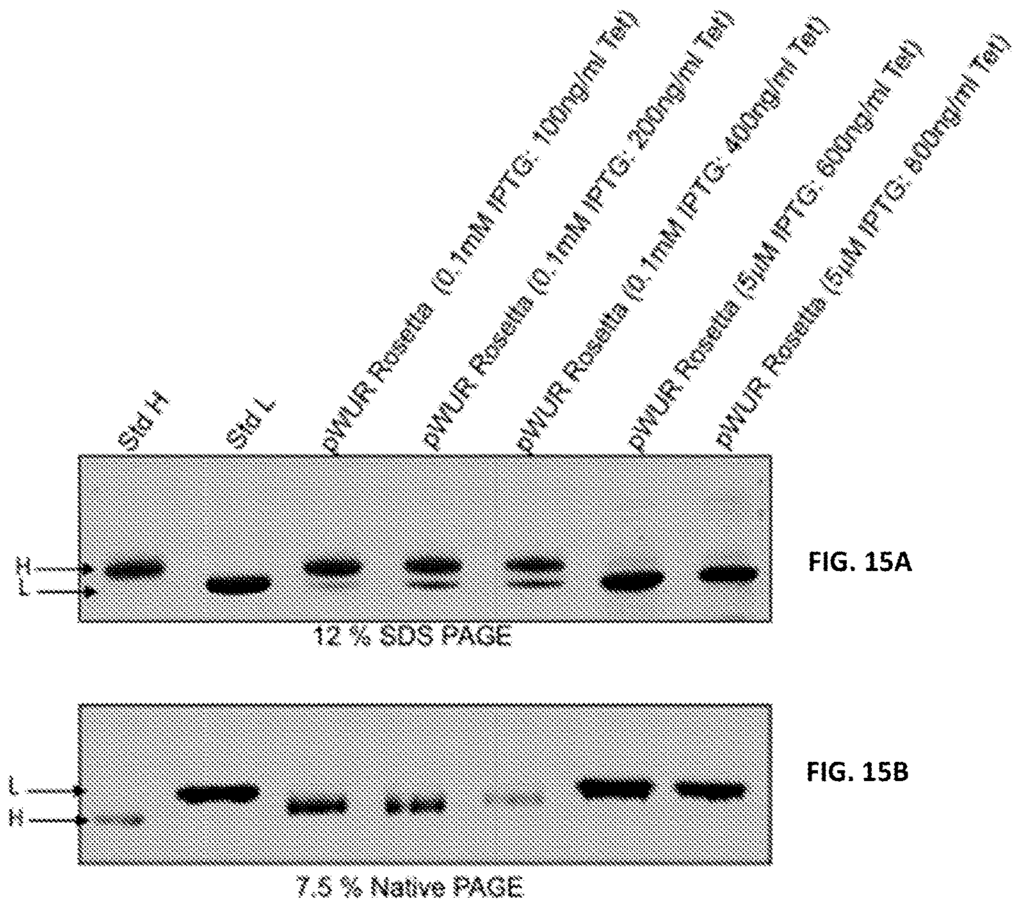
FIGS. 15(A) and 15(B) depict electrophoretic analyses, on 12% SDS PAGE and 7.5% Native PAGE respectively, of ferritin expressed by a 200 mL *E. coli* cell culture (pWUR Rosetta Gami B) at various inducer ratios.
FIG. 16 depicts predicted and experimentally measured FtH to FtL ratios in isoferritins as a function of IPTG and Tet concentrations.

FIG. 16 depicts a table showing the predicted ratio of FtH to FtL and the measured ratio of FtH to FtL at specific ratios of IPTG to Tet. By fine-tuning the inducer's concentrations, various heteropolymer ferritins of different FtH to FtL ratios in a fully assembled 24-mer protein shell were synthesized. To quantitatively characterize the subunit composition of the heteropolymers, Sodium Dodecyl Sulfate Capillary Gel Electrophoresis ("SDS-CGE") experiments were performed (see FIG. 17).

For brevity, the experiment predictions and results will be shown as such: "(a) Concentration—[IPTG Concentration μM]:[Tet Concentration ng/ml], (b) Prediction—[H:L], (c) Result—[H:L], (d) Conversion—[FtH:FtL per 24-mer ferritin]." The following are the concise results of the experiment illustrated in FIG. 16, including:

(i) Concentration—100:100, Prediction—90H:10 L, Results—88H:22 L, Conversion—21:3;

(ii) Concentration—50-100:600, Prediction—85H:15 L, Results—88H:13 L, Conversion—21:3;

(iii) Concentration—10:600, Prediction—40H:60 L, Results—36H:64 L, Conversion—8:16;
(iv) Concentration—10:800, Prediction—80H:20 L, Results—82H:18 L, Conversion—19:5;
(v) Concentration—20:800, Prediction—80H:20 L, Results—80H:20 L, Conversion—19:5,
(vi) Concentration—50:800, Prediction—85H:15 L, Results—86H:14 L, Conversion—21:3;
(vii) Concentration—100:800, Prediction—85H:15 L, Results—88H:12 L, Conversion—21:3;
(viii) Concentration—10:1000, Prediction—25H:75 L, Results—27H:73 L, Conversion—6:18; and
(ix) Concentration—0:800-1200, Prediction—0H:100 L, Results—6H:94 L, Conversion—1:23.

FIGS. 7-15 depict electrophoresis analyses on 12% SDS PAGE and 7.5% Native PAGE of various combinations of different concentrations of inducers and various cell culture volumes.

Figure 7B:
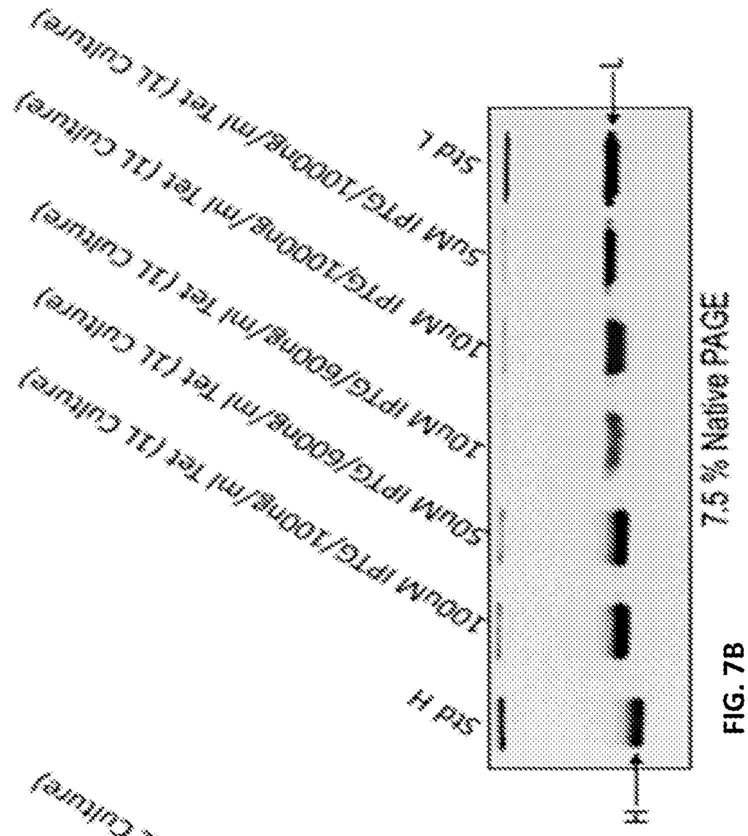
FIGS. 7(A) and 7(B), depict electrophoretic analyses, on 12% SDS PAGE and 7.5% Native PAGE respectively, of ferritin expressed by an *E. coli* cell culture (pWUR Rosetta Gami B) at various inducer ratios and a constant cell culture size. Each lane corresponds to a different cell culture and different experimental conditions.
Figure 7A:
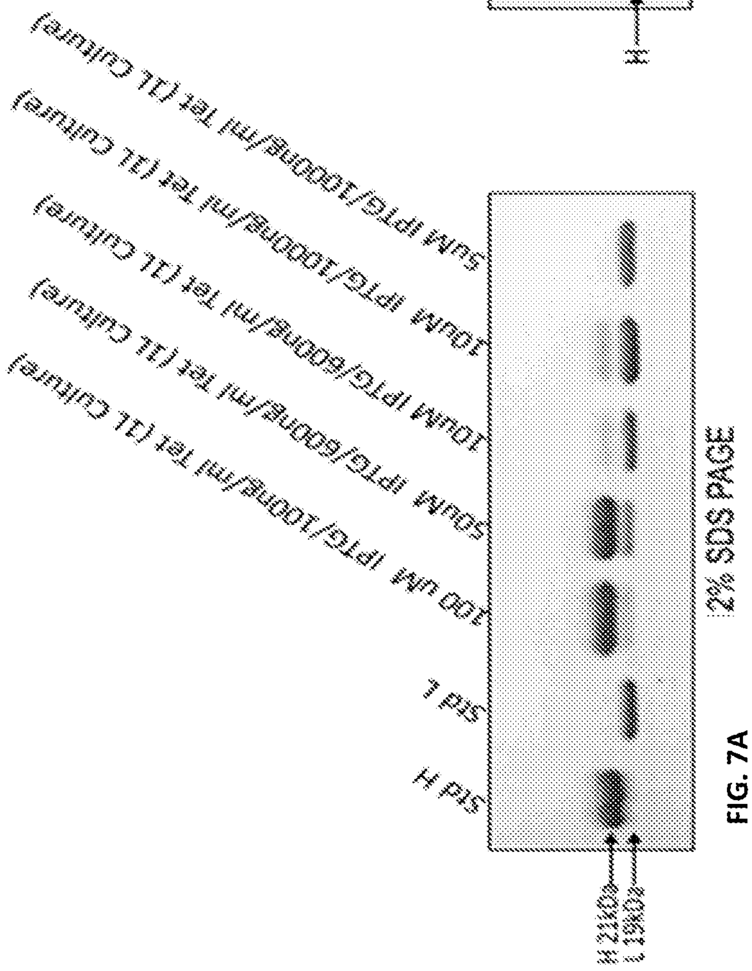

FIG. 7(A) depicts an electrophoretic analysis, on 12% SDS PAGE, of a 1 L cell culture at the following ratios of the inducer IPTG to the inducer Tet: 100 μM IPTG to 500 ng/mL Tet; 50 μM IPTG to 600 ng/mL Tet; 10 μM IPTG to 600 ng/mL Tet; 10 μM IPTG to 1000 ng/mL Tet; and 5 μM IPTG to 1000 ng/mL Tet. FIG. 7(B) depicts an electrophoretic analysis, on 7.5% Native PAGE, of 1 L cell culture at the following ratios of the inducer IPTG to the inducer Tet: 100 μM IPTG to 500 ng/mL Tet; 50 μM IPTG to 600 ng/mL Tet; 10 μM IPTG to 600 ng/mL Tet; 10 μM IPTG to 1000 ng/mL Tet; and 5 μM IPTG to 1000 ng/mL Tet.

Figure 8B:
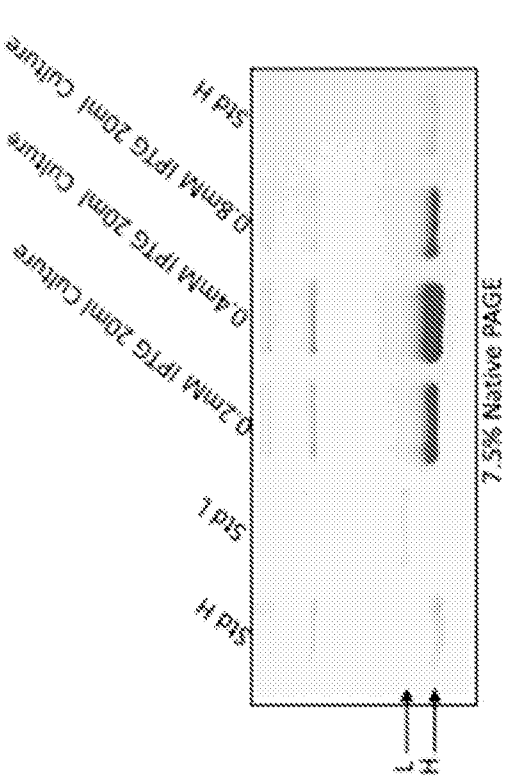
FIGS. 8(A) and 8(B), depict electrophoretic analyses, on 12% SDS PAGE and 7.5% Native PAGE respectively, of ferritin expressed by an *E. coli* cell culture (pWUR Rosetta Gami B) at various IPTG inducer concentrations and a constant cell culture size.
Figure 8D:
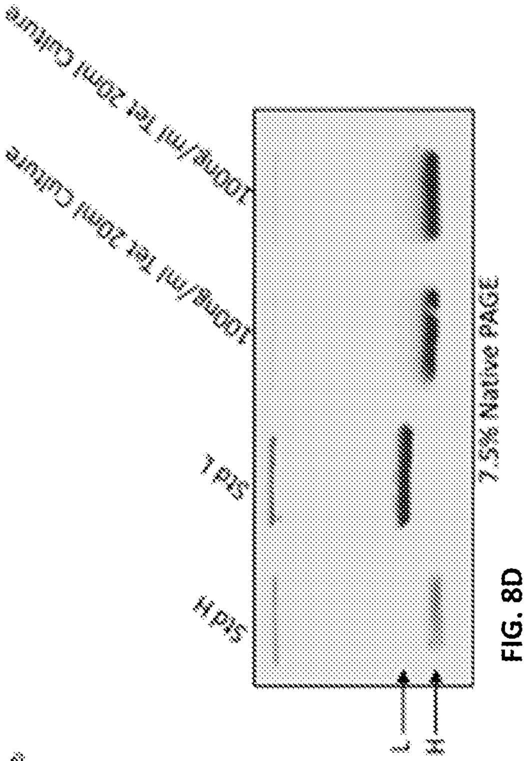
FIGS. 8(C) and 8(D), depict electrophoretic analyses, on 12% SDS PAGE and 7.5% Native PAGE respectively, of an *E. coli* cell culture (pWUR Rosetta Gami B) at various Tet inducer concentrations and a constant cell culture size.
Figure 8A:
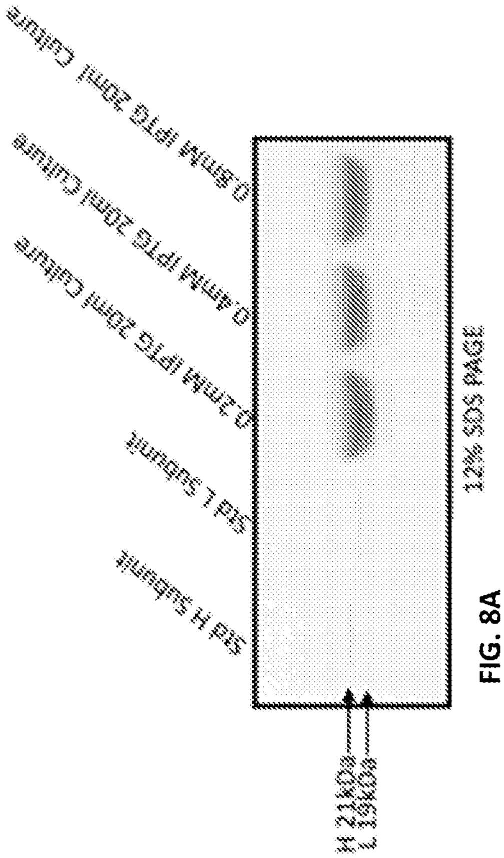

FIG. 8(A) depicts an electrophoretic analysis, on 12% SDS PAGE, of a 20 mL cell culture at the following ratios of the inducer ITPG to the inducer Tet: 0.2 mM IPTG to 0 ng/mL Tet; 0.4 mM IPTG to 0 ng/mL Tet; 0.8 mM ITPG to 0 ng/mL Tet. FIG. 8(B) depicts and electrophoretic analysis, on 7.5% Native PAGE, of a 20 mL cell culture at the following ratios of the inducer ITPG to the inducer Tet: 0.2 mM IPTG to 0 ng/mL Tet; 0.4 mM IPTG to 0 ng/mL Tet; 0.8 mM IPTG to 0 ng/mL Tet.

Figure 8C:
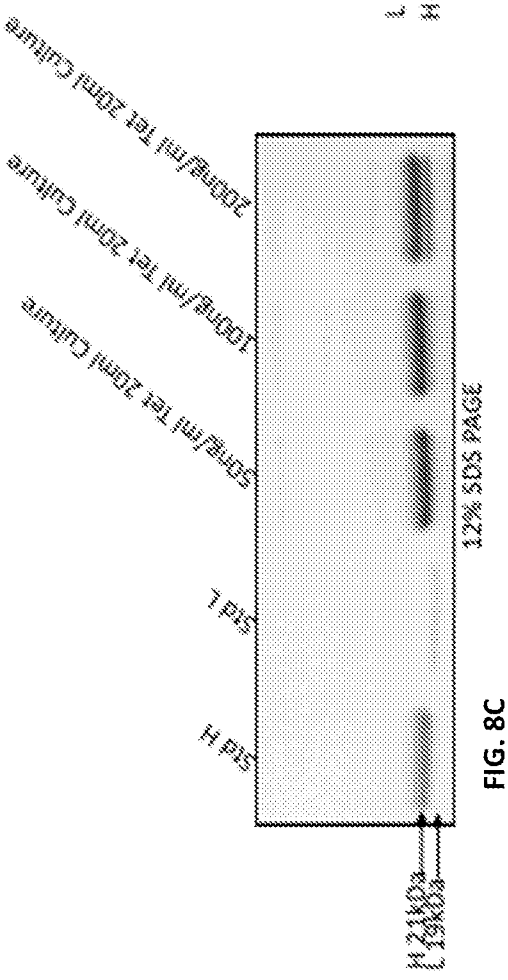

FIG. 8(C) depicts and electrophoretic analysis, on 12% SDS PAGE, of a 20 mL cell culture at the following ratios of the inducer ITPG to the inducer Tet: 0 mM IPTG to 50 ng/mL Tet; 0 mM IPTG to 100 ng/mL Tet; 0 mM ITPG to 200 ng/mL Tet. FIG. 8(C) depicts and electrophoretic analysis, on 7.5% Native PAGE, of a 20 mL cell culture at the following ratio of the inducer IPTG to the inducer Tet: 0 mM IPTG to 100 ng/mL Tet.

Figure 9B:
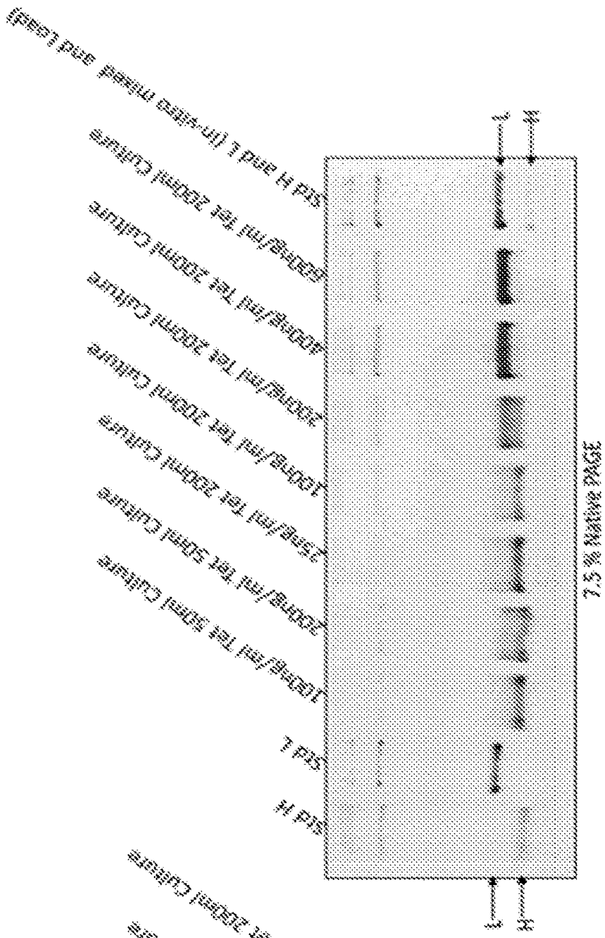
FIGS. 9(A) and 9(B) depict electrophoretic analyses, on 12% SDS PAGE and 7.5% Native PAGE respectively, of ferritin expressed by an *E. coli* cell culture (pWUR Rosetta Gami B) at various inducer ratios and cell culture sizes.
Figure 9A:
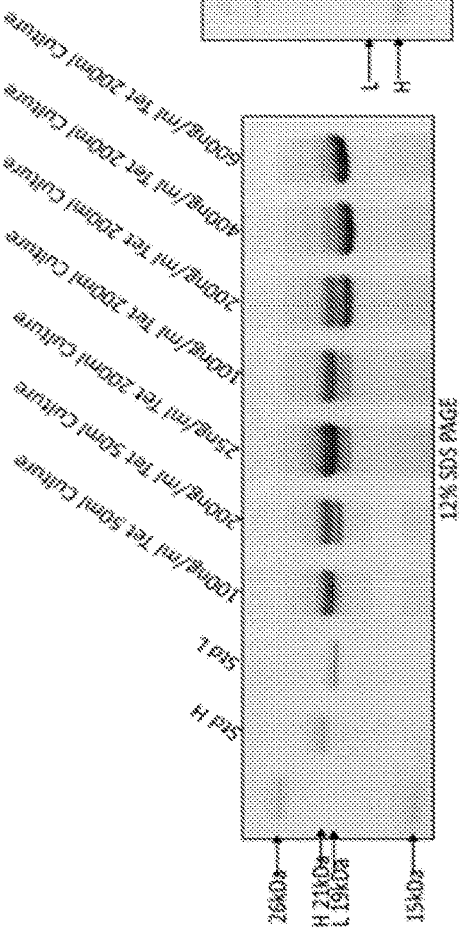

FIG. 9(A) depicts an electrophoretic analysis, on 12% SDS PAGE, of a cell culture with the following ratios of the inducer IPTG to the inducer Tet at the following cell culture sizes: 0 mM IPTG to 100 ng/mL Tet with a 50 mL cell culture; 0 mM IPTG to 200 ng/mL Tet with a 50 mL cell culture; 0 mM IPTG to 25 ng/mL Tet with a 200 mL cell culture; 0 mM IPTG to 100 ng/mL with a 200 mL cell culture; 0 mM IPTG to 200 ng/mL with a 200 mL cell culture; 0 mM IPTG to 400 ng/mL Tet with a 200 mL cell culture; and 0 mM IPTG to 600 ng/mL Tet with a 200 mL cell culture.

FIG. 9(B) depicts an electrophoretic analysis, on 7.5% SDS PAGE, of a cell culture with the following ratios of the inducer IPTG to the inducer Tet at the following cell culture sizes: 0 mM IPTG to 100 ng/mL Tet with a 50 mL cell culture; 0 mM IPTG to 200 ng/mL Tet with a 50 mL cell culture; 0 mM IPTG to 25 ng/mL Tet with a 200 mL cell culture; 0 mM IPTG to 100 ng/mL with a 200 mL cell culture; 0 mM IPTG to 200 ng/mL with a 200 mL cell culture; 0 mM IPTG to 400 ng/mL Tet with a 200 mL cell culture; and 0 mM IPTG to 600 ng/mL Tet with a 200 mL cell culture.

Figure 10B:
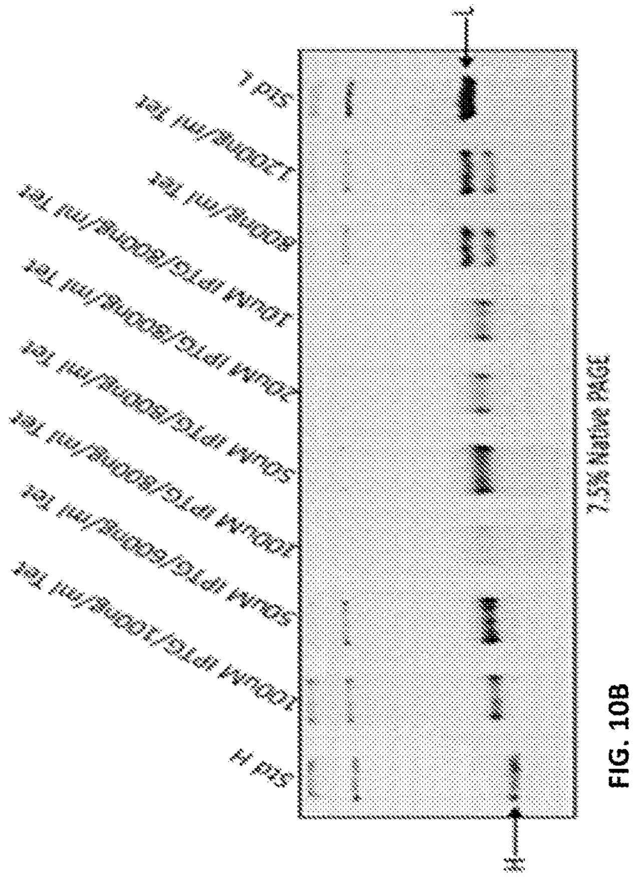
FIGS. 10(A) and 10(B) depict electrophoretic analyses, on 12% SDS PAGE and 7.5% Native PAGE respectively, of ferritin expressed by an *E. coli* cell culture (pWUR Rosetta Gami B) at various inducer concentrations and ratios.
Figure 10A:
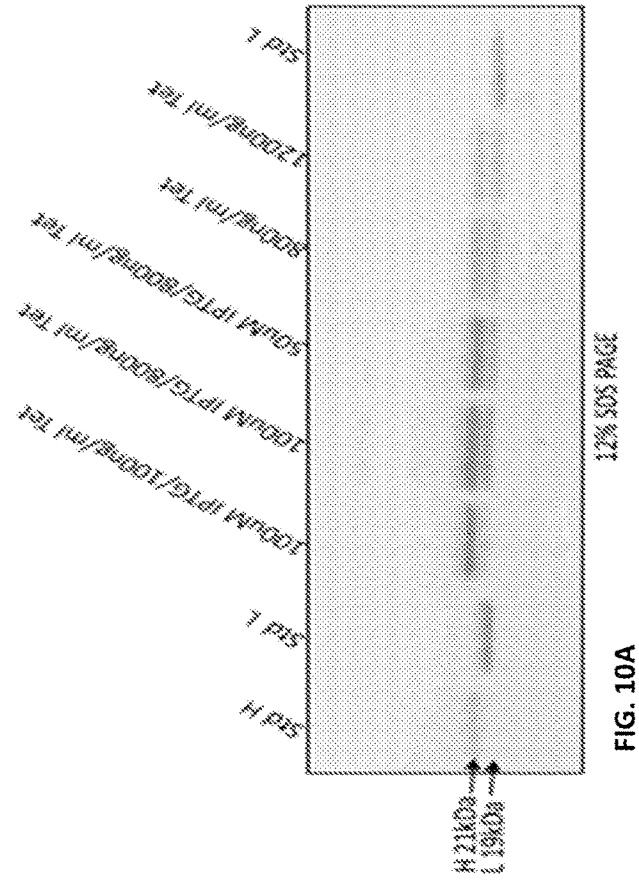

FIG. 10(A) depicts an electrophoretic analysis, on 12% SDS PAGE, of a cell culture with the following ratios of the inducer IPTG to the inducer: 100 μM IPTG to 100 ng/mL Tet; 100 μM IPTG to 800 ng/mL Tet; 50 μM IPTG to 800 ng/mL Tet; 0 μM IPTG to 800 ng/mL; 0 μM IPTG to 1200 ng/mL with a 200 mL cell culture; 0 mM IPTG to 400 ng/mL Tet with a 200 mL cell culture; and 0 mM IPTG to 600 ng/mL Tet with a 200 mL cell culture.

FIG. 10(B) depicts an electrophoretic analysis, on 7.5% SDS PAGE, of a cell culture with the following ratios of the inducer IPTG to the inducer Tet: 100 μM IPTG to 100 ng/mL Tet; 50 μM IPTG to 600 ng/mL Tet; 100 μM IPTG to 800 ng/mL Tet; 50 μM IPTG to 800 ng/mL; 20 μM IPTG to 800 ng/mL; 10 μM IPTG to 800 ng/mL Tet; 0 μM IPTG to 800 ng/mL Tet; 0 μM IPTG to 1200 ng/mL Tet.

Figure 11B:
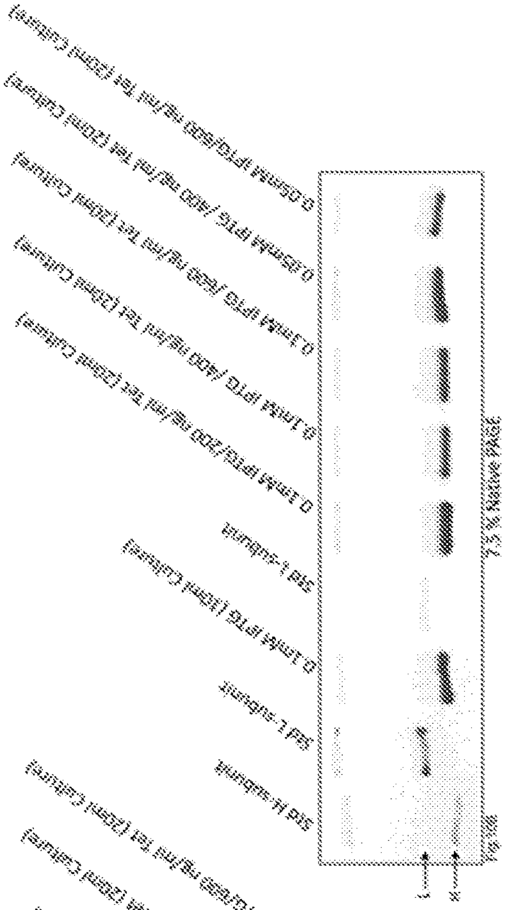
FIGS. 11(A) and 11(B) depict electrophoretic analyses, on 12% SDS PAGE and 7.5% Native PAGE respectively, of ferritin expressed by an *E. coli* cell culture (pWUR Rosetta Gami B) at various inducer ratios and cell culture sizes.
Figure 11A:
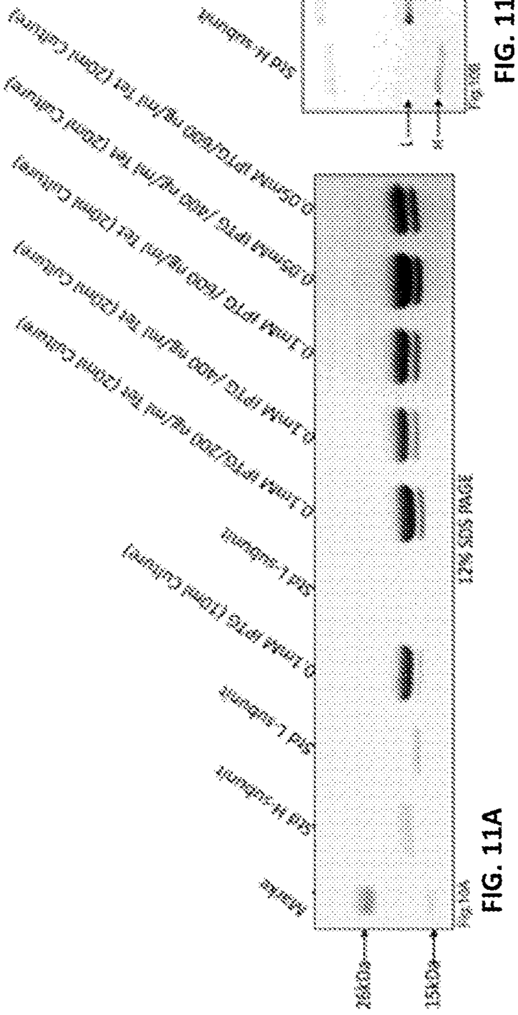

FIG. 11(A) depicts an electrophoretic analysis, on 12% SDS PAGE, of a cell culture with the following ratios of the inducer IPTG to the inducer Tet at the following cell culture sizes: 0.1 mM IPTG to 0 ng/mL Tet with a 10 mL cell culture; 0.1 mM IPTG to 200 ng/mL with a 20 mL cell culture; 0.1 mM IPTG to 400 ng/mL with a 20 mL cell culture; 0.1 mM IPTG to 600 ng/mL Tet with a 20 mL cell culture; 0.05 mM IPTG to 400 ng/mL Tet with a 20 mL cell culture; and 0.05 mM IPTG to 600 ng/mL Tet with a 20 mL cell culture.

FIG. 11(B) depicts an electrophoretic analysis, on 7.5% Native PAGE, of a cell culture with the following ratios of the inducer IPTG to the inducer Tet at the following cell culture sizes: 0.1 mM IPTG to 0 ng/mL Tet with a 10 mL cell culture; 0.1 mM IPTG to 200 ng/mL with a 20 mL cell culture; 0.1 mM IPTG to 400 ng/mL with a 20 mL cell culture; 0.1 mM IPTG to 600 ng/mL Tet with a 20 mL cell culture; 0.05 mM IPTG to 400 ng/mL Tet with a 20 mL cell culture; and 0.05 mM IPTG to 600 ng/mL Tet with a 20 mL cell culture.

Figure 12B:
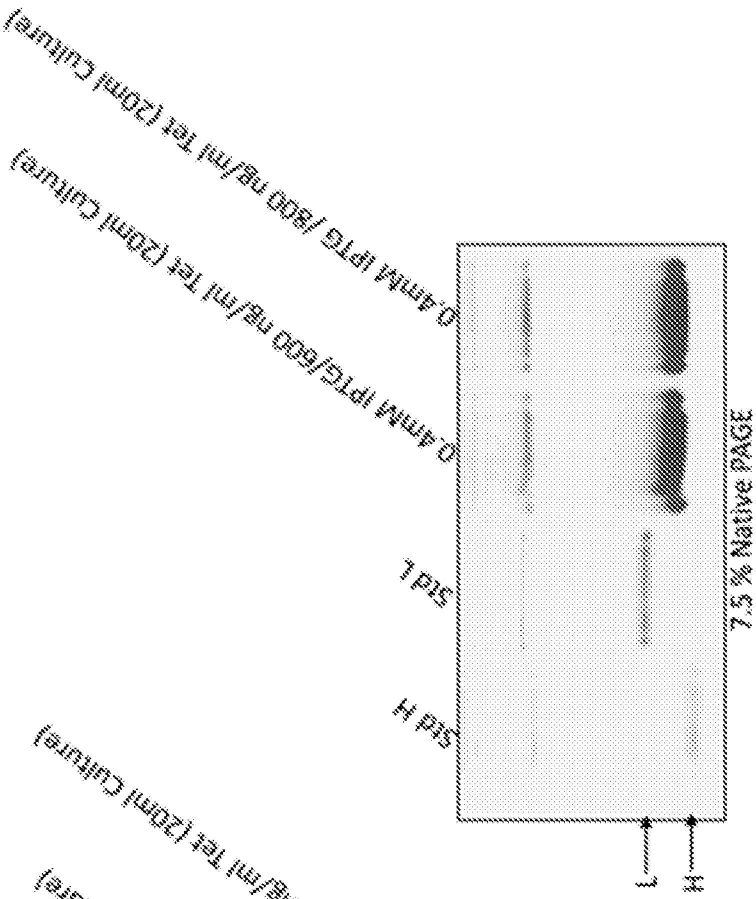
FIGS. 12(A) and 12(B) depict electrophoretic analyses, on 12% SDS PAGE and 7.5% Native PAGE respectively, of ferritin expressed by an *E. coli* cell culture (pWUR Rosetta Gami B) at various inducer ratios and a constant cell culture size.
Figure 12A:
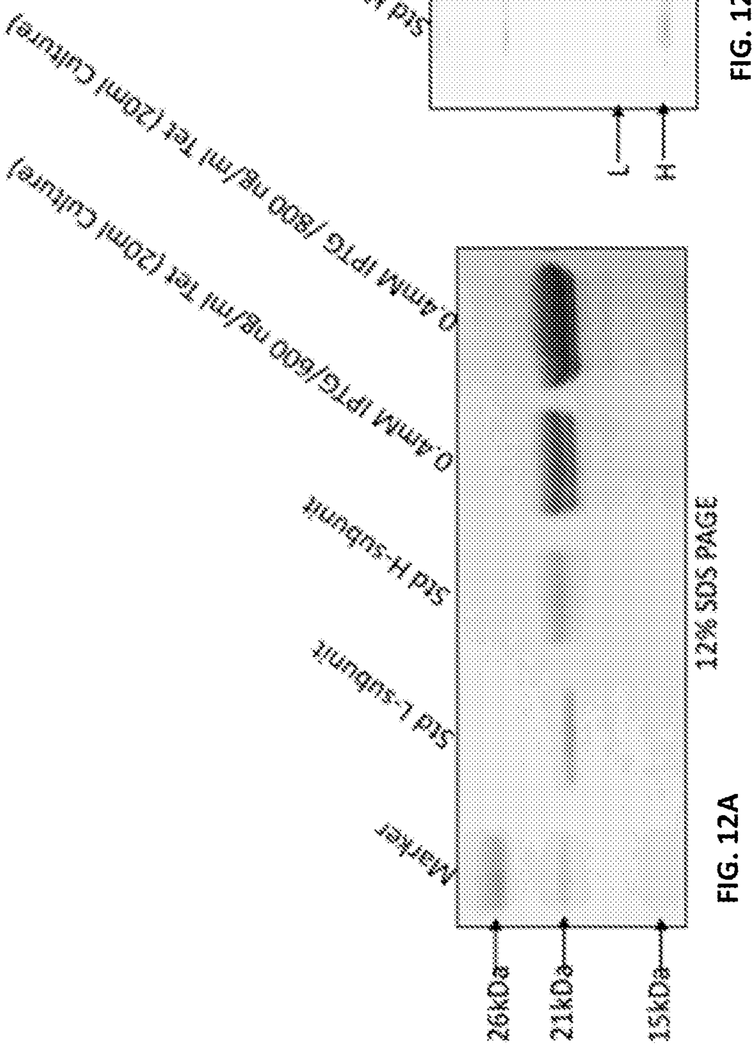

FIG. 12(A) depicts an electrophoretic analysis, on 12% SDS PAGE, of a 20 mL cell culture with the following ratios of the inducer IPTG to the inducer Tet: 0.4 mM IPTG to 600 ng/mL Tet; and 0.4 mM IPTG to 800 ng/mL Tet.

FIG. 12(B) depicts an electrophoretic analysis, on 7.5% Native PAGE, of a 20 mL cell culture with the following ratios of the inducer IPTG to the inducer Tet: 0.4 mM IPTG to 600 ng/mL Tet; and 0.4 mM IPTG to 800 ng/mL Tet.

Figure 13B:
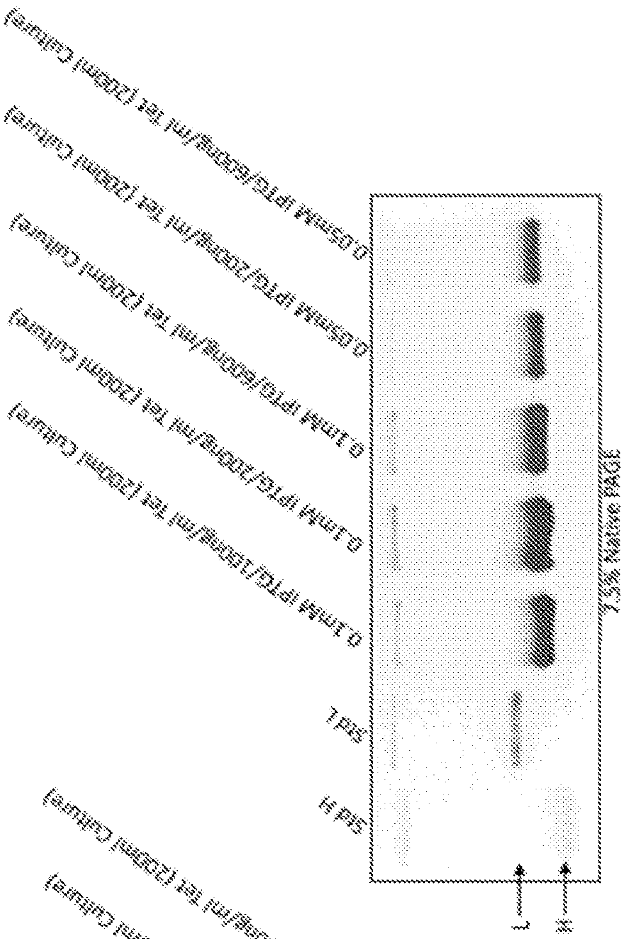
FIGS. 13(A) and 13(B) depict electrophoretic analyses, on 12% SDS PAGE and 7.5% Native PAGE respectively, of ferritin expressed by an *E. coli* cell culture (pWUR Rosetta Gami B) at various inducer ratios and a constant cell culture size.
Figure 13A:
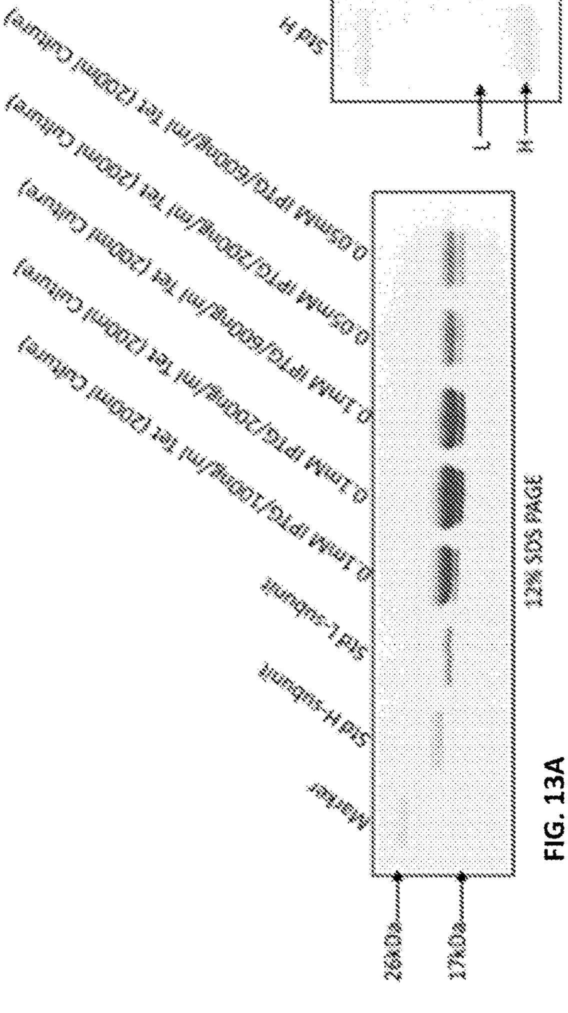

FIG. 13(A) depicts an electrophoretic analysis, on 12% SDS PAGE, of a 200 mL cell culture with the following ratios of the inducer IPTG to the inducer Tet: 0.1 mM IPTG to 100 ng/mL Tet; 0.1 mM IPTG to 200 ng/mL Tet; 0.1 mM IPTG to 600 ng/mL Tet; 0.05 mM IPTG to 200 ng/mL Tet; and 0.05 mM IPTG to 600 ng/mL Tet.

FIG. 13(B) depicts an electrophoretic analysis, on 7.5% SDS PAGE, of a 200 mL cell culture with the following ratios of the inducer IPTG to the inducer Tet: 0.1 mM IPTG to 100 ng/mL Tet; 0.1 mM IPTG to 200 ng/mL Tet; 0.1 mM IPTG to 600 ng/mL Tet; 0.05 mM IPTG to 200 ng/mL Tet; and 0.05 mM IPTG to 600 ng/mL Tet.

Figure 14B:
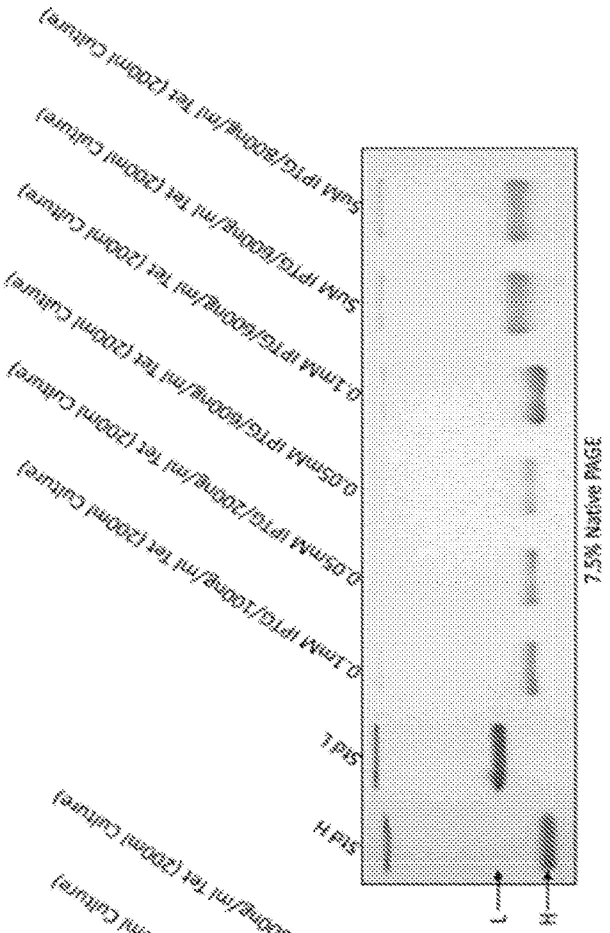
FIGS. 14(A) and 14(B) depict electrophoretic analyses, on 12% SDS PAGE and 7.5% Native PAGE respectively, of ferritin expressed by an *E. coli* cell culture (pWUR Rosetta Gami B) at various inducer ratios and a constant cell culture size.
Figure 14A:
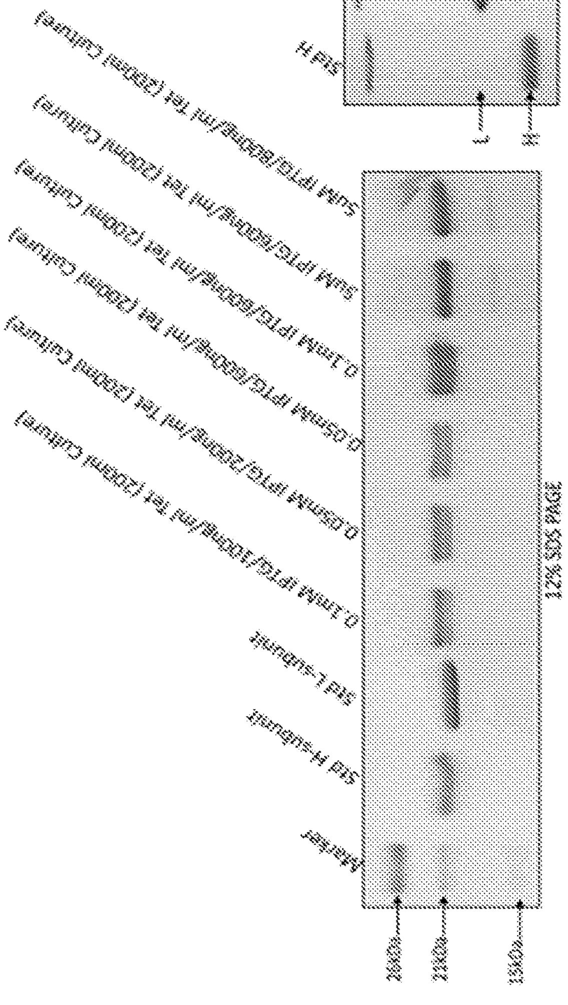

FIG. 14(A) depicts an electrophoretic analysis, on 12% SDS PAGE, of a 200 mL cell culture with the following ratios of the inducer IPTG to the inducer Tet: 0.1 mM IPTG to 100 ng/mL Tet; 0.05 mM IPTG to 200 ng/mL Tet; 0.05 mM IPTG to 600 ng/mL Tet; 0.1 mM IPTG to 600 ng/mL Tet; 5 μM IPTG to 600 ng/mL Tet; and 5 μM IPTG to 800 ng/mL Tet.

FIG. 14(B) depicts an electrophoretic analysis, on 7.5% SDS PAGE, of a 200 mL cell culture with the following ratios of the inducer IPTG to the inducer Tet: 0.1 mM IPTG to 100 ng/mL Tet; 0.05 mM IPTG to 200 ng/mL Tet; 0.05 mM IPTG to 600 ng/mL Tet; 0.1 mM IPTG to 600 ng/mL Tet; 5 μM IPTG to 600 ng/mL Tet; and 5 μM IPTG to 800 ng/mL Tet.

FIG. 15(A) depicts electrophoretic analyses, on 12% SDS PAGE, of a Rosetta-gami B cell culture with the following ratios of the inducer IPTG to the inducer Tet: 0.1 mM IPTG to 100 ng/mL Tet; 0.1 mM IPTG to 200 ng/mL Tet; 0.1 mM IPTG to 400 ng/mL Tet; 5 μM IPTG to 600 ng/mL Tet; and 5 μM IPTG to 800 ng/mL Tet.

FIG. 15(B) depicts depict electrophoretic analyses, on 12% SDS PAGE, of a Rosetta-gami B cell culture with the following ratios of the inducer IPTG to the inducer Tet: 0.1 mM IPTG to 100 ng/mL Tet; 0.1 mM IPTG to 200 ng/mL Tet; 0.1 mM IPTG to 400 ng/mL Tet; 5 μM IPTG to 600 ng/mL Tet; and 5 μM IPTG to 800 ng/mL Tet.

The various analyses show that when different combinations of IPTG and Tet concentrations are employed, heteropolymer ferritin of different FtH to FtL ratios are formed. The appearance of single protein bands on 7.5% Native PAGE in FIG. 7-15 gels indicate the production of a homogeneously assembled 24-mer ferritin species.

FIGS. 7-15 also show that the FtH rich heteropolymer ferritin shows up closer to the FtH chain ferritin while FtL rich heteropolymer ferritin shows up closer to the FtL chain ferritin. Further evidence that these protein bands represent assembled heteropolymer ferritins is revealed in the denaturing SDS-PAGE results with two superimposed bands, the top band corresponding to FtH and the lower band to FtL (FIGS. 15, 20, and 21).

To quantitatively characterize the subunit composition of the heteropolymers, SDS-CGE experiments were performed.

Figure 17:
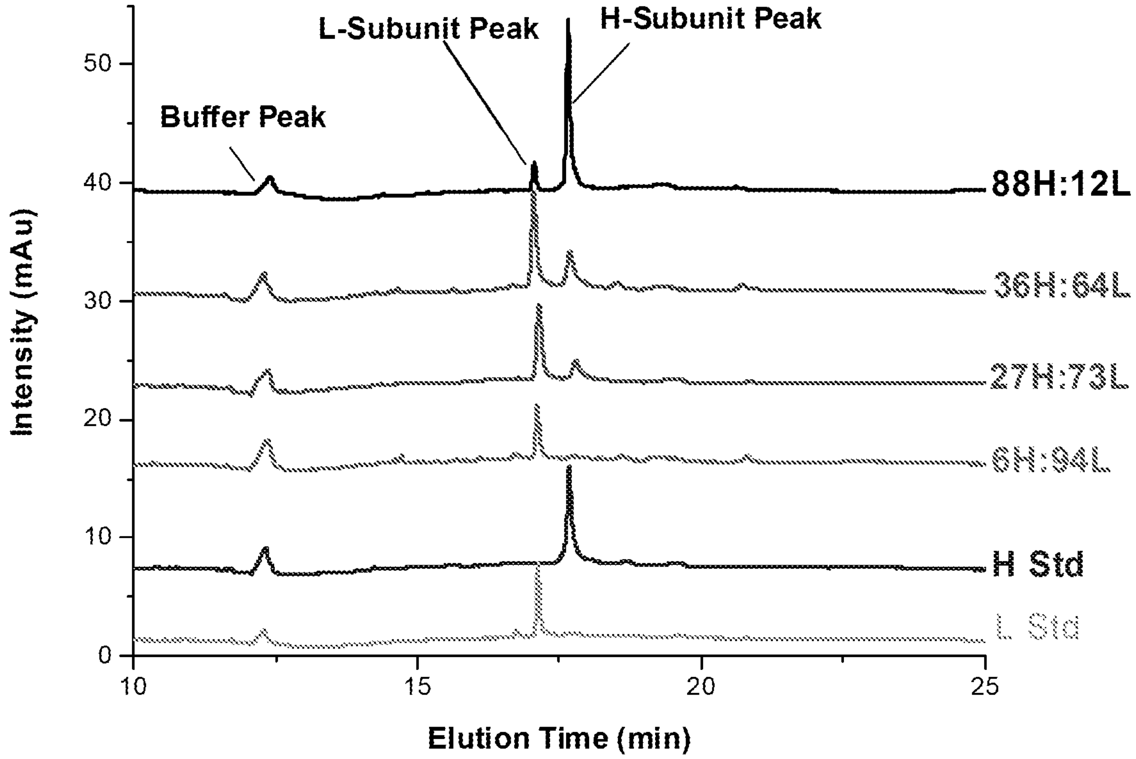
FIG. 17 depicts CE electropherograms of isoferritins showing the FtH and FtL peaks. From the total area under the peaks, the H and L % composition in each ferritin sample is calculated.

FIG. 17 depicts CE electropherograms of isoferritins showing the FtH and FtL peaks. From the total area under the peaks, the following H:L compositions within each ferritin sample were obtained: 88H:12 L; 36H:64 L; 27H:73 L; and 6H:94 L.

As depicted in FIG. 17, SDS-CGE of different heteropolymers shows the FtH and FtL peaks. From the total area under the peaks, the FtH and FtL percent composition in each ferritin sample is calculated. The subunit composition of various heteropolymers produced within the Rosetta-gami B strain shows the full spectrum of ferritin heteropolymers ranging from H24/L0 to H0/L24, by varying the concentrations of the two inducers. A control experiment was conducted to show that without induction with IPTG or Tet, no ferritin production occurs. The results of the control experiment are shown in FIG. 6. A 50 mL bacterial pre-culture was pre-inoculated overnight using a small bacterial colony from a glycerol stock until an OD value of 0.1-0.1 is reached (cell culture at lag 1 phase).

The 50 mL pre-inoculum was then added to 950 mL of LB broth with the antibiotic (streptomycin) and the culture was grown at 37° C. with 250 RPM agitation for 1:30 hrs. Then, 50 mL samples were taken at different time intervals (i.e., every 15 minutes) until OD values of approximately 0.4-0.45 are reached (cell culture at lag 2 phase or initial Log phase).

Samples were then lysed (sonicated), and the supernatant heated at 75° C. for 10-15 minutes and centrifuge at 12,000 RPM. The heat-treated supernatant samples were loaded on 12% SDS PAGE and 7.5% Native PAGE.

Figure 6A:
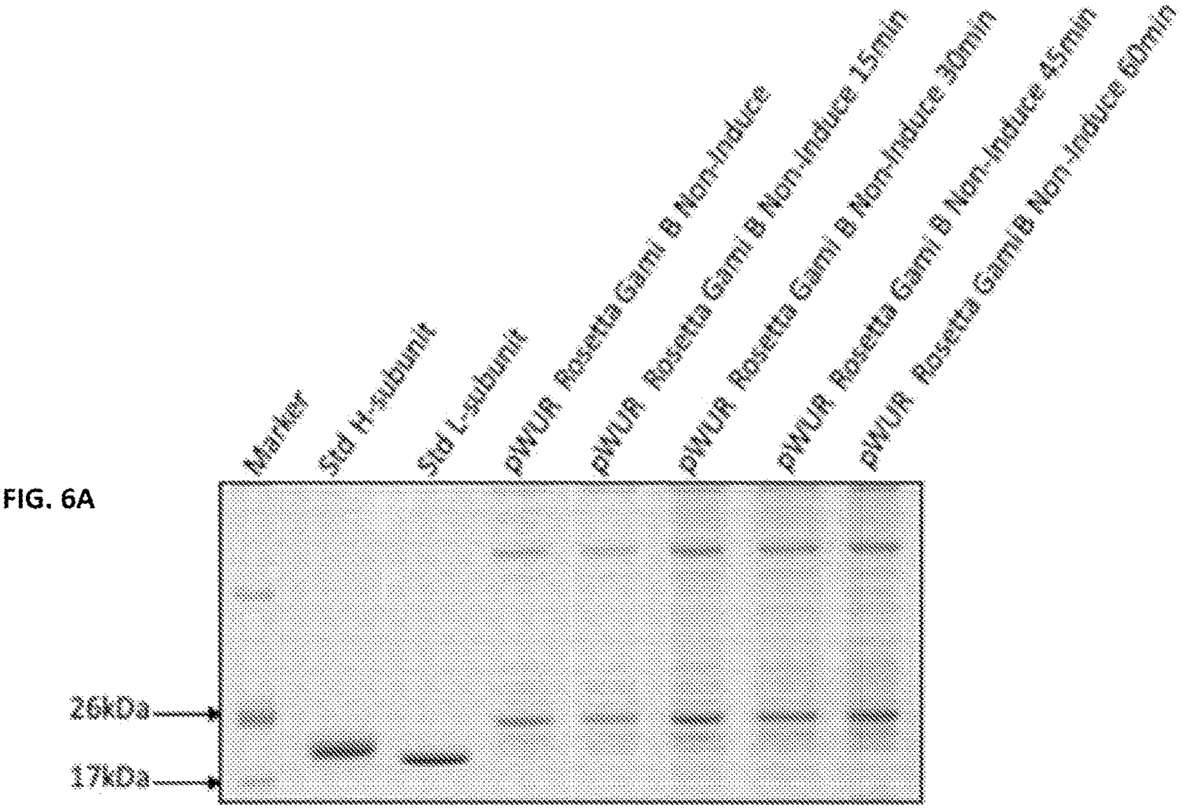
FIGS. 6(A) and 6(B), depict electrophoretic analyses, on 12% SDS PAGE and 7.5% Native PAGE respectively, of an *E. coli* cell culture, in the absence of inducers, at various time intervals.
Figure 6B:
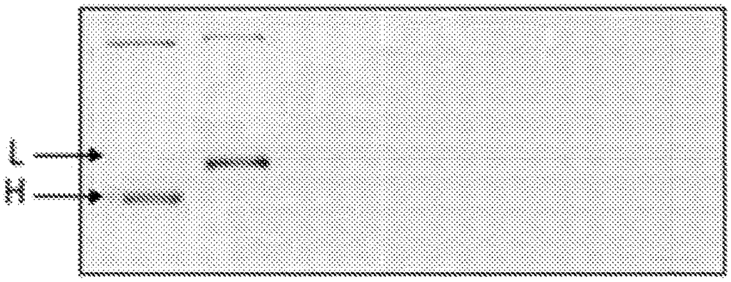

FIG. 6(A) depicts an electrophoretic analysis, on 12% SDS PAGE, of a 50 mL Rosetta-gami B cell culture, in the absence of inducers, at the following time intervals: 0 minutes; 15 minutes; 30 minutes; 45 minutes; and 60 minutes. FIG. 6(B) depicts an electrophoretic analysis, on 7.5% Native PAGE, of a 50 mL Rosetta-gami B cell culture, in the absence of inducers, at the following time intervals: 0 minutes; 15 minutes; 30 minutes; 45 minutes; and 60 minutes.

The results of FIGS. 6(A) and 6(B) show good bacterial growth within the time frame of the experiment (i.e., 60-80 minutes). As expected, without induction with IPTG or Tet, 12% SDS PAGE and 7.5% Native PAGE show no sign of ferritin production.

Therefore, the present invention is the first indication of a successful heteropolymer ferritin assembly as evidenced by the appearance of single observable protein band in 7.5% Native PAGE and 12% SDS PAGE in Rosetta-gami B. Furthermore, the present invention allows for a full spectrum of various isoferritins with H:L ratios ranging from H24/L0 to H0/L24 accomplished by varying concentrations of inducers.

These results evidence the effectiveness, reliability, and variability of the method disclosed herein. Moreover, this method is easily scalable. Inventors scaled up this method in the lab from a 50 mL culture to a 1 L culture with no adverse effects.

The claimed subject matter below is, of course, not necessarily limited to one of the embodiments described herein. In the preceding description, various aspects of claimed subject matter have been described. For purposes of explanation, specific numbers, systems, or configurations may have been set forth to provide a thorough understanding of claimed subject matter. However, it should be apparent to one skilled in the art having the benefit of this disclosure that claimed subject matter may be practiced without those specific details.

In other instances, features that would be understood by one of ordinary skill may have been omitted or simplified so as not to obscure the claimed subject matter. While certain features have been illustrated, or described herein, many modifications, substitutions, changes, or equivalents may now occur to those skilled in the art. It is, therefore, to be understood that the appended claims are intended to cover all such modifications or changes as fall within the true spirit of claimed subject matter.

What is claimed is:

1. A vector comprising a first complementary deoxynucleotide (cDNA) sequence encoding a ferritin heavy chain (FtH) amino acid sequence having at least 80%, at least 90%, at least 95%, or at least 99% sequence identity to SEQ ID NO:17, wherein the first cDNA sequence is operably linked to a first inducible promoter; and a second complementary deoxynucleotide (cDNA) sequence encoding a ferritin light chain (FtL) amino acid sequence having at least 80%, at least 90%, at least 95%, or at least 99% sequence identity to SEQ ID NO: 18, wherein the second cDNA sequence is operably linked to a second inducible promoter that is orthogonal to the first inducible promoter, wherein the vector is configured such that independent modulation of the first and second inducible promoters in a host cell is capable of producing ferritin molecules having a preselected and reproducible FtH: FtL subunit ratio.

2. A bacterial host cell comprising the vector of claim 1, wherein independent induction of the first inducible promoter and the second inducible promoter in the bacterial host cell is operable to produce ferritin molecules having a preselected and reproducible FtH:FtL subunit ratio.

3. A recombinant ferritin protein formed in the bacterial host cell of claim 2, wherein the recombinant ferritin protein comprises FtH and FtL subunits assembled at a preselected and reproducible FtH:FtL ratio produced by independently modulating the first and second inducible promoters of the vector of claim 1.

4. The recombinant ferritin protein of claim 3, wherein the recombinant ferritin protein is produced by independently modulating the first and second inducible promoters of the vector of claim 1 to obtain the preselected and reproducible FtH:FtL subunit ratio.

5. The vector of claim 1, wherein the first complementary deoxynucleotide (cDNA) sequence encoding the ferritin heavy chain (FtH) amino acid sequence has at least 90% sequence identity to SEQ ID NO: 17, and the second complementary deoxynucleotide (cDNA) sequence encoding the ferritin light chain (FtL) amino acid sequence has at least 90% sequence identity to SEQ ID NO: 18.

6. The vector of claim 1, wherein the first complementary deoxynucleotide (cDNA) sequence has at least 95% sequence identity to SEQ ID NO: 17, and the second complementary deoxynucleotide (cDNA) sequence has at least 95% sequence identity to SEQ ID NO: 18.

7. The vector of claim 1, wherein the first complementary deoxynucleotide (cDNA) sequence has at least 99% sequence identity to SEQ ID NO: 17, and the second complementary deoxynucleotide (cDNA) sequence has at least 99% sequence identity to SEQ ID NO: 18.

8. The vector of any one of claim 1, wherein the first and second sequences comprise only conservative amino acid substitutions relative to SEQ ID NO: 17 and SEQ ID NO: 18, respectively, that do not affect assembly of the ferritin nanocage or the preselected FtH:FtL ratio.

* * * * *